(12) United States Patent
Yang et al.

(10) Patent No.: US 9,376,444 B2
(45) Date of Patent: Jun. 28, 2016

(54) DIHYDROPYRIDONE P1 AS FACTOR XIA INHIBITORS

(71) Applicant: Bristol-Myers Squibb Company, Princeton, NJ (US)

(72) Inventors: Wu Yang, Princeton Junction, NJ (US); James R. Corte, Lawrenceville, NJ (US); Paul J. Gilligan, Wilmington, DE (US); Donald J. P. Pinto, Churchville, PA (US); William R. Ewing, Yardley, PA (US); Yufeng Wang, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/419,014

(22) PCT Filed: Aug. 2, 2013

(86) PCT No.: PCT/US2013/053414
§ 371 (c)(1),
(2) Date: Feb. 2, 2015

(87) PCT Pub. No.: WO2014/022766
PCT Pub. Date: Feb. 6, 2014

(65) Prior Publication Data
US 2015/0166550 A1    Jun. 18, 2015

Related U.S. Application Data

(60) Provisional application No. 61/679,197, filed on Aug. 3, 2012, provisional application No. 61/786,992, filed on Mar. 15, 2013.

(51) Int. Cl.
*A61K 31/4427* (2006.01)
*C07D 471/08* (2006.01)
*C07D 487/08* (2006.01)
*C07D 401/04* (2006.01)
*C07D 487/18* (2006.01)

(52) U.S. Cl.
CPC ............ *C07D 487/08* (2013.01); *C07D 401/04* (2013.01); *C07D 471/08* (2013.01); *C07D 487/18* (2013.01)

(58) Field of Classification Search
CPC ............................ C07D 471/08; C07D 487/08
See application file for complete search history.

(56) References Cited

FOREIGN PATENT DOCUMENTS

| WO | WO 2004/080971 | 9/2004 |
|----|----|----|
| WO | WO 2004/094372 | 11/2004 |
| WO | WO 2005/099709 | 10/2005 |
| WO | WO 2005/123050 | 12/2005 |
| WO | WO 2005/123680 | 12/2005 |
| WO | WO 2006/076575 | 7/2006 |
| WO | WO 2006/089005 | 8/2006 |
| WO | WO 2007/070816 | 6/2007 |
| WO | WO 2007/070818 | 6/2007 |
| WO | WO 2007/070826 | 6/2007 |
| WO | WO 2008/076805 | 6/2008 |
| WO | WO 2008/157162 | 12/2008 |
| WO | WO 2009/114677 | 9/2009 |
| WO | WO 2011/100401 | 8/2011 |
| WO | WO 2011/100402 | 8/2011 |
| WO | WO 2013/022814 | 2/2013 |
| WO | WO 2013/022818 | 2/2013 |
| WO | WO 2013/055984 | 4/2013 |
| WO | WO 2013/056034 | 4/2013 |
| WO | WO 2013/056060 | 4/2013 |
| WO | WO 2013/093484 | 6/2013 |
| WO | WO 2013/118805 | 8/2013 |
| WO | WO 2013/174937 | 11/2013 |

*Primary Examiner* — Brian McDowell
(74) *Attorney, Agent, or Firm* — Hong Liu

(57) ABSTRACT

The present invention provides compounds of Formula (VIII): or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

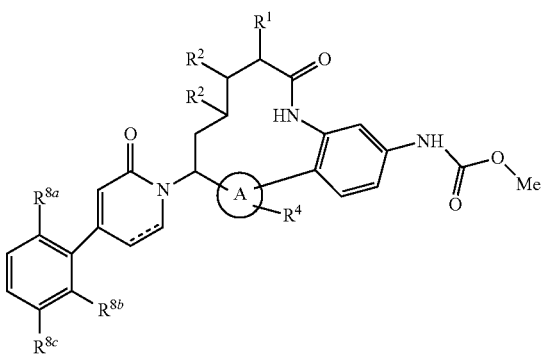

(VIII)

9 Claims, No Drawings

DIHYDROPYRIDONE P1 AS FACTOR XIA INHIBITORS

CROSS REFERENCES TO RELATED APPLICATIONS

This application is a 371 of International Application No. PCT/US2013/053414, filed on Aug. 2, 2013, which claims the benefit of U.S. Provisional Application Ser. No. 61/679,197 filed on Aug. 3, 2012 and U.S. Provisional Application Ser. No. 61/786,992 filed on Mar. 15, 2013 which are incorporated herein by reference.

FIELD OF THE INVENTION

The present invention relates generally to novel macrocyclic compounds, and their analogues thereof, which are inhibitors of factor XIa and/or plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

Plasma prekallikrein is a zymogen of a trypsin-like serine protease and is present in plasma at 35 to 50 mg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" Expert Opin. Biol. Ther. 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" Diabetes, 2011, 60, p 1590-98). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective inhibitors of serine protease enzymes, especially factor XIa and/or plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (VIII):

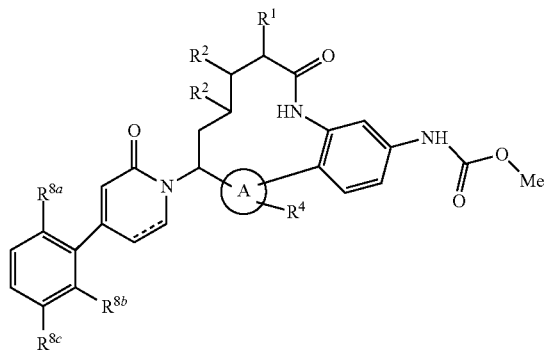

(VIII)

or stereoisomers, tautomers, pharmaceutically acceptable salts, solvates, or prodrugs thereof, wherein:

ring A is independently selected from

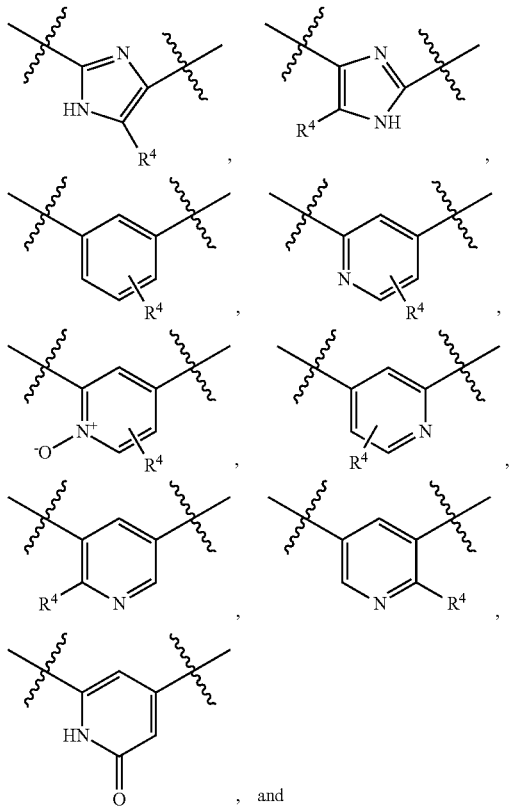

, and

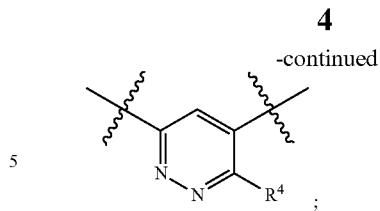

;

is an optional bond;
$R^1$ is independently selected from H, hydroxyl, and $C_{1-4}$alkyl;
$R^2$, at each occurrence, is independently selected from H and hydroxyl;
$R^4$ is independently selected from H, OH, F, $OC_{1-4}$ alkyl, and CN;
$R^{8a}$ is independently selected from H, F, Cl, and Br;
$R^{8b}$ is independently selected from H and F; and
$R^{8c}$ is independently selected from H, F, and Cl.

In another aspect, the present invention provides compounds of Formula (VIII), or stereoisomers, tautomers, pharmaceutically acceptable salts, solvates, or prodrugs thereof, wherein:

ring A is independently selected from

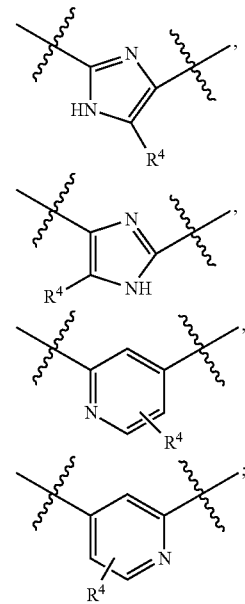

other variables are as defined in Formula (VIII) above.

In another aspect, the present invention provides compounds of Formula (IX):

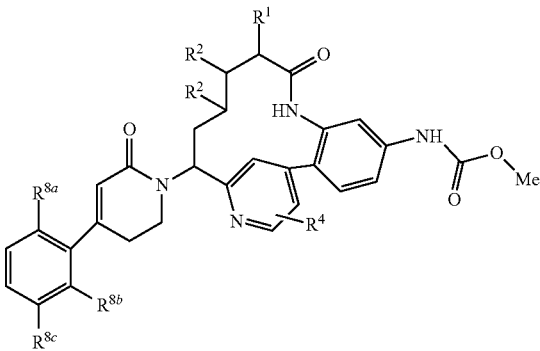

(IX)

or stereoisomers, tautomers, pharmaceutically acceptable salts, solvates, or prodrugs thereof, wherein:

$R^1$ is independently selected from H and methyl;
$R^2$, at each occurrence, is independently selected from H and hydroxyl;
$R^4$ is independently selected from H, OH, F, $OC_{1-4}$ alkyl, and CN;
$R^{8a}$ is independently selected from H, F, Cl, and Br;
$R^{8b}$ is independently selected from H and F; and
$R^{8c}$ is independently selected from H, F, and Cl.

In another aspect, the present invention provides compounds of Formula (IX), or stereoisomers, tautomers, pharmaceutically acceptable salts, solvates, or prodrugs thereof, wherein:
$R^4$ is H;
$R^{8a}$ is independently selected from H, F, and Br;
$R^{8b}$ is F;
$R^{8c}$ is independently selected from H, F, and Cl, and other variables are as defined in Formula (IX) above.

In another embodiment, $R^{8a}$ is selected from the group consisting of H, F, Cl, and Br.

In another embodiment, $R^{8b}$ is selected from the group consisting of H, F and Cl.

In another embodiment, $R^{8b}$ is selected from the group consisting of H and F.

In another embodiment, $R^{8c}$ is Cl.

In another embodiment,

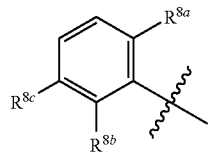

is selected from the group consisting of

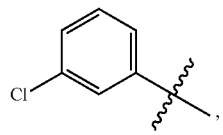

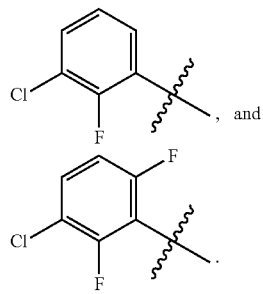

In another embodiment,

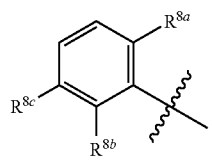 is 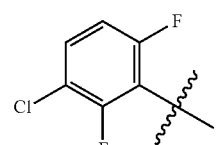

In one embodiment, the present invention provides compounds of Formulae (VIII) and (IX) or stereoisomers, tautomers, pharmaceutically acceptable salts, solvates, or prodrugs thereof, wherein ring A is independently selected from the group consisting of imidazole, pyridine, pyridinone, and pyridazine.

In another embodiment,

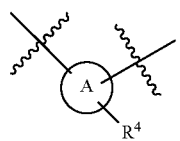

is independently selected from the group consisting of

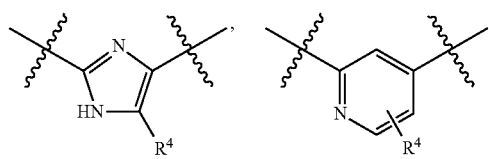

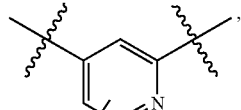

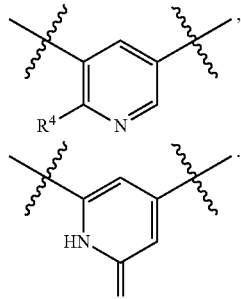

In still another embodiment,

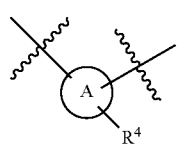

is selected from the group consisting of

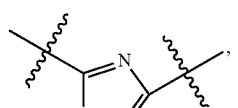

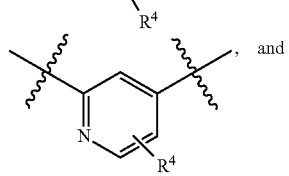

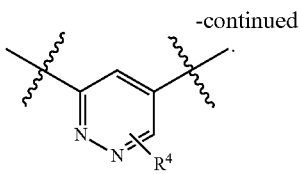

In another embodiment,

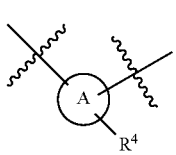 is 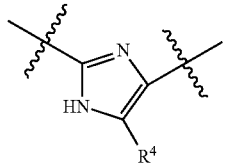

In another embodiment,

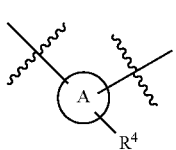 is 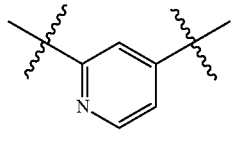

In another embodiment,

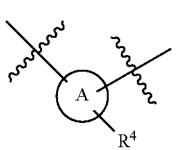 is 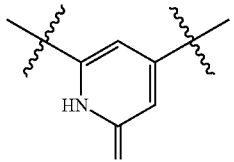

In another embodiment, $R^1$ is selected from the group consisting of H, hydroxy, and $C_{1-4}$ alkyl.

In another embodiment, $R^1$ is selected from the group consisting of H and methyl, ethyl, and isopropyl.

In one embodiment, $R^2$ is, independently at each occurrence, selected from the group consisting of H and hydroxy.

In another aspect, the present invention provides a compound selected from any subset list of compounds exemplified in the present application.

In another aspect, the present invention provides a compound selected from the group consisting of:

Methyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(6-bromo-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9-oxo-8,16,17-triazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2,4,6,15-pentaen-5-yl]carbamate Methyl N-[(10R,14S)-14-[4-(3-chloro-2,6-difluorophenyl)-6-oxo-1,2,3,6-tetrahydropyridin-1-yl]-12-hydroxy-10-methyl-9-oxo-8,16-diazatricyclo[13.3.1.0$^{2,7}$]nonadeca-1(19),2,4,6,15,17-hexaen-5-yl]carbamate.

Methyl N-[(14S)-14-[4-(6-bromo-3-chloro-2-fluorophenyl)-6-oxo-1,2,3,6-tetrahydropyridin-1-yl]-9-oxo-8,16,18-triazatricyclo[13.2.1.0$^{2,7}$]octadeca-1(17),2,4,6,15(18)-pentaen-5-yl]carbamate.

Methyl N-[(10R,14S)-14-[4-(3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate.

Methyl N-[(10R,14S)-14-[4-(3-chloro-2-fluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate.

Methyl N-[(10S,14S)-14-[4-(3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate, TFA salt.

Methyl N-[(10R,14S)-14-[4-(3-chloro-2,6-difluorophenyl)-6-oxo-1,2,3,6-tetrahydropyridin-1-yl]-17-methoxy-10-methyl-9-oxo-8,16-diazatricyclo[13.3.1.0$^{2,7}$]nonadeca-1(18),2,4,6,15(19),16-hexaen-5-yl]carbamate, TFA.

Methyl N-[(10R,14S)-14-[4-(3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9,17-dioxo-8,16-diazatricyclo[13.3.1.0$^{2,7}$]nonadeca-1(18),2,4,6,15(19)-pentaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate.

Methyl N-[(10R,14R)-14-[4-(3-chloro-2,6-difluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2(7),3,5,15-pentaen-5-yl]carbamate.

Methyl N-[(10R,14S)-14-[4-(2-bromo-5-chlorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(6-bromo-3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2(7),3,5,15,17-hexaen-5-yl]carbamate.

Methyl N-[(10R,14S)-14-[4-(6-bromo-3-chloro-2-fluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2(7),3,5,15-pentaen-5-yl]carbamate.

Methyl N-[(10S,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-2-oxo-1,2-dihydropyridin-1-yl]-10-methyl-9-oxo-8,16-diazatricyclo[13.3.1.0$^{2,7}$]nonadeca-1(19),2,4,6,15,17-hexaen-5-yl]carbamate.

(10R,14 S)-14-[4-(3-Chloro-2,6-difluorophenyl)-6-oxo-1,2,3,6-tetrahydropyridin-1-yl]-5-[(methoxycarbonyl)

amino]-10-methyl-9-oxo-8,16-diazatricyclo[13.3.1.0$^{2,7}$]
nonadeca-1(19),2,4,6,15,17-hexaen-16-ium-16-olate.

Methyl N-[(10R,14S)-14-[4-(3-chlorophenyl)-6-oxo-1,2,3,
6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-11-hydroxy-10-methyl-9-oxo-8,16-diazatricyclo[13.3.1.0$^{2,7}$]nonadeca-1(19),2,4,6,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaen-5-yl]carbamate.

Methyl N-[(10S,14R)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(10R,14R)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate.

Methyl N-[(14S)-14-[4-(3-chloro-2,6-difluorophenyl)-6-oxo-1,2,3,6-tetrahydropyridin-1-yl]-9-oxo-8,16-diazatricyclo[13.3.1.0$^{2,7}$]nonadeca-1(19),2(7),3,5,15,17-hexaen-5-yl]carbamate.

Methyl N-[(14S)-14-[4-(3-chloro-2,6-difluorophenyl)-2-oxo-1,2-dihydropyridin-1-yl]-9-oxo-8,16-diazatricyclo[13.3.1.0$^{2,7}$]nonadeca-1(19),2(7),3,5,15,17-hexaen-5-yl]carbamate.

Methyl N-[(10R,14S)-14-[4-(3-chloro-2,6-difluorophenyl)-6-oxo-1,2,3,6-tetrahydropyridin-1-yl]-17-fluoro-10-methyl-9-oxo-8-azatricyclo[13.3.1.0$^{2,7}$]nonadeca-1(19),2,4,6,15,17-hexaen-5-yl]carbamate.

In another embodiment, the compounds of the present invention have Factor XIa or plasma kallikrein Ki values ≤10 µM.

In another embodiment, the compounds of the present invention have Factor XIa Ki or plasma kallikrein values ≤1 µM.

In another embodiment, the compounds of the present invention have Factor XIa Ki or plasma kallikrein values ≤0.5 µM.

In another embodiment, the compounds of the present invention have Factor XIa Ki or plasma kallikrein values ≤0.1 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof.

Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anti-coagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The terms "alkylcarbonyl" refer to an alkyl or substituted alkyl bonded to a carbonyl.

The term "carbonyl" refers to C(=O).

The term "hydroxy" or "hydroxyl" refers to OH.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0] bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary* (13th Edition), J. Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
Boc$_2$O di-tert-butyl dicarbonate
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz carbobenzyloxy
CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs2CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexane
HOBt or HOBT 1-hydroxybenzotriazole
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride PG protecting group
POCl$_3$ phosphorus oxychloride
i-PrOH or IPA isopropanol
PS Polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris (hydroxymethyl)aminomethane
pTsOH p-toluenesulfonic acid The compounds of the present invention can be prepared in a number of ways known to one skilled in the art of organic synthesis.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, 5th Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-1370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterial—venous shunt thrombosis (Gruber et al., *Blood*, 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J. Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide,* 2nd Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial thrombosis, at doses that preserved hemostasis. (Wong P. C. et al., *American Heart Association Scientific Sessions*, Abstract No. 6118, Nov. 12-15, 2006; Schumacher, W. et al., *Journal of Thrombosis and Haemostasis,* 3(Suppl. 1):P1228 (2005); Schumacher, W. A. et al., *European Journal of Pharmacology*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo.

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., Medicine (Baltimore), 78(5):285-291 (1999); Levine M. et al., N Engl. J. Med., 334(11):677-681 (1996); Blom, J. W. et al., JAMA, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., British Journal of Surgery, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; J T Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; CHROMOGENIX® or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIIa determinations were made in 0.05 M HEPES buffer at pH 7.4 containing 0.145 M NaCl, 0.005 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time)

were measured. The following relationships were used to calculate $K_i$ values:

$$(V_{max}*S)/(K_m+S);$$

$$(v_o-v_s)/v_s=I/(K_i(1+S/K_m)) \text{ for a competitive inhibitor with one binding site; or}$$

$$v_s/v_o=A+((B-A)/1+((IC_{50}/(I)_n))); \text{ and}$$

$$K_i=IC_{50}/(1+S/K_m) \text{ for a competitive inhibitor}$$

where:

$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or Innovin®, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

The exemplified Examples disclosed below were tested in the Factor XIa assay described above and found having Factor XIa inhibitory activity. A range of Factor XIa inhibitory activity (Ki values) of 10 μM (10000 nM) was observed. Table 1 below lists Factor XIa Ki values measured at 37° C. for the following examples.

TABLE 1

| Example No. | Factor XIa Ki (nM) |
| --- | --- |
| 1 | 0.25 |
| 2 | 0.08 |
| 3 | 1.05 |
| 4 | 0.36 |
| 5 | 5.30 |
| 6 | 0.42 |
| 7 | 0.79 |
| 8 | 0.97 |
| 9 | 2.77 |
| 10 | 43.82 |
| 11 | 1.58 |
| 12 | 2.67 |
| 13 | 0.50 |
| 14 | 0.40 |
| 15 | 226.90 |
| 16 | 0.38 |
| 17 | 0.30 |
| 18 | 1.09 |
| 19 | 4.18 |
| 20 | 0.11 |
| 21 | 1.17 |
| 22 | 5.55 |
| 23 | 43.84 |
| 24 | 1.35 |
| 25 | >413.10 |
| 26 | 187.70 |
| 27 | 1.08 |
| 28 | 0.98 |
| 29 | 1.02 |

The exemplified Examples disclosed below were tested in the Plasma Kallikrein assay described above and found having plasma kallikrein inhibitory activity. A range of plasma kallikrein inhibitory activity (Ki values) of ≤10 μM (10000 nM) was observed. Table 2 below lists Plasma Kallikrein Ki values measured at 37° C. or 25° C. for the following examples.

TABLE 2

| Example No. | Plasma Kallikrein Ki (nM) |
| --- | --- |
| 1 | 0.7[a] |
| 2 | 3[a] |
| 3 | 3[a] |
| 4 | 0.5[a] |
| 5 | 12[a] |
| 6 | 0.9[a] |
| 7 | 5[a] |
| 8 | 0.8[a] |
| 9 | 2[a] |
| 10 | 9[a] |
| 11 | 0.8[a] |
| 12 | 3[a] |
| 13 | 0.6[a] |
| 14 | 0.6[a] |
| 15 | n/a |
| 16 | 4[a] |
| 17 | n/a |
| 18 | 17[a] |
| 19 | 9[b] |

TABLE 2-continued

| Example No. | Plasma Kallikrein Ki (nM) |
|---|---|
| 20 | 1[b] |
| 21 | 6[b] |
| 22 | 13[b] |
| 23 | 39[a] |
| 24 | n/a |
| 25 | 2160[b] |
| 26 | 151.6[b] |
| 27 | 2.18[b] |
| 28 | 2.39[b] |
| 29 | 6.16[b] |

[a]tested at 25° C.
[b]tested at 37° C.

The effectiveness of the compounds of the present invention as antithrombotic agents is also assessed for their metabolic stability with in vitro liver microsomal assays. Compared to the tetrahydropyridone P1 compounds, the dihydropyridone P1 compounds of the present application exhibited surprising metabolic stability. As shown in Table 3, the dihydropyridone P1 compound (Example 1) had a much prolonged half-life in human, cyno, dog, and rat liver microsomes containing cytochrome P450 enzymes, as compared to the tetrahydropyridone P1 compound.

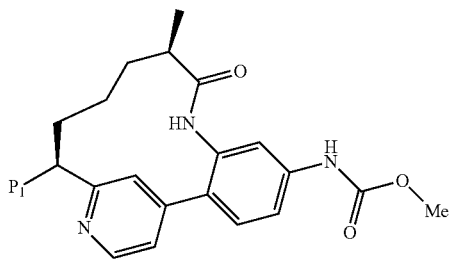

TABLE 3

| P1 | Metabolic stability (human, cyno, dog, rat) (min) |
|---|---|
| (dihydropyridone structure) | 103, 64, 67, 60 |
| (tetrahydropyridone structure) | 8, 3, 13, 15 |

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h 1M) and xylazine (10 mg/kg+10 mg/kg/h 1M). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.* 292:351-357 (2000)), can be used in this study. Male New Zealand White rabbits are anesthetized with ketamine (50 mg/kg+50 mg/kg/h 1 M) and xylazine (10 mg/kg+10 mg/kg/h 1 M). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm) The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 100 milligrams per dosage unit, and the second anti-coagulant in an amount of about 1 to about 50 milligrams per dosage unit.

Where the compounds of the present invention are administered in combination with an anti-platelet agent, by way of general guidance, typically a daily dosage may be about 0.01 to about 25 milligrams of the compound of the present invention and about 50 to about 150 milligrams of the anti-platelet agent, preferably about 0.1 to about 1 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (alliskerin) and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, P2Y$_1$ receptor antagonists, P2Y$_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors P2Y$_1$ and P2Y$_{12}$, with P2Y$_{12}$ being even more preferred. Preferred P2Y$_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-1 inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPAR-gamma modulators (e.g., rosiglitazone), compounds that have multiple functionality for modulating the activities of various combinations of PPARalpha, PPARgamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example 52366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, 52366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles,* 16(1): 35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

Representative compounds of this invention where ring A is a six-membered heterocycle (example—pyridine) can be derived from intermediates 11, the synthesis of which is described in Scheme 1. Condensation of aldehyde 1a (X=N) prepared according to a modified procedure described by Negi (*Synthesis,* 991 (1996)), with (S)-2-methylpropane-2-sulfinamide in the presence of anhydrous copper sulfate in a solvent such as DCM gives the sulfinimine 1b (Ellman, J., *J. Org. Chem.,* 64:1278 (1999)). Using a modified procedure described by Kuduk (*Tetrahedron Letters,* 45:6641 (2004)), suitably substituted Grignard reagents, for example allylmagnesium bromide, can be added to sulfinimine 1b to give a sulfinamide 1c, as a mixture of diastereomers which can be separated at various stages of the sequence. The diastereoselectivity for the addition of allymagnesium bromide to sulfinimine 1b can be improved by employing indium(III) chloride according to a modified procedure of Xu (Xu, M-H, *Organic Letters,* 2008, 10 (6), 1259). Suzuki-Miyaura coupling between 4-chloropyridine 1c and an appropriately substituted aryl or heteroaryl boronic acid or ester 1e in the presence of a base such as potassium phosphate, in a solvent mixture, such as DMSO and $H_2O$, or DMF, using a precatalyst such as $Pd(dppf)Cl_2 \cdot CH_2Cl_2$ complex provides 1g. Alternatively, the Suzuki-Miyaura coupling between boronic acid 1d and an appropriately substituted aryl or heteroaryl halide if can be used to prepared 1g. Protecting group interconversion can be accomplished in two steps to give 1h. Alternatively, the protecting group interconversion can take place initially on 1c followed by the Suzuki-Miyaura coupling. Reduction of the nitro group in 1h to an amino group may be accomplished with a reducing agent (e.g., $Zn$—$NH_4Cl$) in an inert solvent (e.g., MeOH) to give an aniline intermediate and the resulting aniline can be converted to methyl carbamate 1i by reacting with methyl chloroformate. The aniline 1i can then be coupled with an appropriately substituted carboxylic acid 1j using T3P and a base, such as pyridine, to give the amide 1k. Using a modified procedure described by Lovely (*Tetrahedron Letters,* 44:1379 (2003)), 1k, following pretreatment with p-toluenesulfonic acid to form the pyridinium ion, can be cyclized via ring-closing metathesis using a catalyst, such as Grubbs (II), in a suitable solvent, such as DCM, DCE, or toluene at elevated temperature, to give the pyridine-containing macrocycle 1l. The alkene can be reduced with hydrogen over either palladium on carbon or platinum oxide, and subsequent deprotection with TFA in DCM or 4M HCl in dioxane provides amine 1m. Compounds of the formulae 1m can be converted to compounds in this invention according to Schemes 6.

Scheme 1
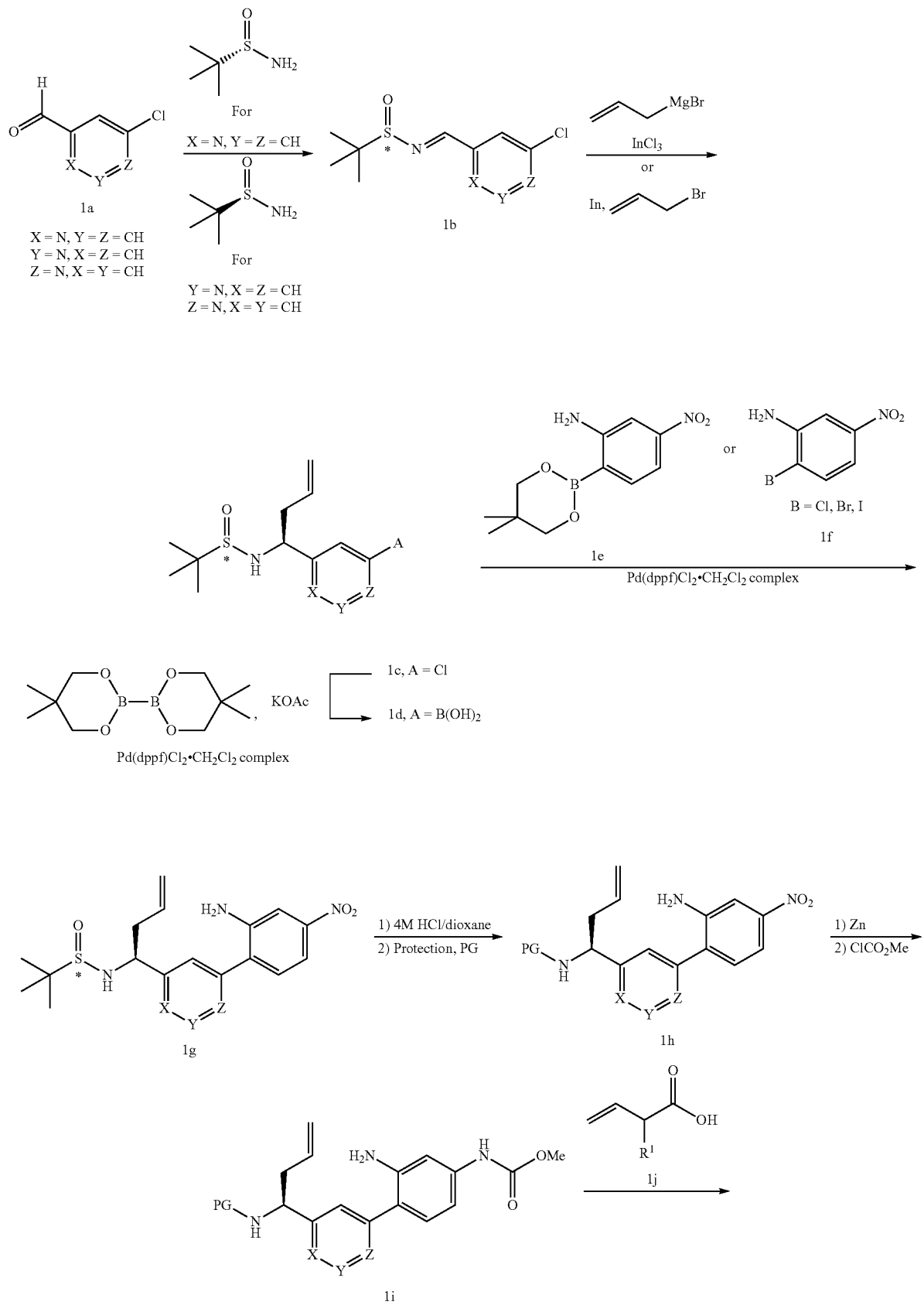

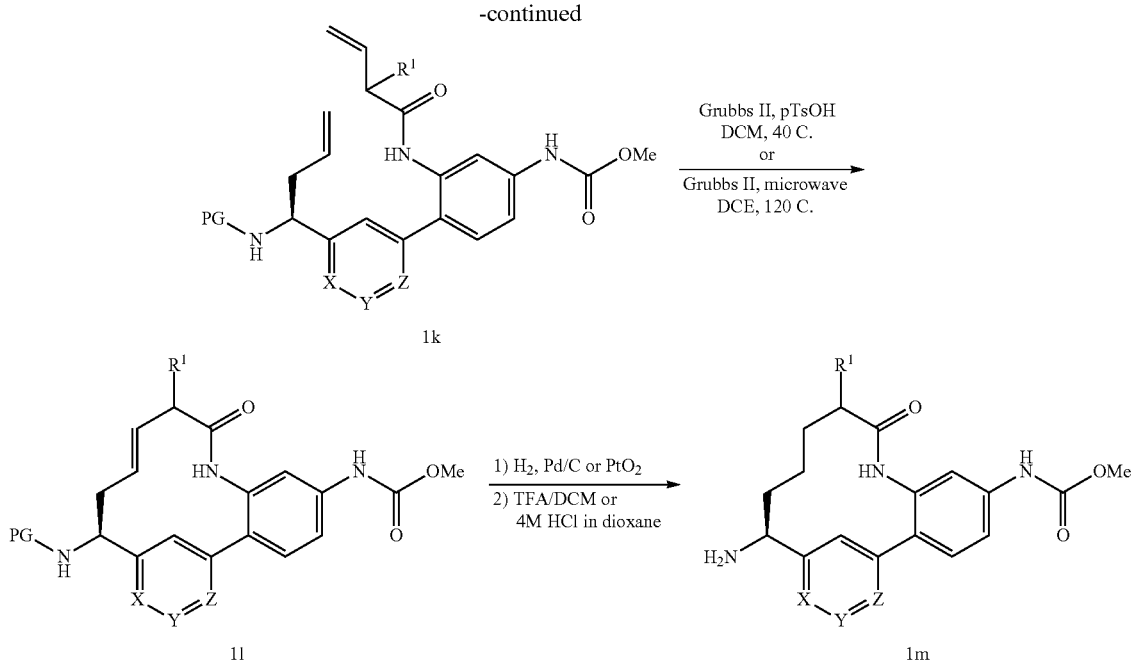

Additional pyridine containing macrocycles useful for the synthesis of compounds of this invention can also be prepared according to Scheme 1. In cases where the pyridine core is a 4-pyridine (Z=N) rather than the 2-pyridine (X=N), conversion of 1h to 1k can be easily accomplished by using an acid chloride of 1j followed by reduction and methylcarbamate formation.

Representative synthesis of compounds in this invention where Ring A is pyridone is outlined in Scheme 2. Acetal protection of methyl 4-formyl-3-nitrobenzoate 2a, followed by hydrolysis of the ester gave benzoic acid intermediate 2c. Methylcarbamate intermediate 2e was realized by acyl azide formation of 2c and subsequent Curtius rearrangement in the presence of MeOH. Upon treatment with aqueous TFA, the acetal group was converted into benzaldehyde 2f which was used in a Horner-Wadsworth-Emmons reaction with (S)-tert-butyl (1-(dimethoxyphosphoryl)-2-oxohex-5-en-3-yl)carbamate to afford 2g. Then, enone 2g was converted into key intermediate 2i by treatment with NH₄OAc and the pyridinium ester followed by nitro group reduction. Chiral separation of 2i necessary due to partial racemization during pyridone ring formation. Reaction of aniline 2j with the mixed anhydride of 2-methylbut-3-enoic acid resulted in bis-acylated product 2k which upon treatment with aqueous NaOH solution gave RCM precursor 2l. Following ring closing metathesis, the macrocyclic olefin was converted into 2n via hydrogenation. HCl deprotection of 2n gave the crucial intermediate 2o which can be coupled with various acids to afford compounds of this invention as shown in Scheme 6.

Scheme 2

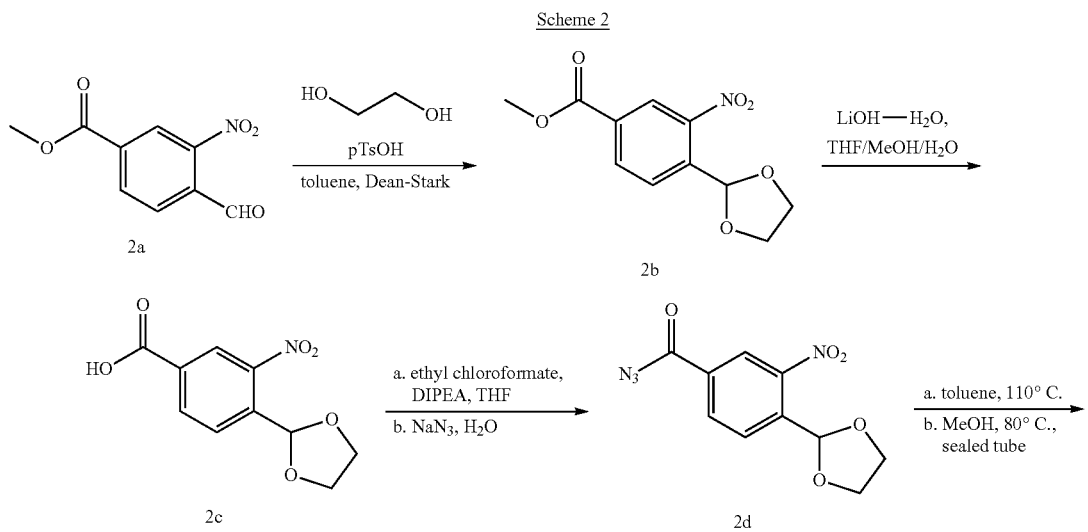

-continued
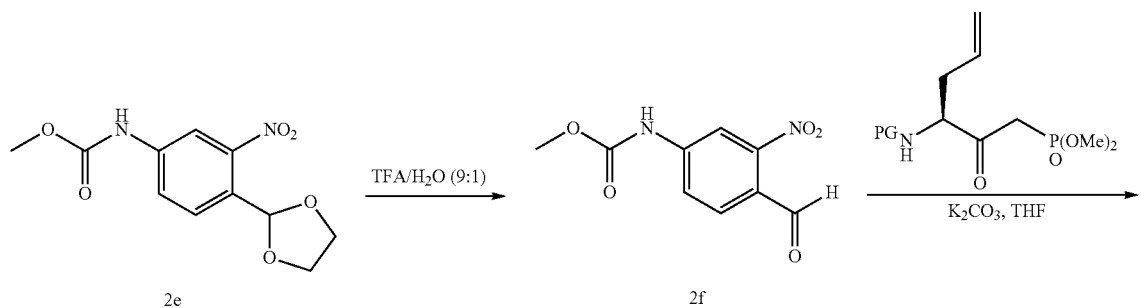
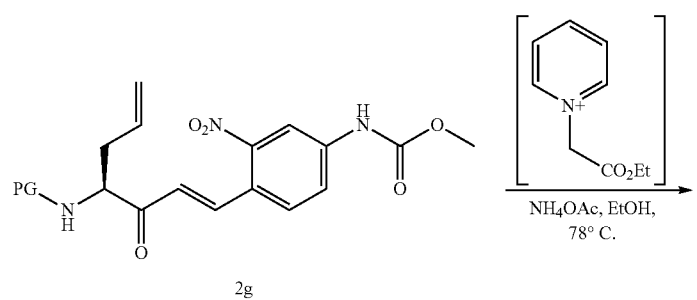
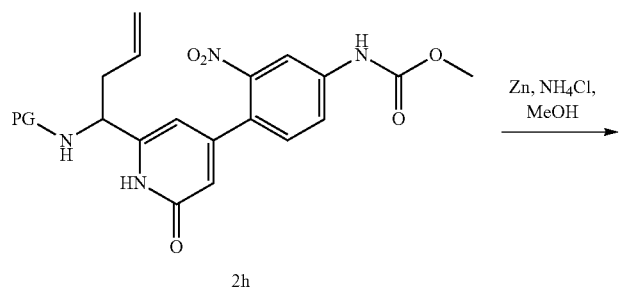
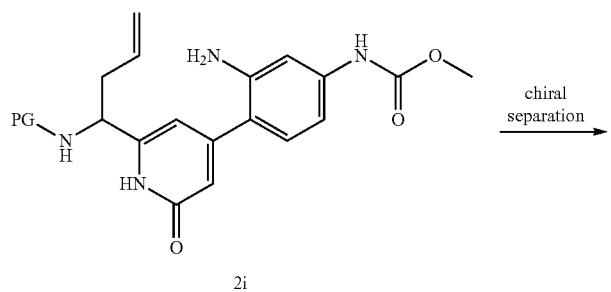
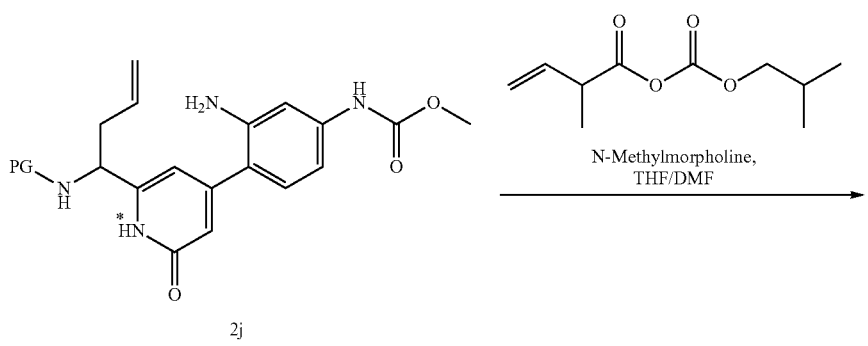

-continued
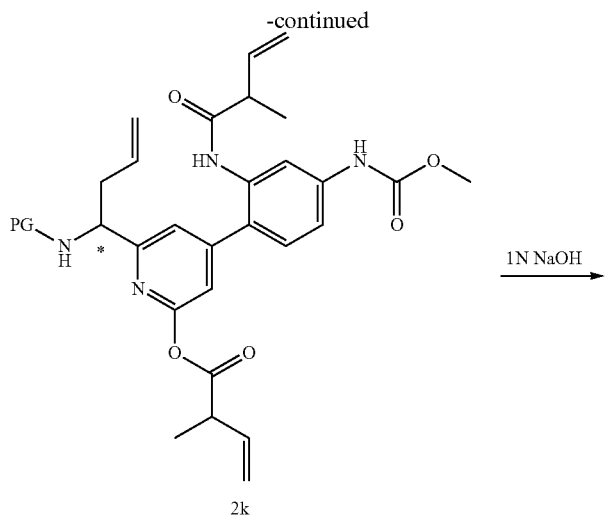
2k
1N NaOH →
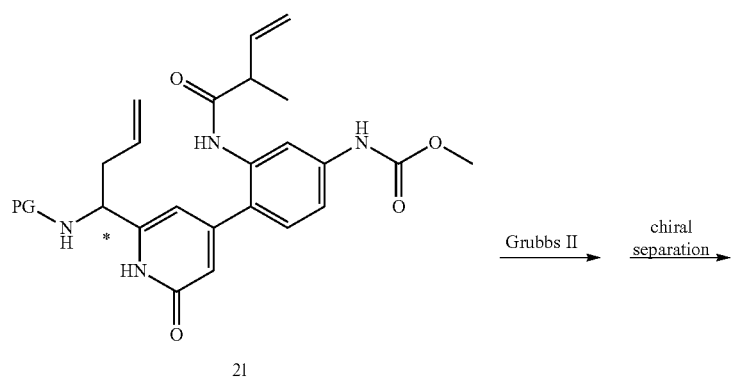
2l
Grubbs II → chiral separation →
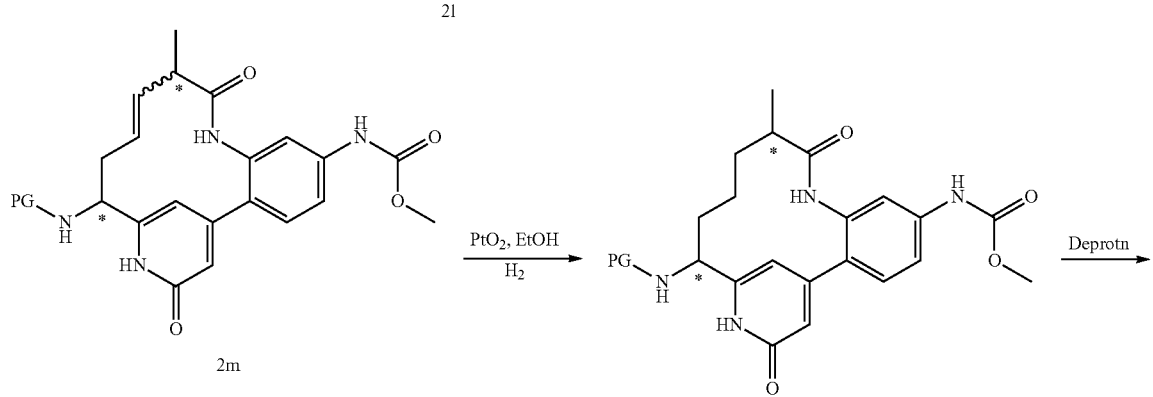
2m
PtO₂, EtOH
H₂ →
2n
Deprotn →
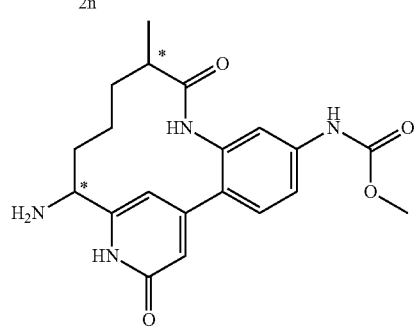
2o Methods for synthesis of a large variety of substituted pyridine compounds useful as starting materials for the preparation of compounds of the present invention are well known in the art and have been extensively reviewed. (For examples of methods useful for the preparation of pyridine starting materials see: Kroehnke, F., *Synthesis*, 1 (1976); Abramovitch, R. A., ed., "Pyridine and Its Derivatives", *The Chemistry of Heterocyclic Compounds*, 14(Suppl. 1-4), John Wiley & Sons, New York (1974); Boulton, A. J. et al., eds., *Comprehensive Heterocyclic Chemistry*, 2:165-524, Pergamon Press, New York (1984); McKillop, A., ed., *Comprehensive Heterocyclic Chemistry*, 5:1-300, Pergamon Press, New York (1996)).

In cases where suitably substituted boronic acids are not commercially available, a modification to this approach may be adopted wherein an aryl halide is subjected to a palladium mediated coupling with a diboron species such as bis(pinacolato)diboron or bis(neopentyl glycolato)diboron to provide the corresponding 4,4,5,5-tetramethyl-[1,3,2]dioxaborolane or the 5,5-dimethyl-[1,3,2]dioxaborolane intermediates using the method of Ishiyama, T. et al. (*J. Org. Chem.*, 60(23):7508-7510 (1995)). Alternately, this same intermediate can be prepared by reaction of the intermediate halide with the corresponding dialkoxyhydroborane as described by Murata et al. (*J. Org. Chem.*, 62(19):6458-6459 (1997)). The boron pinacolate intermediates can be used in place of boronic acids for coupling to the aryl/heteroaryl halides or triflates or the boron pinacolate intermediate can be converted to the boronic acids. Alternately, the corresponding boronic acids can be prepared by metal-halogen exchange of the aryl/heteroaryl halide, quenching with a trialkoxyborate reagent, and aqueous workup to provide the boronic acids (Miyaura, N. et al., *Chem. Rev.*, 95:2457 (1995)).

It is also realized that the scope of intermediate synthesis can be further extended outside the use of Suzuki-Miyaura coupling methodology since the precursor aryl halides or triflates described above are also precursors for Stille, Negishi, Hiyama, and Kumada-type cross coupling methodologies (Tsuji, J., *Transition Metal Reagents and Catalysts: Innovations in Organic Synthesis*, John Wiley & Sons (2000); Tsuji, J., *Palladium Reagents and Catalysts: Innovations in Organic Synthesis*, John Wiley & Sons (1996)).

Additional pyridazine and pyridazinone containing macrocycles can be prepared according to Scheme 3. Condensation of the potassium salt of 3a with a suitably substituted α-ketoester 3b, which is either commercially available or prepared using a modified procedure described by Domagala (*Tetrahedron Lett.*, 21:4997-5000), in a solvent such as THF generates the α,β-unsaturated ketone derivative which can then be condensed with a suitably substituted hydrazine derivative to give pyridazinone 3c. The nitro group can then be reduced to the aniline 3f with zinc and $NH_4Cl$ in methanol. The pyridazinone 3c can be converted to chloro-pyridazine 3d by deprotection of the amine protecting group, followed by treatment with $POCl_3$, then reprotection. The nitro group can be reduced to the aniline 3e with iron and AcOH. The anilines 3e and 3f can then be coupled with an appropriately substituted carboxylic acid 1g using T3P to give the amide 3g ($R^4$=Cl) and 3h ($R^4$=OH), respectively. 3g and 3h can then be cyclized via ring-closing metathesis using a catalyst, such as Grubbs (II), in a suitable solvent, such as DCM, DCE, or toluene at elevated temperature, to give the macrocycle 3i ($R^4$=Cl) and 3j ($R^4$=OH), respectively. The resulting alkenes can then be reduced with hydrogen over either palladium on carbon or platinum oxide to give 3k and 3l. 3k can be reduced with ammonium acetate and palladium on carbon to reduce the chlorine to give 3m. Subsequent deprotection of 3m and 3l provides amines 3n ($R^4$=H) and 3o ($R^4$=OH). Compounds of the formulae 3n and 3o can be converted to compounds in this invention according to Scheme 6.

Scheme 3

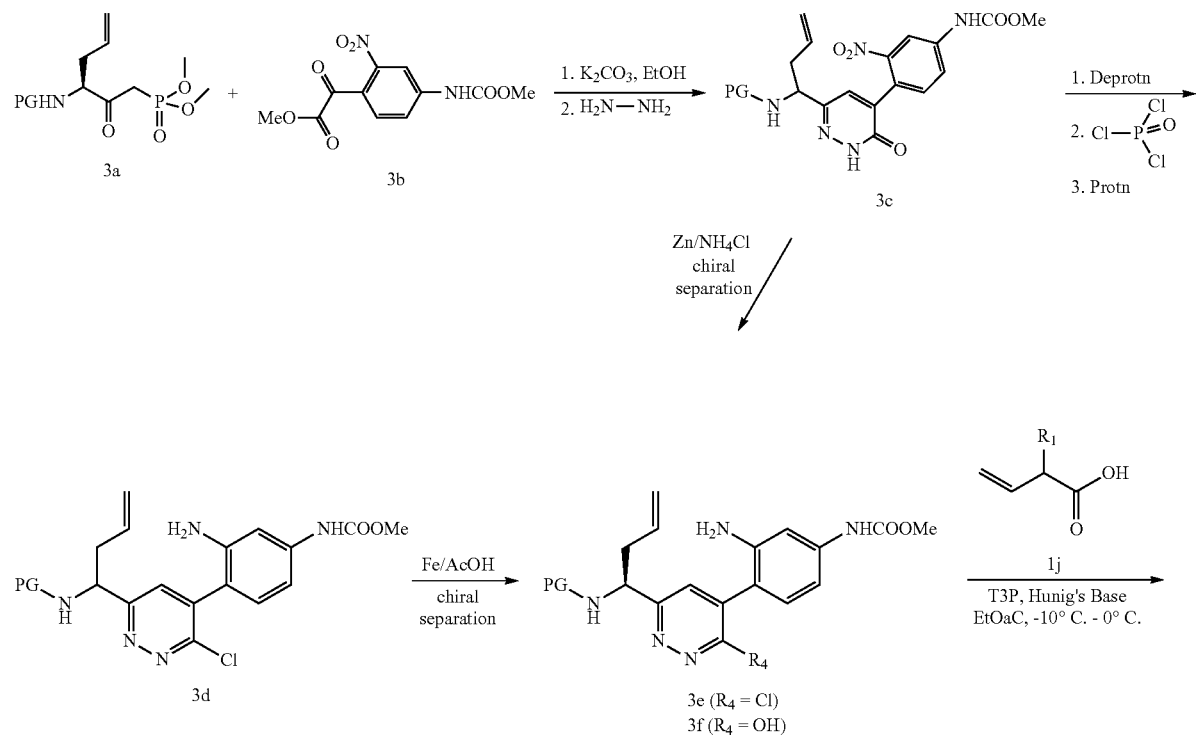

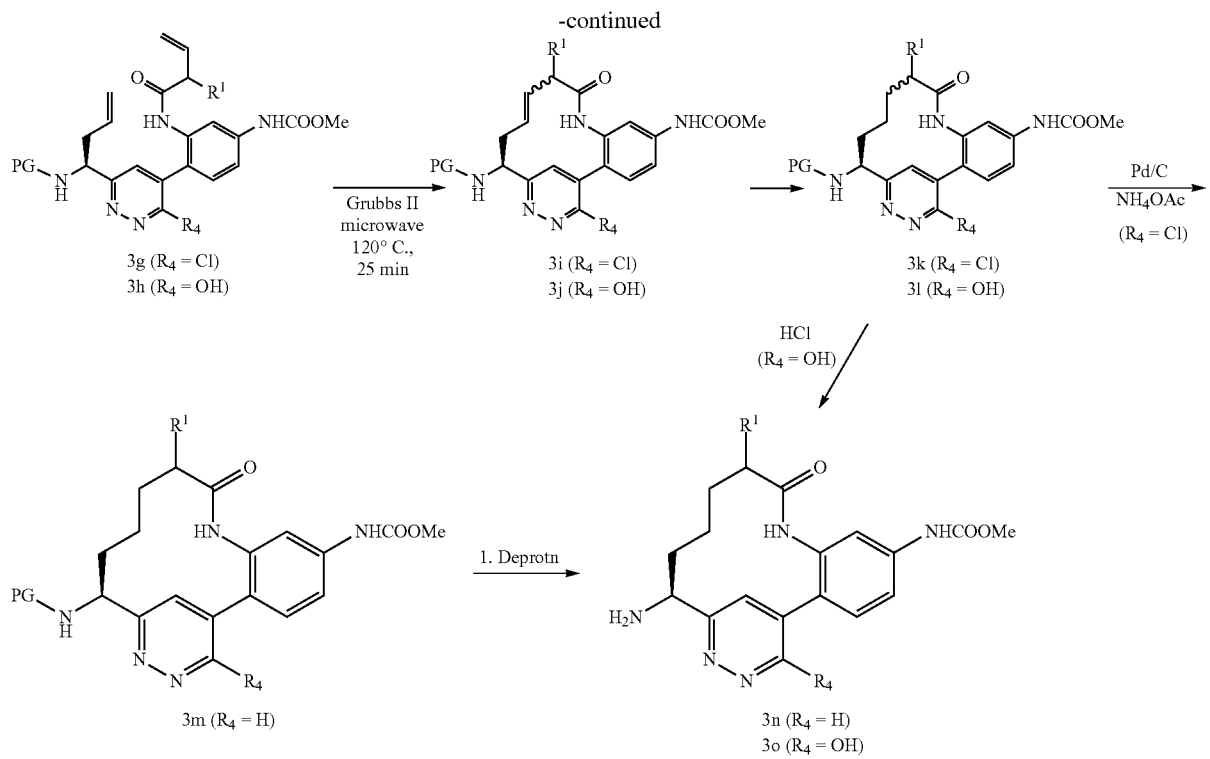

Intermediates for preparation of compounds of this invention wherein ring A is an imidazole ring, can be prepared from an appropriately N-protected allylglycine 4a according to the general method outlined in Scheme 4 (Contour-Galcera et al., *Bioorg. Med. Chem. Lett.*, 11(5):741-745 (2001)). Condensation of 4a with a suitably substituted bromoacetophenone 4b in the presence of a suitable base such as potassium bicarbonate, $K_2CO_3$ or $Cs_2CO_3$ in a suitable solvent such as DMF provides a keto ester intermediate which can be cyclized to afford an imidazole 4c by heating in the presence of excess ammonium acetate in a solvent such as toluene or xylene. This latter transformation can be conveniently carried out on small scale at 160° C. in a microwave reactor or on larger scale by refluxing the mixture while removing water via a Dean-Stark trap. The resulting imidazole intermediate 4c is then protected by treatment with SEM-Cl in the presence of a base such as sodium hydride or dicyclohexylmethylamine in a solvent such as THF or DCM. The nitro intermediate 4d is then converted to the corresponding aniline 4e by using Zn mediated reduction. Acylation of 4e with the appropriate alkenoic acid and a coupling agent such as T3P or BOP reagent, or alternately, by treatment with an alkenoic acid chloride in the presence of a base such as TEA of DIEA provides diene 4f, which undergoes ring closing metathesis by heating in dilute solution in the presence of p-toluene sulfonic acid and Grubbs II catalyst in a suitable solvent such as DCM or DCE to provide the corresponding macrocycle 4g (*Tetrahedron Letters*, 44:1379 (2003)). The alkene 4g can be reduced with hydrogen over either palladium on carbon or platinum oxide and subsequent deprotection with TFA in DCM provides amine 4h. Compounds of the formular 4h can be converted to compounds in this invention according to Scheme 6.

Scheme 4

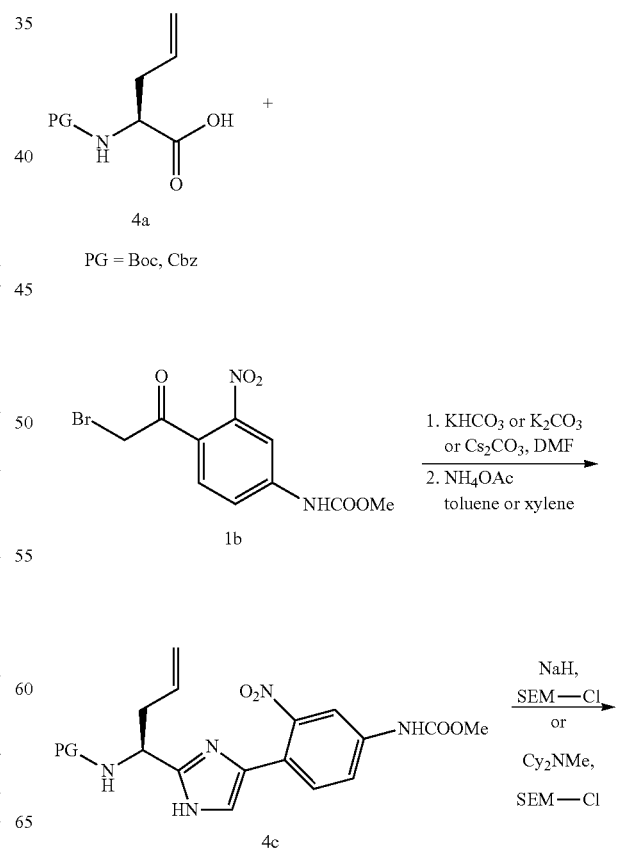

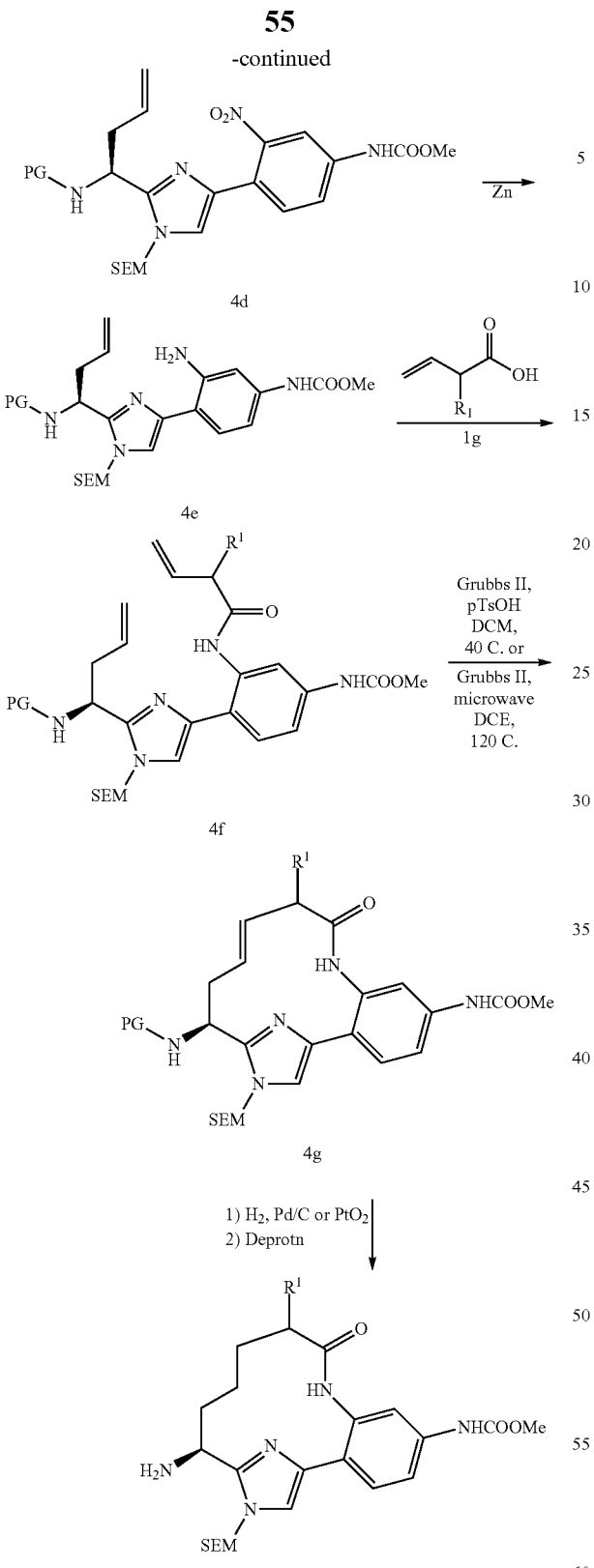

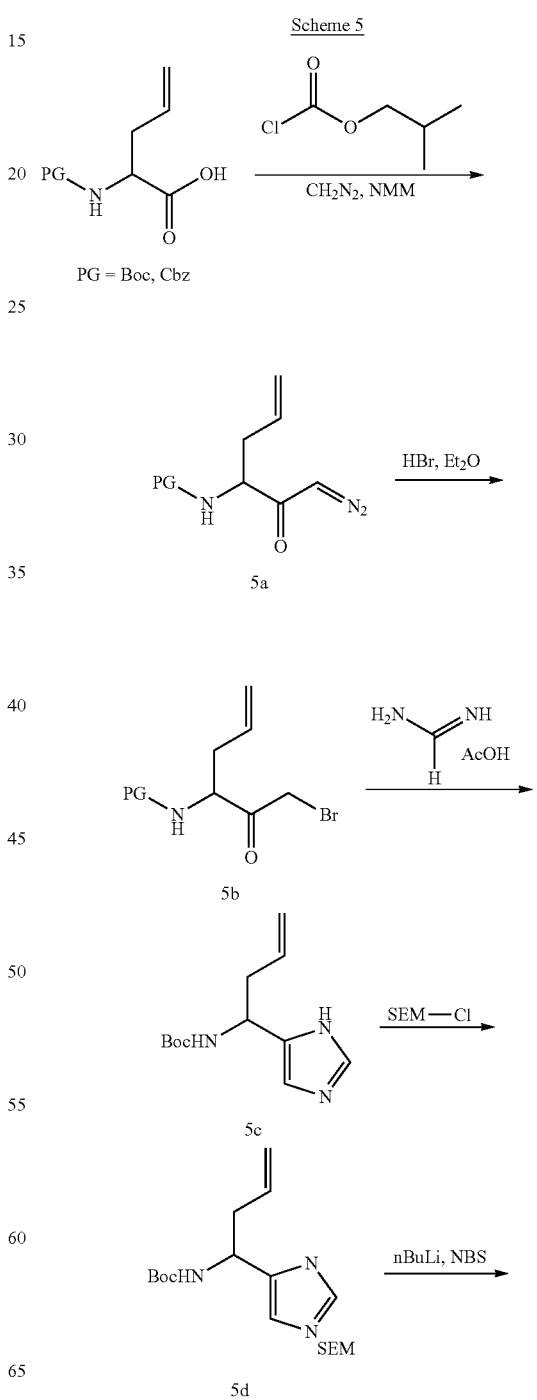

formamidine at elevated temperature generates the imidazole 5c. The imidazole 5c can be protected with SEM-Cl and then deprotonation with nBuLi and subsequent quenching with NBS provides the bromo imidazole 5e. Suzuki-Miyaura coupling between bromo imidazole 5e and an appropriately substituted aryl or heteroaryl boronic acid or ester in the presence of a base such as $K_3PO_4$ using a precatalyst such as Pd(dppf)$Cl_2 \cdot CH_2Cl_2$ complex provides, after separation of the enantiomers, aniline 5f. Aniline 5f can be converted to 5h according to Scheme 4. Compounds of the formulae 5h can be converted to compounds in this invention according to Scheme 6.

Representative regioisomeric imidazole containing amide macrocycle intermediates useful for the synthesis of compounds of this invention are described in Scheme 5. An appropriately N-protected allylglycine can be converted to the bromoketone 5b in two steps. Condensation of 5b with -continued

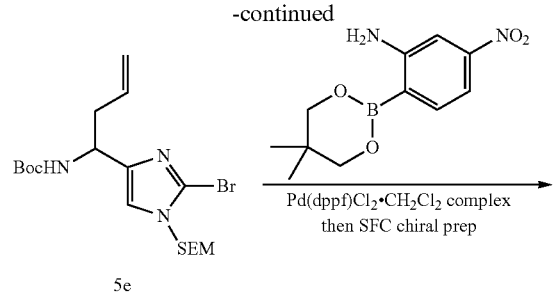

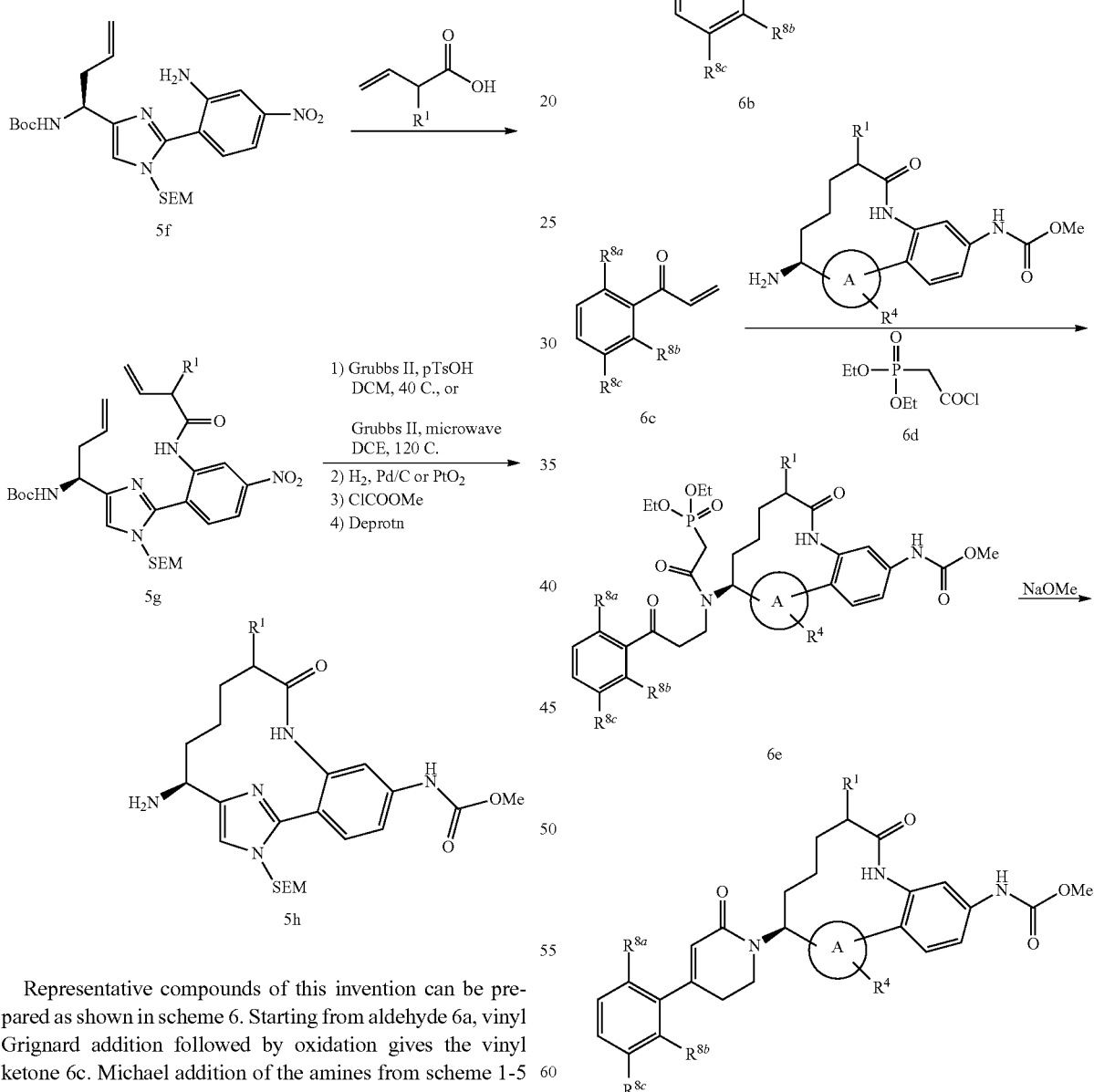

Scheme 6

Representative compounds of this invention can be prepared as shown in scheme 6. Starting from aldehyde 6a, vinyl Grignard addition followed by oxidation gives the vinyl ketone 6c. Michael addition of the amines from scheme 1-5 followed by acylation with 6d affords compounds 6e, which upon cyclization with base provides the dihydropyridone 6f. When ring A is an imidazole ring an additional deprotection step, using either TFA or HCl, is required to remove the SEM-protecting group in order to prepare imidazole-containing compounds of this invention.

Purification of intermediates and final products was carried out via either normal or reverse phase chromatography. Normal phase chromatography was carried out using pre-packed SiO2 cartridges eluting with either gradients of hexanes and ethyl acetate or DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% ACN, 0.1% TFA) and Solvent B (10% water, 90% ACN, 0.1% TFA, UV 220 nm) or with gradients of Solvent A (98% water, 2% ACN, 0.05% TFA) and Solvent B (98% ACN, 2% water, 0.05% TFA, UV 220 nm) (or) Sunfire Prep C18 OBD 5u 30×100 mm, 25 min gradient from 0-100% B. A=H$_2$O/ACN/TFA 90:10:0.1. B=ACN/H$_2$O/TFA 90:10:0.1

Unless otherwise stated, analysis of final products was carried out by reverse phase analytical HPLC.

Method A: A majority of analytical HPLC runs were: SunFire (4.6×150 mm) (15 min gradient—95:5 H$_2$O/ACN-to 95:5ACN/H$_2$O-0.05% TFA).

Method B: A minority of analytical HPLC runs were: Zorbax (4.6×75 mm) (8 min gradient—10:90 MeOH/H$_2$O to 90:10 MeOH/H$_2$O, 0.2% H$_3$PO$_4$).

Method C: Waters Acquity UPLC BEH C18, 2.1×50 mm, 1.7-mm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method D: Waters Acquity UPLC BEH C18, 2.1×50 mm, 1.7-mm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min A majority of mass spectra runs were: LCMS (ESI) m/z: [M+H]$^+$ Phenomenex Luna C18 (2×30 mm) (2 min gradient 90% H$_2$O/10% MeOH/0.1% TFA to 90% MeOH/10% H$_2$O/ 0.1% TFA) (or) BEH C18 2.1×50 mm-2 min gradient from 0-100% B. (A: 90/10/0.1H$_2$O/ACN/TFA; B: 90/10/0.1 ACN/H$_2$O/TFA).

Intermediate 1

1-(3-Chloro-2,6-difluorophenyl)prop-2-en-1-one

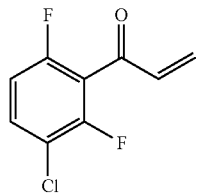

Intermediate 1A.
1-(3-Chloro-2,6-difluorophenyl)prop-2-en-1-ol

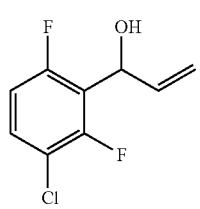

To a 100 mL dry round bottom flask containing vinylmagnesium bromide (1 M in THF) (24 mL, 24.00 mmol) under Ar at 0° C. was added 3-chloro-2,6-difluorobenzaldehyde (3.2 g, 18.13 mmol) in THF (10 mL) dropwise. The reaction was stirred for 1 h and quenched with 1 N HCl to pH 2. The mixture was extracted with Et$_2$O (3×). The combined organic layer was washed with brine, dried over MgSO$_4$, filtered, and concentrated to yield the desired product (3.71 g, 100%) as pale yellow oil. $^1$H NMR (500 MHz, CDCl$_3$) δ 7.34 (ddd, J=8.9, 8.1, 5.8 Hz, 1H), 6.90 (td, J=9.2, 1.7 Hz, 1H), 6.23 (dddt, J=17.2, 10.4, 5.8, 1.2 Hz, 1H), 5.60 (dd, J=7.6, 6.7 Hz, 1H), 5.40-5.31 (m, 1H), 5.28 (dt, J=10.2, 1.2 Hz, 1H), 2.38 (dt, J=8.3, 1.9 Hz, 1H).

Intermediate 1. To a solution of 1-(3-chloro-2,6-difluorophenyl)prop-2-en-1-ol (3.7 g, 18.08 mmol) in acetone (90 mL) at 0° C. was added Jones' reagent (8.77 ml, 23.51 mmol) dropwise. Upon finishing addition of Jones' reagent, the reaction was quenched with isopropanol. The mixture was concentrated. The residue was suspended in water and extracted with DCM (3×). The combined organic layer was washed with brine, dried over MgSO$_4$, filtered, and concentrated. The residue was purified by silica gel chromatography to yield the desired product as a yellow oil (3.45 g, 94%) which solidified in freezer. $^1$H NMR (500 MHz, CDCl$_3$) δ 7.48 (ddd, J=9.0, 8.0, 5.5 Hz, 1H), 7.05-6.91 (m, 1H), 6.70 (ddt, J=17.5, 10.5, 1.1 Hz, 1H), 6.29-6.11 (m, 2H).

Intermediate 2

1-(6-Bromo-3-chloro-2-fluorophenyl)prop-2-en-1-one

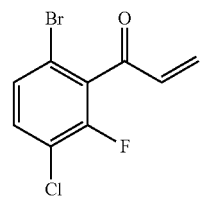

1-(6-Bromo-3-chloro-2-fluorophenyl)prop-2-en-1-one was prepared using a procedure analogous to intermediate 1 except that 3-chloro-2,6-difluorobenzaldehyde was replaced with 6-bromo-3-chloro-2-fluorobenzaldehyde. $^1$H NMR (500 MHz, CDCl$_3$) δ 7.33-7.41 (m, 2H), 6.64 (dd, J=17.6, 10.2 Hz, 1H), 6.25 (d, J=10.7 Hz, 1H), 6.07 (d, J=17.6 Hz, 1H).

Intermediate 3

Diethyl(2-chloro-2-oxoethyl)phosphonate

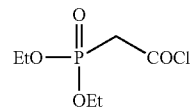

To a solution of 2-(diethoxyphosphoryl)acetic acid (0.1 mL, 0.622 mmol) in CH$_2$Cl$_2$ (1 mL) was added oxalyl dichloride (2 M in DCM) (0.622 mL, 1.244 mmol), followed by a drop of DMF. The reaction was stirred at rt for 2.5 h and concentrated in vacuo to yield the desired product as yellow oil. ¹H NMR (500 MHz, CHLOROFORM-d) δ 4.24 (dq, J=8.4, 7.1 Hz, 4H), 3.55-3.47 (d, J=21.46 Hz, 2H), 1.42-1.38 (t, J=7.4 Hz, 6H).

Intermediate 4

(R)-2-Methylbut-3-enoic acid

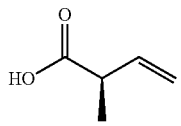

Intermediate 4A. (R)-4-Benzyl-3-((R)-2-methylbut-3-enoyl)oxazolidin-2-one: To the solution of 2-methylbut-3-enoic acid (5.59 g, 55.9 mmol) and N-methylmorpholine (6.14 ml, 55.9 mmol) in THF (62 mL) at 0° C. was added pivaloyl chloride (6.87 ml, 55.9 mmol) dropwise. The reaction mixture was cooled down to –78° C., and stirred for ~2 h. In a separate flask: To the solution of (R)-4-benzyloxazolidin-2-one (8.25 g, 46.6 mmol) in THF (126 mL) at –78° C. was added N-butyllithium (2.5 M in hexane) (20.49 mL, 51.2 mmol) dropwise. After 35 min, this reaction was transferred via cannula to the first reaction. The reaction mixture was stirred at –78° C. for 2 h, then the cold bath was removed, and the reaction was quenched with sat'd NH₄Cl. The reaction was diluted with water and extracted with EtOAc (3×). The combined organic layers were washed with brine, dried over Na₂SO₄, filtered, and concentrated to give a yellow oil (15 g). Purification by silica gel chromatography afforded the desired product (6.59 g, 55%) as a colorless oil. MS (ESI) m/z: 282.1 (M+Na)⁺. ¹H NMR (500 MHz, CDCl₃) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H). The other diastereomer (R)-4-benzyl-3-((S)-2-methylbut-3-enoyl)oxazolidin-2-one (4.6 g, 38%) also obtained as a white solid. MS (ESI) m/z: 260.1 (M+H)⁺.

Intermediate 4. (R)-2-Methylbut-3-enoic acid: To a clear colorless solution of Intermediate 4A (6.05 g, 23.33 mmol) in THF (146 mL) at 0° C. was added dropwise hydrogen peroxide (9.53 mL, 93 mmol) (30% aqueous) followed by 2 N lithium hydroxide (23.33 mL, 46.7 mmol). After 30 min, the reaction was quenched with 25 mL of sat'd Na₂SO₃ and 25 mL of sat'd NaHCO₃. The reaction was then concentrated to remove the THF. The residue was diluted with water and extracted with CHCl₃ (3×). The aqueous layer was acidified with conc. HCl to pH~3 and then it was extracted with EtOAc (3×). The EtOAc layers were combined, washed with brine, dried over MgSO₄, filtered and concentrated to afford the desired product (2.15 g, 92%) as a colorless oil. ¹H NMR (500 MHz, CDCl₃) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H).

Intermediate 5

(R)-2-methylbut-3-enoyl chloride

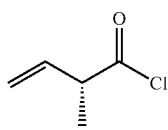

Intermediate 5. To a cooled (0° C.) solution of (R)-2-methylbut-3-enoic acid (0.450 g, 4.49 mmol) in DCM was added dropwise oxalyl chloride (0.393 ml, 4.49 mmol). The reaction mixture was stirred at 0° C. for 30 min and then it was allowed to stir at rt for 1.3 h. The resulting solution of (R)-2-methylbut-3-enoyl chloride was used directly.

Intermediate 6

2-(5,5-Dimethyl-1,3,2-dioxaborinan-2-yl)-5-nitrophenylamine

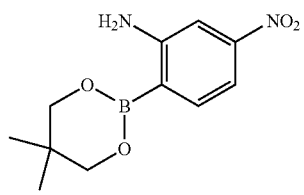 [SMILES: CC1(C)COB(c2ccc([N+](=O)[O-])cc2N)OC1]

To a flame-dried flask, equipped with a reflux condenser, containing 2-bromo-5-nitroaniline (10.0 g, 46.1 mmol), bis(neopentyl glycolato)diboron (13.01 g, 57.6 mmol), potassium acetate (13.57 g, 138 mmol), and PdCl₂(dppf)-CH₂Cl₂ adduct (0.941 g, 1.152 mmol) was added DMSO (132 mL). The resulting dark red-brown suspension was degassed with argon for 30 min and then the reaction was warmed to 80° C. After 4 h, the reaction was stopped and cooled to rt. The reaction was poured slowly into vigorously stirred ice-cold water (300 mL) to give a brown suspension. After stirring for 10 min, the suspension was filtered to collect the solid. The solid was rinsed with water (3×125 mL), air-dried, and then dried under a vacuum to give a brown solid. Purification by normal phase chromatography gave 4.36 g of Intermediate 6 as an orange solid. MS (ESI) m/z: 183.1 (M–C₅H₈+H)⁺.

Intermediate 7

Methyl 4-(2-bromoacetyl)-3-nitrophenylcarbamate

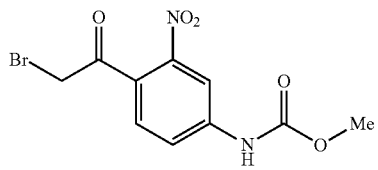 [SMILES: COC(=O)Nc1ccc(C(=O)CBr)c([N+](=O)[O-])c1]

Intermediate 7A. Methyl 4-iodo-3-nitrophenylcarbamate: To a cooled (0° C.), yellow suspension of 4-iodo-3-nitroaniline (8.46 g, 32.0 mmol) in DCM (320 mL) and pyridine (2.85 mL, 35.2 mmol) was added methyl chloroformate (2.61 mL, 33.6 mmol) dropwise. The reaction mixture turned to light yellow solution and stirring was continued for 1.5 h. After 1.5 h, the reaction mixture was diluted with DCM, washed with saturated NaHCO₃ solution followed by brine. The organic layers were dried over MgSO₄, filtered and concentrated to obtain a residue. The residue was then dissolved in DCM (~100 mL), then hexane (600 mL) was added to give a yellow suspension. The above suspension was filtered and the filtered solid was rinsed with hexane and air-dried to obtain the desired product as yellow solid (10.3 g, 100%). MS (ESI) m/z: 321.3 (M–H)⁺.

Intermediate 7B. Methyl 4-(1-ethoxyvinyl)-3-nitrophenyl-carbamate: A solution of Intermediate 7A (1 g, 3.11 mmol), tributyl(1-ethoxyvinyl)stannane (1.574 mL, 4.66 mmol), and bis(triphenylphosphine)palladium(II) chloride (0.109 g, 0.155 mmol) in toluene (6.21 mL) was heated at 110° C. for 2 h. After 2 h, the reaction was cooled to rt, filtered through a 0.45µ GMF filter and rinsed with EtOAc. The filtrate concentrated to dryness and purified by silica gel chromatography to obtain 9B as brown solid (0.56 g, 68%). MS (ESI) m/z: 267.3 (M+H)$^+$.

Intermediate 7. Methyl 4-(2-bromoacetyl)-3-nitrophenyl-carbamate: (Reference: *J. Med. Chem.*, 45:2127-2130 (2002)) To a solution of alternative Intermediate 7B (0.56 g, 2.103 mmol) in THF (3.12 mL) and water (1.091 mL) was added NBS (0.374 g, 2.103 mmol). After stirring at rt for 20 min, the reaction mixture was partitioned between EtOAc and brine. The organic layer was washed with brine, dried over Na$_2$SO$_4$, filtered, and concentrated to yield the desired product as yellow oil (0.667 g, 100%). MS (ESI) m/z: 317.2 (M+H)$^+$, 319.2 (M+2H)$^+$.

Example 1

Methyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA salt

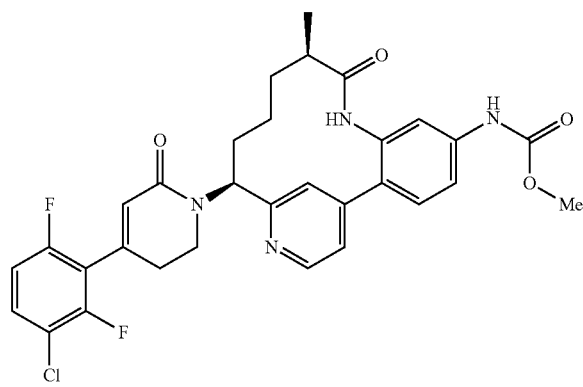 [SMILES: COC(=O)Nc1ccc2c(c1)NC(=O)[C@H](C)CCC[C@H](N1CCC(c3c(F)ccc(Cl)c3F)=CC1=O)c1cc-2ccn1]

1A. (S,E)-N-((4-Chloropyridin-2-yl)methylene)-2-methylpropane-2-sulfinamide: Liu, G. et al., *J. Org. Chem.*, 64:1278 (1999). To a solution of S-(−)-t-butyl-sulfinamide (0.856 g, 7.06 mmol) in dichloromethane (14.13 mL) was added sequentially copper(II) sulfate (2.481 g, 15.54 mmol) and 4-chloropicolinaldehyde [1.0 g, 7.06 mmol, prepared according to a modified described by Negi (*Synthesis*, 991 (1996))]. The white suspension was stirred at rt. After 3 h, the brown suspension was filtered through Celite®, eluting with DCM, to give a clear brown filtrate. Concentration gave a brown oil weighing 1.85 g. Purification by normal phase chromatography gave 1.31 g of 1A as a clear, yellow oil. MS (ESI) m/z: 245.0 (M+H)$^+$.

1B. (S)—N—((S)-1-(4-Chloropyridin-2-yl)but-3-enyl)-2-methylpropane-2-sulfinamide: To a cooled (0-5° C.) mixture of indium(III) chloride (13.56 g, 61.3 mmol) in tetrahydrofuran (170 mL) was added dropwise over 30 min. allylmagnesium bromide (1M in diethylether) (62 mL, 61.3 mmol). The reaction was allowed to warm to rt. After 1 h at rt, a solution of 1A (10 g, 40.9 mmol) in ethanol (170 mL) was added. After 2-3 h, the reaction was concentrated under vacuum at 50-55° C. The crude material was partitioned between ethyl acetate (200 ml) and water (1×50 ml) and the layers were separated. The aqueous layer was extracted with ethyl acetate (2×50 ml). The organic layers were combined and washed with brine (1×100 ml), dried over sodium sulfate, filtered and concentrated to give 1B (13.5 g, 106%) as a yellow oil. MS (ESI) m/z: 287.2 (M+H)+. This material was used in the next step without further purification.

1C. (S)-tert-butyl 1-(4-chloropyridin-2-yl)but-3-enylcarbamate: 1B (75 g, 261 mmol) was dissolved in methanol (1500 mL). Hydrochloric acid (6N) (750 ml, 4.5 mol) was added. The reaction was stirred at rt for 2-3 hrs and then was concentrated. The residue was diluted with water (2 L), washed with ethyl acetate (500 ml). The aqueous layer was basified with saturated sodium carbonate solution, extracted into ethyl acetate (3×1 L). The combined organic layers were washed with water (1×1 L) and brine (1×1 L), dried over sodium sulfate, filtered and conc. under vacuum at 50-55° C. to give crude product (43 g, 90%). MS (ESI) m/z: 183.2 (M+H)+. The crude product (42 g, 230 mmol) was dissolved in dichloromethane (420 mL), Et$_3$N (32.1 mL, 230 mmol) was added followed by dropwise addition of Boc$_2$O (53.4 mL, 230 mmol). The reaction was stirred at rt for 2-3 hrs. The reaction was diluted with excess DCM (1 L), washed with water (1×500 ml) and brine (1×500 ml). The organic layer was dried over sodium sulfate, filtered, and concentrated. The crude product was then purified using silica gel chromatography to give 1C (61 g, 86%) as a pale yellow solid. MS (ESI) m/z: 283.2 (M+H)$^+$.

1D. (S)-tert-Butyl 1-(4-(2-amino-4-nitrophenyl)pyridin-2-yl)but-3-enylcarbamate: To a RBF was added 1C (3.33 g, 11.78 mmol), intermediate 6 (5.89 g, 23.55 mmol), PdCl2 (dppf)-CH$_2$Cl$_2$ Adduct (0.962 g, 1.178 mmol), and potassium phosphate, tribasic (5.00 g, 23.55 mmol). The RBF was equipped with a reflux condensor then the apparatus was purged with argon for several minutes. Next, degassed DMSO (Volume: 58.9 ml) was added followed by degassed water (1.061 ml, 58.9 mmol). The bright orange suspension was warmed to 90° C. for 6 hrs and then it was cooled to rt and stirred overnight. The reaction was filtered via Buchner funnel, rinsing with EtOAc to remove the solid. The filtrate was then partitioned between EtOAc and water which gave an emulsion. Brine was added to break up the emulsion and the layers were separated. The aqueous layer was extracted with EtOAc (1×). The combined organic layers were washed with brine, dried over Na$_2$SO$_4$, filtered and concentrated to give a thick black oil weighing 10.2 g. Purification by column chromatography gave 1D as an orange foam (2.90 g, 64%). MS (ESI) 385.1 (M+H)+.

1E. (S)-tert-Butyl 1-(4-(2,4-diaminophenyl)pyridin-2-yl)but-3-enylcarbamate: To a clear, orange solution of 1D (2.9 g, 7.54 mmol) in methanol (75 mL) was added sequentially zinc dust (4.93 g, 75 mmol) and ammonium chloride (4.04 g, 75 mmol). The resulting suspension was stirred vigorously for 4 h. The reaction was yellow filtrate. Concentration of the filtrate gave a yellow-black residue. The residue was partitioned between EtOAc and 0.25 M HCl (50 mL) and the layers were separated. The organic layer was extracted with 0.25 M HCl (1×50 mL). The combined aqueous layers were basified with 1.5M K$_2$HPO$_4$ and then extracted with EtOAc (3×). The combined organic layers were washed with brine, dried over Na$_2$SO$_4$, filtered and concentrated to give 1E (2.63 g, 98%) as a brown foam. MS (ESI) m/z: 355.2 (M+H)$^+$.

1F. {3-Amino-4-[2-((S)-1-tert-butoxycarbonylamino-but-3-enyl)-pyridin-4-yl]-phenyl}-carbamic acid methyl ester: To a cooled (−78° C.) clear, brown solution of 1E (2.63 g, 7.42 mmol) and pyridine (0.600 ml, 7.42 mmol) in dichloromethane (74.2 ml) was added dropwise over 30 min methyl chloroformate (0.516 ml, 6.68 mmol). The reaction was stirred at −78° C. After 1.5 h, the reaction was quenched with sat. NH$_4$Cl and the reaction was allowed to warm to rt. The reaction was diluted with DCM and water and the layers were separated. The aqueous layer was extracted with DCM (1×). The combined organic layers were washed with sat. NaHCO$_3$, brine, dried over Na$_2$SO$_4$, filtered and concentrated. The residue dissolved in DCM (~10 mL) and then hexane (~300 mL) was added to give a brown suspension with brown gummy sticky substance at the bottom. The mixture was sonicated to give a mostly clear solution with the brown substance at the bottom. The solution decanted and the bottom substance rinsed with hexane, dried to give 1F (2.7 g, 88%) as a slightly brown foam. MS (ESI) m/z: 413.2 (M+H)$^+$.

1G. Methyl N-(4-{2-[(1S)-1-{[(tert-butoxy)carbonyl]amino}but-3-en-1-yl]pyridin-4-yl}-3-[2R]-2-methylbut-3-enamido]phenyl)carbamate: Intermediate 4 (1.201 g, 12.00 mmol), 1F (3.3 g, 8.00 mmol), pyridine (1.937 ml, 24.00 mmol) in EtOAc (40.0 ml) was cooled down to −10° C. under Ar, T3P (50% wt in EtOAc) (9.52 ml, 16.00 mmol) was added dropwise and stirred at −10° C., then gradually warmed up to rt over night. The reaction mixture was washed with conc. NaHCO$_3$ aq twice, combined aqueous layer was back extracted with EtOAc. The combined EtOAc phases washed with brine, dried over MgSO$_4$, filtered, concentrated. The crude product was then purified using silica gel chromatography to give 1G (4.06 g, 97%) as a white solid. $^1$H NMR (500 MHz, METHANOL-d$_4$) δ 8.46 (d, J=5.0 Hz, 1H), 7.64 (s, 1H), 7.47 (dd, J=8.4, 2.1 Hz, 1H), 7.35 (s, 1H), 7.29 (d, J=8.3 Hz, 1H), 7.25 (m, 1H), 5.87-5.73 (m, 2H), 5.16-5.02 (m, 4H), 4.79-4.71 (m, 1H), 3.75 (s, 3H), 3.14-3.05 (m, 1H), 2.64-2.55 (m, 1H), 2.52-2.43 (m, 1H), 1.42 (s, 9H), 1.16 (d, J=6.9 Hz, 3H). MS (ESI) m/z: 495.1 (M+H)$^+$.

1H. Methyl N-[(10R,11E,14S)-14-{[(tert-butoxy)carbonyl]amino}-10-methyl-9-oxo-8,16-diazatricyclo[13.3.1.0$^{2,7}$]nonadeca-1(19),2(7),3,5,11,15,17-heptaen-5-yl]carbamate: To a RBF was added 1G (0.5 g, 1.011 mmol), pTsOH monohydrate (0.212 g, 1.112 mmol), and dichloromethane (84 ml). The flask was equipped with a reflux condensor and the clear yellow solution was degassed with argon for 30 min. The reaction was then warmed to reflux for 1 h. Then a solution of Grubbs II (0.172 g, 0.202 mmol) in DCM (2 mL) was added dropwise to the reaction mixture. After 4 h at reflux, the reaction was cooled to rt, washed with sat. Na$_2$CO$_3$, brine, dried over MgSO$_4$, filtered, and concentrated to give a brown solid. The crude product was then purified using silica gel chromatography to give 1H (0.336 g, 71.2% yield) as a yellow solid. $^1$H NMR (500 MHz, METHANOL-d$_4$) δ 8.52 (d, J=5.2 Hz, 1H), 7.54 (d, J=1.4 Hz, 1H), 7.48-7.43 (m, 1H), 7.38 (d, J=8.3 Hz, 1H), 7.24 (dd, J=5.1, 1.5 Hz, 1H), 6.89 (s, 1H), 5.75-5.65 (m, 1H), 4.60 (dd, J=11.3, 3.6 Hz, 1H), 4.39 (dd, J=15.1, 9.6 Hz, 1H), 3.75 (s, 3H), 3.14-3.06 (m, 1H), 2.75-2.68 (m, 1H), 2.04-1.94 (m, 1H), 1.44 (s, 9H), 1.30 (br. s., 1H), 1.04 (d, J=6.6 Hz, 3H). MS (ESI) m/z: 467.2 (M+H)$^+$.

1I. Methyl N-[(10R,14S)-14-{[(tert-butoxy)carbonyl]amino}-10-methyl-9-oxo-8,16-diazatricyclo[13.3.1.0$^{2,7}$]nonadeca-1(19),2(7),3,5,15,17-hexaen-5-yl]carbamate:1H was dissolved in 200 ml MeOH, vacuumed and refilled with Ar, Pd/C (10% wt) (0.684 g, 0.643 mmol) was added, vacuumed and refilled with Ar, then vacuumed and refilled with H$_2$ 3 times, stirred at rt under 55 psi H$_2$ for 16 hrs. Reaction mixture was filtered off solid through a pad of celite under N$_2$, washed with copious of MeOH, the resulting dark filtrate was further filtered through 6× whatman autovials and 6× target2 nylon 0.2 μM syringe filters under N$_2$ to yield a colorless clear solution, which was concentrated under vacuum to afford 1I (3 g, 6.4 mmol, 100% yield) as a white solid. $^1$H NMR (500 MHz, DMSO-d$_6$) δ 9.87 (s, 1H), 9.65 (s, 1H), 8.54 (d, J=5.0 Hz, 1H), 7.50-7.43 (m, 2H), 7.40 (s, 1H), 7.33 (s, 1H), 7.23 (dd, J=5.0, 1.7 Hz, 1H), 7.03 (d, J=7.4 Hz, 1H), 4.65-4.55 (m, 1H), 3.69 (s, 3H), 2.60 (br. s., 1H), 1.84-1.55 (m, 3H), 1.34 (s, 9H), 1.21-1.06 (m, 2H), 0.79 (d, J=7.2 Hz, 3H), 0.11 (d, J=12.1 Hz, 1H). MS (ESI) m/z: 469.0 (M+H)$^+$.

1J. Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, TFA salt: 1I (3 g, 6.40 mmol) in CH$_2$Cl$_2$ (100 mL) was added TFA (14.80 mL, 192 mmol). After 4 hrs, reaction mixture was concentrated under vacuum to afford 1J as a yellow solid (3.8 g, 6.4 mmol). MS (ESI) m/z: 369.0 (M+H)$^+$.

1J. (Alternative, 2HCl): Methyl N-[(10R,14S)-14-amino-10-methyl-9-oxo-8,16-diazatricyclo[13.3.1.0$^{2,7}$]nonadeca-1(19),2(7),3,5,15,17-hexaen-5-yl]carbamate, 2HCl salt: To a flask containing 1I (0.880 g, 1.878 mmol) was added 4.0 M HCl in dioxane (21.13 ml, 85 mmol). The resulting suspension was sonicated to give a clear, yellow solution. After 5 to 10 min, a precipitate formed. After 1 h, the reaction was stopped and the precipitate was collected by filtration. The solid was rinsed with dioxane and air-dried to give a hygroscopic, yellow solid. The solid was dissolved in methanol, concentrated, and lyophilized to give 1J (Alternative, 2HCl) (0.7171 g, 87%) as a yellow solid. MS (ESI) m/z: 369.3 (M+H)$^+$.

1K. Methyl N-[(10R,14S)-14-{N-[3-(3-chloro-2,6-difluorophenyl)-3-oxopropyl]-2-(diethoxyphosphoryl)acetamido}-10-methyl-9-oxo-8,16-diazatricyclo[13.3.1.0$^{2,7}$]nonadeca-1(18),2,4,6,15(19),16-hexaen-5-yl]carbamate: 1J (3.82 g, 6.4 mmol) in CH$_2$Cl$_2$ (160 ml) was added DIEA (6.71 ml, 38.4 mmol), sonicated thoroughly. Reaction was stirred at rt for a further 30 mins, intermediate 1 (1.3 g, 6.4 mmol) was added, stirred at rt. After 3 hrs, reaction mixture was cooled down to 0° C. under N$_2$, intermediate 3 (3.02 g, 14.08 mmol) in 5 ml DCM was added dropwise. After 15 mins, conc. NH$_4$Cl aq was added to quench reaction. DCM phase was separated and washed with 100 ml×10 aq NaHCO$_3$, followed by brine, dried over MgSO$_4$, filtered, concentrated under vacuum to yield a pale yellow solid crude product. The residue was purified by silica gel chromatography to yield 1K as an off white solid (3.84 g, 4.87 mmol, 76%). MS (ESI) m/z: 749.2 (M+H)$^+$.

Example 1

Methyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate 1K (3.36 g, 4.49 mmol) in MeOH (74.8 ml) was cooled down to 0° C. under N$_2$. Sodium methoxide (25% wt in MeOH) (3.88 g, 17.94 mmol) diluted in 10 ml MeOH was added dropwise via syringe pump. After 10 mins, reaction mixture was quenched with HCl (1N in aq) (13.46 ml, 13.46 mmol) at 0° C., then concentrated under vacuum to remove MeOH to yield a white slurry solution, which was added 450 ml DCM. The mixture was partitioned. DCM phase was further washed with 4×75 ml concentrated NaHCO$_3$ aq, then with brine; DCM phase was separated.

Concentrated under vacuum to a small volume, filtered and the white solid was rinsed with 5 ml mixture of MeOH and DCM. The collected white solid was dried under vacuum. The filtrate was concentrated under vacuum and filtered, rinsed with MeOH and DCM. Repeating the sequence twice, to collect example 1 (2.4 g, 4 mmol, 88%) as white solid product. $^1$H NMR (500 MHz, DMSO-$d_6$) δ 9.89 (s, 1H), 9.70 (s, 1H), 8.61 (d, J=5.0 Hz, 1H), 7.68 (m, 1H), 7.54-7.45 (m, 3H), 7.37 (s, 1H), 7.33-7.22 (m, 2H), 6.05 (s, 1H), 5.60 (dd, J=12.5, 4.5 Hz, 1H), 3.97 (br. s., 1H), 3.75-3.64 (m, 4H), 2.67-2.54 (m, 3H), 2.11-2.00 (m, 1H), 1.92 (br. s., 1H), 1.73-1.61 (m, 1H), 1.50-1.38 (m, 1H), 1.31-1.16 (m, 1H), 0.88 (d, J=6.9 Hz, 3H), 0.54 (br. s., 1H). MS (ESI) m/z: 595.0 (M+H)$^+$. Analytical HPLC (method A): RT=7.3 min, purity=99%.

Example 2

Methyl N-[(10R,14S)-14-[4-(6-bromo-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate

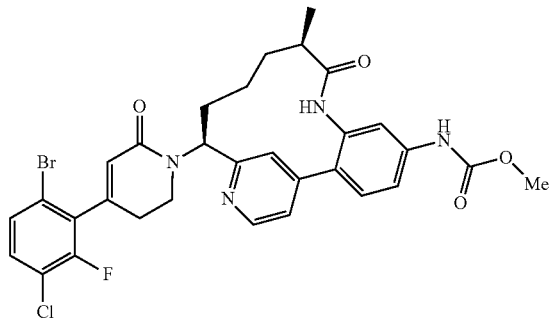 [SMILES: COC(=O)Nc1ccc2c(c1)NC(=O)[C@H](C)CCC[C@H](N1CCC(c3c(Br)ccc(Cl)c3F)=CC1=O)c1cc-2ccn1]

Example 2 was prepared using a procedure analogous to example 1 except that intermediate 1 was replaced with intermediate 2. $^1$H NMR (500 MHz, MeOD) δ 8.56-8.68 (m, 1H), 7.34-7.67 (m, 8H), 5.92 (br. s., 1H), 5.57-5.71 (m, 1H), 3.89-4.01 (m, 1H), 3.71-3.84 (m, 4H), 2.51-2.68 (m, 3H), 2.10-2.29 (m, 1H), 1.80-2.01 (m, 2H), 1.48-1.63 (m, 1H), 1.04 (d, J=6.3 Hz, 3H), 0.86-0.94 (m, 2H). MS (ESI) m/z: 657.0 (M+H)$^+$. Analytical HPLC (method A): RT=8.1 min, purity=98%.

Example 3

Methyl N-[(10R,14S)-14-[4-(3-chloro-2,6-difluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate, TFA salt

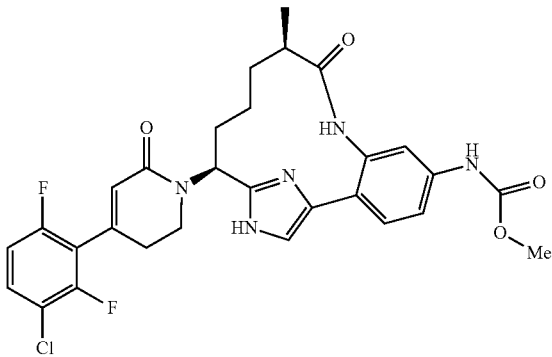 [SMILES: COC(=O)Nc1ccc2c(c1)NC(=O)[C@H](C)CCC[C@H](N1CCC(c3c(F)ccc(Cl)c3F)=CC1=O)c1nc-2c[nH]1]

3A. (S)-2-(4-(Methoxycarbonylamino)-2-nitrophenyl)-2-oxoethyl 2-(tert-butoxycarbonylamino)pent-4-enoate: To a clear, colorless solution of (S)-2-(tert-butoxycarbonylamino)pent-4-enoic acid (2.91 g, 13.50 mmol) in DMF (33.7 mL) was added potassium hydrogen carbonate (1.622 g, 16.20 mmol). The reaction mixture was stirred for 20 min at rt and then cooled to 0° C. To the above mixture was then added a solution of Intermediate 7 (4.28 g, 13.50 mmol) in DMF (33.7 mL) dropwise and the reaction was allowed to warm to rt and continued to stir at rt for overnight. After 18 h, the reaction was stopped and cooled to 0° C. The reaction mixture was then poured into ice-cold water, then extracted with EtOAc (3×). The combined organic layers were washed with water, brine, dried over Na$_2$SO$_4$, filtered and concentrated. A yellow foam obtained as 3A (6.09 g, 100%). MS (ESI) m/z: 450.5 (M−H)$^+$.

3B. Methyl(4-(2-((1S)-1-((tert-butoxycarbonyl)amino)but-3-en-1-yl)-1H-imidazol-5-yl)-3-nitrophenyl)carbamate: To a 1000 mL RBF containing 3A (6.09 g, 13.49 mmol) was added xylene (135 mL). The above mixture was sonicated to obtain a clear yellow solution. To the clear yellow solution was then added ammonium acetate (10.40 g, 135 mmol) and the flask was equipped with a Dean-stark trap and a reflux condenser. The reaction was warmed to 110° C. for 2 h, and then 140° C. for 2 h. After stirring for 4 hours in total, the reaction was allowed to cool to rt. The reaction was diluted with EtOAc and then washed with saturated NaHCO$_3$ solution (2×) followed by brine. The organic layers were then dried over Na$_2$SO$_4$, filtered, and concentrated. The brown gum weighing 5 g was dissolved in DCM and a small amount of MeOH and then purified using silica gel chromatography. A brown foam obtained as 3B (0.91 g, 15.6%). MS (ESI) m/z: 432.5 (M+H)$^+$.

3C. Methyl(4-(2-((1S)-1-((tert-butoxycarbonyl)amino)but-3-en-1-yl)-1-((2-(trimethylsilyl)ethoxy)methyl)-1H-imidazol-4-yl)-3-nitrophenyl)carbamate: A flame-dried 25 mL round bottom flask was charged with NaH (0.092 g, 2.295 mmol) and then THF (4.17 mL) was added to give a gray suspension. The suspension was cooled to 0° C. and then a clear, yellow solution of 3B (0.9 g, 2.086 mmol) in THF (4.17 mL) was added dropwise. The reaction mixture was stirred at 0° C. for 30 min and then allowed to warm to rt and stirring was continued at rt for additional 0.5 h. The yellow suspension was again cooled to 0° C. and then SEM-Cl (0.370 mL, 2.086 mmol) was added dropwise. The resulting cloudy reaction mixture was stirred at 0° C. After 1 h, the reaction was stopped and quenched with saturated NH$_4$Cl followed by dilution with EtOAc. The layers were separated and the aqueous layer was extracted with EtOAc. The combined organic layers were washed with saturated NaHCO$_3$, brine, dried over Na$_2$SO$_4$, filtered, and concentrated. The yellow oil weighing 1.6 g was purified by silica gel chromatography. The desired product from the reaction was obtained as yellow foam (0.424 g, 36%). MS (ESI) m/z: 562.0 (M+H)$^+$. 1D NOE confirmed the regioisomeric position of SEM on the imidazole ring.

3D. tert-Butyl N-[(1S)-1-(4-{2-amino-4-[(methoxycarbonyl)amino]phenyl}-1-{[2-(trimethylsilyl)ethoxy]methyl}-1H-imidazol-2-yl)but-3-en-1-yl]carbamate: To the solution of 3C (0.424 g, 0.755 mmol) in MeOH (5 mL) was added zinc (0.494 g, 7.55 mmol) and ammonium chloride (0.404 g, 7.55 mmol). The reaction mixture was stirred at 60° C. in a sealed tube. After 4 h, the reaction was cooled to rt. The yellow suspension was diluted with DCM and then washed with water. The aqueous layer extracted with 15% IPA/CHCl$_3$. The combined organic layers were washed with brine, dried over MgSO$_4$, filtered and concentrated. The crude product was purified using silica gel chromatography to give an orange solid as the desired product (0.31 g, 77%). MS (ESI) m/z: 532.4 (M+H)$^+$.

3E. tert-butyl N-[(1S)-1-(4-{4-[(methoxycarbonyl)amino]-2-[(2R)-2-methylbut-3-enamido]phenyl}-1-{[2-(trimethylsilyl)ethoxy]methyl}-1H-imidazol-2-yl)but-3-en-1-yl]carbamate: To a cooled (0° C.), clear yellow orange solution of 3D (4.83 g, 9.08 mmol) in ethyl acetate (91 ml) was added Intermediate 4 (1.0 g, 9.99 mmol) and Hunig's base (6.34 ml, 36.3 mmol). Next, 1-propanephosphonic acid cyclic anhydride (T3P) (50% in EtOAc) (13.38 ml, 22.70 mmol) was added dropwise over 20 min. and the reaction was stirred at 0° C. After 3 h, the reaction was diluted with EtOAc and washed with sat. NaHCO$_3$. The aqueous layer was extracted with EtOAc (2×). The organic layers were combined and washed with brine, dried over sodium sulfate, filtered and concentrated to give an orange foam. Purification by normal phase chromatography gave 6E (4.53 g, 81% yield) as a white foam. Proton NMR indicated a 3:1 mixture of diastereomers. MS (ESI) m/z: 614.4 (M+H)$^+$.

3E. tert-butyl N-[(10R,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer A) and 6F. tert-butyl N-[(10S,11E,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,11,15(18)-hexaen-14-yl]carbamate (Diastereomer B): To a solution of 3D (4.40 g, 7.17 mmol) in dichloromethane (717 ml) was added pTsOH monohydrate (1.523 g, 7.89 mmol) and the mixture was degassed with argon for 30 min. Next, the flask was equipped with a reflux condensor and the reaction was warmed to 40° C. for 1 h. Next, a burgundy solution of Grubbs II (2.440 g, 2.87 mmol) in 20 ml of DCM (degassed with argon) was added dropwise via syringe over 35 to 40 min. After 21.5 h, the reaction was cooled to rt. The reaction mixture was washed with sat. NaHCO$_3$, brine, dried over MgSO$_4$, filtered and concentrated to give a brown foam. Purification by normal phase chromatography gave 3E, Diastereomer A (1.71 g, 40.7% yield) as an off-white solid and a mixture of 3E (Diastereomer A) and 3F (Diastereomer B) (1.4 g). MS (ESI) m/z: 586.3 (M+H)$^+$.

3G. tert-butyl N-[(10R,14S)-5-[(methoxycarbonyl)amino]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-14-yl]carbamate: A dark brown solution of 3E (1.71 g, 2.92 mmol) in EtOAc (97 ml) was degassed with argon for 30 minutes. Next, platinum(IV) oxide (0.066 g, 0.292 mmol) was added and hydrogen gas from a balloon was bubbled through the reaction mixture for several minutes. The reaction was stirred under a hydrogen atmosphere. After 24 h, an additional amount of platinum(IV) oxide (0.192 g, 0.876 mmol) was added and the reaction was stirred under a hydrogen atmosphere. After 21 h, the reaction was stopped. The vessel was purged with vacuum/argon three times, then Celite was added, and the reaction was filtered rinsing with EtOAc. The resulting clear, yellow brown filtrate was concentrated to give an off-white solid weighing 1.66 g. Recrystallization from methanol (30 mL) gave 3G (0.575 g, 33.5% yield) as a white solid. MS (ESI) m/z: 588.4 (M+H)+.

3H. Methyl N-[(10R,14S)-14-[4-(3-chloro-2,6-difluorophenyl)-6-oxo-1,2,3,6 tetrahydropyridin-1-yl]-10-methyl-9-oxo-16-{[2-(trimethylsilyl)ethoxy]methyl}-8,16,18-triazatricyclo[13.2.1.0$^{2,7}$]octadeca-1(17),2,4,6,15(18)-pentaen-5-yl]carbamate: 3H was prepared in a similar way as example 1 except 1I was replaced with 3G.

Example 3. In a 1 dram vial, 3H (6.5 mg, 9.10 µmol) in HCl (4M in Dioxane) (0.3 mL, 1.200 mmol) was sealed and heated at 75° C. After 2.5 hr, the reaction mixture was cooled down to rt, concentrated under vacuum to remove solvent. Purification by reverse phase HPLC yield example 6 as pale yellow solid product (4.57 mg, 68%). $^1$H NMR (500 MHz, METHANOL-d$_4$) δ 7.64-7.51 (m, 4H), 7.46 (dd, J=8.5, 2.2 Hz, 1H), 7.15 (td, J=9.3, 1.8 Hz, 1H), 6.15 (s, 1H), 5.47 (dd, J=11.4, 6.2 Hz, 1H), 3.94-3.87 (m, 1H), 3.86-3.81 (m, 1H), 3.79 (s, 3H), 3.05-2.93 (m, 1H), 2.90-2.80 (m, 1H), 2.80-2.71 (m, 1H), 2.42-2.31 (m, 1H), 2.15 (m, 1H), 1.88-1.75 (m, 1H), 1.71-1.59 (m, 1H), 1.60-1.50 (m, 1H), 1.08 (d, J=6.9 Hz, 3H), 0.80 (br. s., 1H). MS (ESI) m/z: 584.1 (M+H)$^+$. Analytical HPLC (method A): RT=6.3 min, purity=95%.

Example 4

Methyl N-[(10R,14S)-14-[4-(3-chloro-2,6-difluorophenyl)-6-oxo-1,2,3,6-tetrahydropyridin-1-yl]-10-methyl-9-oxo-8,16,17-triazatricyclo[13.3.1.0$^{2,7}$]nonadeca-1(19),2,4,6,15,17-hexaen-5-yl]carbamate, TFA salt

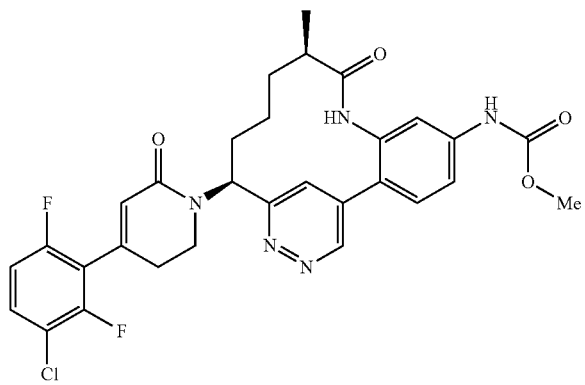

4A. (S)-tert-Butyl 1-(dimethoxyphosphoryl)-2-oxohex-5-en-3-ylcarbamate: To a solution of dimethyl methylphosphonate (15.85 mL, 148 mmol) in THF (99 mL) at −78° C. was added n-butyllithium (93 mL, 148 mmol) slowly. After addition was completed, the reaction mixture was stirred for 30 min and then a solution of (S)-methyl 2-(tert-butoxycarbonylamino)pent-4-enoate (6.8 g, 29.7 mmol) in THF (15 mL) was added slowly. Stirring was continued for another 40 min at −78° C. The reaction was then quenched by adding water and diluted with EtOAc. The organic layer was washed with 1 M HCl, saturated NaHCO$_3$ and brine. The organic layer was then dried over MgSO$_4$, filtered and concentrated to give a clear oil. The crude product was then purified by silica gel chromatography to give the desired product (9.3 g, 98%) as colorless oil. MS (ESI) m/z: 599.0 (M+Na)$^+$.

4B. Methyl 4-iodo-3-nitrophenylcarbamate: To a solution of 4-iodo-3-nitroaniline (1.320 g, 5 mmol) in DCM (50 mL) and pyridine (0.445 mL, 5.50 mmol) at 0° C. was added methyl chloroformate (0.407 mL, 5.25 mmol) dropwise. After stirring at 0° C. for 3 h, HPLC analysis showed the reaction to be complete. The reaction was then diluted with DCM, washed with brine and dried over $MgSO_4$ to yield the crude product. The crude product was then dissolved in minimal DCM (~20 mL) and hexane (200 mL) was added to give a yellow suspension. The suspension was filtered and the collected solid was rinsed with hexane and air-dried to obtain a yellow solid 4B (1.51 g, 94%). MS (ESI) m/z: 322.9 $(M+H)^+$.

4C. Methyl 4-acetyl-3-nitrophenylcarbamate: A solution of 4B (0.5 g, 1.553 mmol), tributyl(1-ethoxyvinyl)stannane (1.049 mL, 3.11 mmol), and bis(triphenylphosphine)palladium (II) chloride (0.109 g, 0.155 mmol) in toluene (3 mL) was heated at 110° C. for 3 h in a sealed tube. After 3 h, the reaction mixture was cooled to rt and concentrated to yield a residue. The residue was dissolved in THF (3 mL), followed by addition of 1 N HCl solution (5 mmol). The mixture was stirred at rt for 1 h and then diluted with EtOAc. The organic layer was then washed with brine and dried over $Na_2SO_4$ to give the crude product which was purified by silica gel chromatography to obtain 4C (0.254 g, 69%) as a yellow solid. MS (ESI) m/z: 239.3 $(M+H)^+$.

4D. 2-(4-((Methoxycarbonyl)amino)-2-nitrophenyl)-2-oxoacetic acid: To a solution of 4C (11.5 g, 48.3 mmol) in pyridine (48.3 mL) was added selenium dioxide (8.04 g, 72.4 mmol) in portions. After completion of addition, the reaction mixture was stirred under argon at 60° C. overnight. After stirring overnight, the solvent was evaporated and the resulting residue was further dried under vacuum for several hours to make sure most pyridine was removed. To the residue was added 1.0 N HCl (80 mL) and the resulting solution was filtered to obtain a grayish solid which was dried in a vacuum-oven at 45° C. overnight. To the dried solid was then added MeOH (200 mL) and filtered the suspension. The filtrate was concentrated to give a brownish foam 4D (11.8 g, 79%). MS (ESI) m/z: 269.0 $(M+H)^+$.

4E. Methyl 2-(4-((methoxycarbonyl)amino)-2-nitrophenyl)-2-oxoacetate: To a red oil of 4D (11.8 g, 38.3 mmol) in DCM (150 mL) at 0° C. was added TEA (7.47 mL, 53.6 mmol) and sonicated the mixture to dissolve into a complete solution. Methyl carbonochloridate (4.15 mL, 53.6 mmol) was added dropwise at 0° C. to the above mixture. After 20 min, the reaction mixture was diluted with DCM (300 mL), washed with 1 N HCl, saturated $NaHCO_3$ solution and brine. The organic layer was dried over $MgSO_4$, filtered and concentrated to give a red colored solid. The crude product was then purified by silica gel chromatography to yield 4E (8.6 g, 80%) as a light grayish powder. MS (ESI) m/z: 283.0 $(M+H)^+$.

4F. Methyl(4-(6-((1S)-1-((tert-butoxycarbonyl)amino)but-3-en-1-yl)-3-oxo-2,3-dihydropyridazin-4-yl)-3-nitrophenyl)carbamate: To a clear solution of 4A (1.16 g, 3.61 mmol) in EtOH (38.4 mL) at rt was added $K_2CO_3$ (0.748 g, 5.42 mmol). The reaction mixture was then stirred at rt for 2 h. After stirring for 2 h at rt, the reaction mixture was concentrated to remove the solvent followed by vacuum drying for 1 h to yield a solid. To this solid was added THF (30 mL), followed by the addition of a suspension of 4E (1.121 g, 3.97 mmol) in 8 mL of THF dropwise via an addition funnel. After 3 h, hydrazine (0.567 mL, 18.05 mmol) was added and the reaction was stirred at rt for 4 days. The reaction mixture was then diluted with EtOAc and washed with 1 N HCl followed by brine. The organic layers were then dried over $MgSO_4$ and concentrated to give the crude product that was purified by silica gel chromatography to give 4F (0.48 g, 29%) as light orange solid. MS (ESI) m/z: 460.0 $(M+H)^+$.

4G. (S)-Methyl(4-(6-(1-aminobut-3-en-1-yl)-3-chloropyridazin-4-yl)-3-nitrophenyl)carbmate: To a solution of 4F (2.2 g, 4.79 mmol) in MeOH (23.94 mL) was added HCl (4 M in dioxane) (5.186 mL, 20.74 mmol) and stirred at rt for 6 h. The reaction mixture was then concentrated to yield a brownish solid. To the brownish solid was then added $CH_3CN$ (23.94 mL) and phosphoryl trichloride (13.39 mL, 144 mmol), and the reaction mixture was heated at 80° C. overnight. The reaction mixture was concentrated and dried under vacuum overnight. The crude mixture was cooled to 0° C. and the reaction was then quenched by the addition of 1 N HCl (20 mL). The reaction mixture was neutralized with 1 N NaOH and extracted with EtOAc (2×). The organic layers were combined and washed with brine and dried over $MgSO_4$ to give a brownish solid 4G (1.03 g, 57%). MS (ESI) m/z: 377.9 $(M+H)^+$.

4H. Methyl(4-(6-(1-((tert-butoxycarbonyl)amino)but-3-en-1-yl)-3-chloropyridazin-4-yl)-3-nitrophenyl)carbamate: To a solution of 4G (1.03 g, 2.73 mmol) in DCM (27.3 mL) at 0° C. was added TEA (1.140 mL, 8.18 mmol) and $Boc_2O$ (0.760 mL, 3.27 mmol). The reaction mixture was stirred at 0° C. for 10 min, then was slowly raised to rt and continued to stir at rt for overnight. The crude product was concentrated and purified by silica gel chromatography to isolate 4H (414 mg, 36%) as orange colored foam. MS (ESI) m/z: 477.9 $(M+H)^+$.

4I. Methyl (3-amino-4-(6-((1S)-1-((tert-butoxycarbonyl)amino)but-3-en-1-yl)-3-chloropyridazin-4-yl)phenyl)carbamate: To a mixture of 4H (472 mg, 0.988 mmol) and iron powder (276 mg, 4.94 mmol) in acetic acid (7.407 mL) was added water (2.469 mL) and heated at 70° C. for 1 h. The reaction mixture was then cooled down on an ice-water bath, followed by neutralization with 10 N NaOH (aqueous). The reaction mixture was then extracted with EtOAc (3×) and the combined EtOAc layers were further washed with brine and dried over $MgSO_4$ to yield the crude product which was purified by silica gel chromatography. The purified product was then subjected to chiral HPLC separation using CHIRALPAK® AD column and 40% isopropanol/60% heptane mixture as mobile phase. Two peaks were seen eluting and the second eluting peak was collected and concentrated to yield yellow foam as 4I (144 mg, 32%). The first peak from the chiral column was the undesired isomer. MS (ESI) m/z: 447.8 $(M+H)^+$.

4J. methyl N-(4-{6-[(1S)-1-{[(tert-butoxy)carbonyl]amino}but-3-en-1-yl]-3-chloropyridazin-4-yl}-3-(2-methylbut-3-enamido)phenyl)carbamate: 4J was prepared in a similar way as in 1G by replacing intermediate 4 with racemic 2-Methylbut-3-enoic acid and 1F with 4I. MS (ESI) m/z: 530.0 $(M+H)^+$.

4K. Methyl N-[(11E,14S)-14-{[(tert-butoxy)carbonyl]amino}-18-chloro-10-methyl-9-oxo-8,16,17-triazatricyclo[13.3.1.0$^{2,7}$]nonadeca-1(19),2(7),3,5,11,15,17-heptaen-5-yl]carbamate:4K was prepared in a similar way as in example 1H by replacing 1G with 4J. MS (ESI) m/z: 502.0 $(M+H)^+$.

4L. Methyl N-[(10R,14S)-14-{[tert-butoxy)carbonyl]amino}-10-methyl-9-oxo-8,16,17-triazatricyclo[13.3.1.0$^{2,7}$]nonadeca-1(19),2(7),3,5,15,17-hexaen-5-yl]carbamate, TFA salt: To a solution of 4K (43 mg, 0.086 mmol) in Ethanol (3427 µl) was added ammonium formate (108 mg, 1.713 mmol) and Pd/C (18.23 mg, 0.017 mmol). The reaction was heated at 70° C. overnight. 18 mg Pd and 54 mg $NH_4CO_2H$ were added, and heating at 70° C. was continued for 3 days.

The reaction was cooled and filtered through a bed of Celite. The Celite was rinsed with DCM, EtOAc, MeOH, and the collected organics were concentrated. Early fractions from flash chromatography purification followed by reverse phase HPLC afforded 4L (17.8 mg, 44%). MS (ESI) m/z: 470.1 (M+H)+.

Example 4. Example 4 was prepared in a similar way as example 1 by replacing 1I with 4L. $^1$H NMR (500 MHz, METHANOL-d$_4$) δ 9.28 (d, J=1.9 Hz, 1H), 7.96 (d, J=2.2 Hz, 1H), 7.63 (d, J=8.5 Hz, 1H), 7.48-7.58 (m, 3H), 7.10 (td, J=9.2, 1.9 Hz, 1H), 6.09 (s, 1H), 5.77 (dd, J=12.4, 5.0 Hz, 1H), 4.18-4.27 (m, 1H), 3.89-3.98 (m, 1H), 3.77 (s, 3H), 2.72-2.88 (m, 2H), 2.62-2.70 (m, 1H), 2.23-2.32 (m, 1H), 1.86-2.03 (m, 2H), 1.49-1.59 (m, 1H), 1.34-1.46 (m, 1H), 0.99 (d, J=6.9 Hz, 3H), 0.64-0.79 (m, 1H). MS (ESI) m/z: 595.9 (M+H)+. Analytical HPLC (method A): RT=8.2 min, purity=99%.

Example 5 methyl N-[(10R,14S)-14-[4-(3-chloro-2,6-difluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2,4,6,15-pentaen-5-yl]carbamate

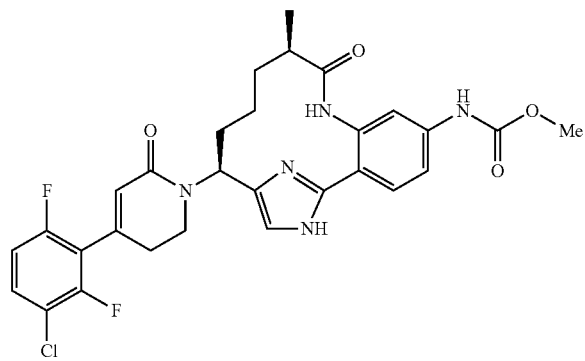 [SMILES: COC(=O)Nc1ccc2c(c1)NC(=O)[C@H](C)CCC[C@H](N1CCC(c3c(F)ccc(Cl)c3F)=CC1=O)c1c[nH]c-2n1]

5A. tert-butyl N-(1-diazo-2-oxohex-5-en-3-yl)carbamate: To a cooled (−40° C.) solution of 2-((t-butoxycarbonyl)amino)pent-4-enoic acid (15 g, 69.7 mmol) in THF (250 mL) was added N-methylmorpholine (9.19 mL, 84 mmol) followed by the dropwise addition of isobutyl chloroformate (10.98 mL, 84 mmol). The reaction was stirred at −40° C. for 20 minutes, whereupon it was filtered to remove the salts. The filtrate was added to a solution of diazomethane (4.39 g, 105 mmol) in Et$_2$O (500 mL) [Generated from 1-methyl-3-nitro-1-nitrosoguanidine]. The reaction mixture was stirred at −40° C. for 3 h and then the reaction was allowed to warm to rt. After 1 h, the reaction was purged with nitrogen for 30 minutes to remove the excess diazomethane. The reaction mixture was washed with a saturated solution of NaHCO$_3$ (2×100 mL), water (2×50 mL), brine solution (1×80 mL), dried by Na$_2$SO$_4$, filtered and concentrated to give a yellow solid (16 g). Purification by normal phase chromatography afforded 5A (12.5 g, 75%) as a yellow solid. $^1$H NMR (300 MHz, CDCl$_3$) δ ppm 5.66-5.83 (m, 1H), 5.48 (br. s., 1H), 5.19 (dd, J=3.21, 1.79 Hz, 1H), 5.03-5.16 (m, 2H), 4.24 (br. s., 1H), 2.35-2.62 (m, 2H), 1.46 (s, 9H).

5B. tert-butyl N-(1-bromo-2-oxohex-5-en-3-yl)carbamate: To a cooled (−15° C.) suspension of 5A (15 g, 62.7 mmol) in diethyl ether (500 mL) was added dropwise HBr (~47% in water) (18.11 mL, 157 mmol). After 15 min., the reaction was allowed to warm slowly to 0° C. over 2.5 h. The reaction was diluted with diethyl ether (100 mL) and the reaction was washed with water (2×100 mL), saturated solution of NaHCO$_3$ (1×80 mL), brine solution (1×80 mL), dried by Na$_2$SO$_4$, filtered and concentrated to give 5B (17 g, 93%) as a viscous yellow liquid which solidified in the refrigerator. $^1$H NMR (400 MHz, CDCl$_3$) δ ppm 5.62-5.76 (m, 1H), 5.12-5.21 (m, 2H), 5.08 (br. s., 1H), 4.57 (d, J=6.00 Hz, 1H), 3.99-4.12 (m, 2H), 2.38-2.67 (m, 2H), 1.43 (s, 9H).

5C. tert-butyl N-[1-(1H-imidazol-4-yl)but-3-en-1-yl]carbamate: A pressure tube containing a solution of 5B (28 g, 96 mmol), formamidine acetate (19.95 g, 192 mmol) and K$_2$CO$_3$ (53.0 g, 383 mmol) in DMF (200 mL) was heated at 100° C. overnight. The reaction mixture was cooled to rt and concentrated. The residue was partitioned between water (200 mL) and ethyl acetate (500 mL) and the layers were separated. The aqueous layer was extracted with ethyl acetate (2×200 mL). The organic layers were combined and washed with brine (1×100 mL), dried by Na$_2$SO$_4$, filtered and concentrated to give 5C (25.5 g, 84%) as a brown gummy solid. This was used in the next step without purification. MS (ESI) m/z: 238.2 (M+H)+.

5D. tert-butyl N-[1-(1-{[2-(trimethylsilyl)ethoxy]methyl}-1H-imidazol-4-yl)but-3-en-1-yl]carbamate: To a cooled (0° C.) solution of 5C (25.5 g, 107 mmol) in THF (260 mL) was added sodium hydride (4.73 g, 118 mmol). Following the addition, the reaction was allowed to warm to rt. After 30 min., the reaction was cooled to 0° C. and SEM-Cl (19.06 mL, 107 mmol) was added dropwise. The reaction was allowed to warm to rt and stir overnight. The reaction mixture was concentrated to give a brown gummy solid. Purification by normal phase chromatography gave 5D (11.5 gm, 70%) as a gummy, brown solid. MS (ESI) m/z: 368.4 (M+H)+. $^1$H NMR (400 MHz, CDCl$_3$) δ ppm 7.51 (d, J=1.25 Hz, 1H), 6.87 (s, 1H), 5.71 (dd, J=17.13, 10.13 Hz, 1H), 5.20 (s, 2H), 4.99-5.10 (m, 3H), 4.73 (dd, J=13.88, 6.38 Hz, 1H), 3.43-3.48 (m, 2H), 2.55-2.63 (m, 2H), 1.43 (s, 9H), 0.86-0.91 (m, 2H), 0.02-0.03 (m, 9H).

5E. tert-butyl N-[1-(2-bromo-1-{[2-(trimethylsilyl)ethoxy]methyl}-1H-imidazol-4-yl)but-3-en-1-yl]carbamate: To a cooled (−78° C.) solution of 5D (5.0 g, 13.60 mmol) in THF (100 mL) was added dropwise nBuLi (1.6 M in hexanes) (25.5 mL, 40.8 mmol). After 2 h, N-bromosuccinimide (2.421 g, 13.60 mmol) was added. After 2 h, the reaction mixture was quenched with a solution of saturated NH$_4$Cl (30 mL). The reaction mixture was extracted with ethyl acetate (3×50 mL). The organic layers were combined and washed with brine (1×50 mL), dried by Na$_2$SO$_4$, filtered and concentrated to give a gummy yellow solid. Purification by normal phase chromatography gave 5E (2.0 g, 26.5%) as a gummy, brown solid. MS (ESI) m/z: 446.0(M+H)+. $^1$H NMR (300 MHz, CDCl$_3$) δ ppm 6.95 (s, 1H), 5.63-5.78 (m, 1H), 5.22 (s, 2H), 5.02-5.14 (m, 3H), 4.64-4.74 (m, 1H), 3.50-3.57 (m, 2H), 2.58 (t, J=6.61 Hz, 2H), 1.44 (s, 9H), 0.89-0.96 (m, 2H), 0.01 (s, 9H).

5F. tert-butyl N-[(1S)-1-[2-(2-amino-4-nitrophenyl)-1-{[2-(trimethylsilyl)ethoxy]methyl}-1H-imidazol-4-yl]but-3-en-1-yl]carbamate (Enantiomer I) and 5G. tert-butyl N-[(1R)-1-[2-(2-amino-4-nitrophenyl)-1-{[2-(trimethylsilyl)ethoxy]methyl}-1H-imidazol-4-yl]but-3-en-1-yl]carbamate (Enantiomer II): To a solution of 5E (3 g, 6.72 mmol) and Intermediate 6 (5.02 g, 20.16 mmol) in toluene (40 mL) was added phosphoric acid, potassium salt (4.28 g, 20.16 mmol) and water (10 mL). The reaction mixture was purged with nitrogen for 15 min. Next, PdCl$_2$(dppf)-CH$_2$Cl$_2$ adduct (0.274 g, 0.336 mmol) was added and the reaction was heated at 110° C. After 3 h, the reaction was cooled to rt. The reaction mixture was diluted with ethyl acetate (80 mL) and then it was washed with saturated NaHCO$_3$ (1×50 mL), water (1×50 mL), brine (1×50 mL), dried Na$_2$SO$_4$, filtered and concentrated to give a gummy brown solid. Purification by normal phase chromatography gave the desired product as a gummy brown solid. The enantiomers were separated by chiral prep supercritical fluid chromatography which gave 5F (enantiomer I, 0.42 g, 12.5%) and 5G (Enantiomer-II, 0.545 g, 16%). 5F(Enantiomer-I): MS (ESI) m/z: 503.9 (M+H)$^+$. $^1$H NMR (400 MHz, DMSO-d$_6$ with two drops D$_2$O) δ ppm 7.56-7.62 (m, 2H), 7.39 (dd, J=8.53, 2.51 Hz, 1H), 7.20 (s, 1H), 5.65-5.75 (m, 1H), 5.23 (s, 2H), 4.95-5.08 (m, 2H), 4.55 (d, J=8.53 Hz, 1H), 3.40 (t, J=8.03 Hz, 2H), 2.32-2.49 (m, 2H), 1.33 (s, 9H), 0.69-0.77 (m, 2H), −0.14 (s, 9H). [α]$^{28.3}_D$=−44.80 (c 0.1, MeOH). 5G (Enantiomer-II): MS (ESI) m/z: 503.9 (M+H)$^+$. $^1$H NMR (400 MHz, DMSO-d$_6$ with two drops D$_2$O) δ ppm 7.60-7.64 (m, 2H), 7.38 (dd, J=8.78, 2.26 Hz, 1H), 7.22 (s, 1H), 5.66-5.77 (m, 1H), 5.24 (s, 2H), 4.95-5.09 (m, 2H), 4.57 (d, J=8.53 Hz, 1H), 3.44 (t, J=8.03 Hz, 2H), 2.32-2.48 (m, 2H), 1.35 (s, 9H), 0.73-0.80 (m, 2H), −0.11 (s, 9H). [α]$^{28.1}_D$+36.00 (c 0.1, MeOH).

5H. tert-butyl N-[(1S)-1-(2-{2-[(2R)-2-methylbut-3-enamido]-4-nitrophenyl}-1-{[2-(trimethylsilyl)ethoxy]methyl}-1H-imidazol-4-yl)but-3-en-1-yl]carbamate: To a cooled (0° C.) solution of 5F (0.650 g, 1.291 mmol) in DCM (10 mL) was added pyridine (0.313 mL, 3.87 mmol) followed by DMAP (0.015 g, 0.129 mmol). Next, freshly prepared (R)-2-methylbut-3-enoyl chloride (0.383 g, 3.23 mmol) in DCM (0.5 ml) was added dropwise. After 20 min., the reaction was concentrated. Purification by normal phase chromatography provided 5H (0.740 g, 98%) as a yellow oil. MS (ESI) m/z: 586.5 (M−H). $^1$H NMR (300 MHz, CD$_3$OD) δ ppm 9.34 (t, J=1.37 Hz, 1H), 8.05 (d, J=1.32 Hz, 2H), 7.35 (s, 1H), 6.98 (d, J=8.12 Hz, 1H), 5.76-6.04 (m, 2H), 5.36 (m, 2H), 5.04-5.26 (m, 4H), 4.80 (d, J=6.66 Hz, 1H), 3.65 (t, J=7.8 Hz, 2H), 3.25-3.30 (m, 1H), 2.64-2.79 (m, 1H), 2.50-2.61 (m, 1H), 1.46 (s, 9H), 1.32 (d, J=6.9, 3H), 0.93 (t, J=8.1 Hz, 3H), 0.01 (s, 9H).

5I. tert-butyl N-[(10R,11E,14S)-10-methyl-5-nitro-9-oxo-17-{[2-(trimethylsilyl)ethoxy]methyl}-8,17,18-triazatricyclo[13.2.1.0$^{2,7}$]octadeca-1(18),2,4,6,11,15-hexaen-14-yl]carbamate: A flame-dried 3 neck 1L RBF containing the solution of 5H (0.42 g, 0.717 mmol) and p-toluenesulfonic acid monohydrate (0.15 g, 0.789 mmol) in DCM (700 mL) was purged with argon for 1 h. Next, the reaction was warmed to reflux. After 1 h, a solution of Grubbs II (0.244 g, 0.287 mmol) in DCM (6 mL) was added dropwise. The reaction was allowed to stir at reflux overnight. The reaction mixture was cooled to rt, washed with saturated NaHCO$_3$ (2×80 mL), brine (1×80 mL), dried by Na$_2$SO$_4$, filtered and concentrated to give a gummy brown solid. Purification by normal phase chromatography afforded 5I (0.225 gm, 55.9%) as a gummy, yellow solid. MS (ESI) m/z: 558.5(M+H)$^+$. $^1$H NMR (400 MHz, CDCl$_3$) δ ppm 12.80 (br. s., 1H), 9.33 (br. s., 1H), 7.94-8.04 (m, 2H), 6.99 (d, J=8.00 Hz, 1H), 6.01-5.25 (m, 1H), 5.19-5.27 (m, 4H), 5.14 (d, J=7.50 Hz, 2H), 3.64-3.73 (m, 2H), 3.60 (m, 2H), 1.54 (s, 9H), 0.94-1.01 (m, 3H), 0.00 (s, 9H).

5J. tert-butyl N-[(10R,14S)-5-amino-10-methyl-9-oxo-17-{[2-(trimethylsilyl)ethoxy]methyl}-8,17,18-triazatricyclo[13.2.1.0$^{2,7}$]octadeca-1(18),2(7),3,5,15-pentaen-14-yl]carbamate: A solution of 5I (0.210 g, 0.377 mmol) in EtOAc (20 mL) was purged with nitrogen and vacuum. This was repeated 3 times. Next, platinum(IV) oxide (0.043 g, 0.188 mmol) was added and the reaction was purged with H$_2$ gas for several minutes (H$_2$ filled balloon). The reaction was stirred vigorously under a hydrogen atmosphere. After 16 h, the reaction was diluted with methanol (5 mL) and then it was filtered through a Celite bed, washing with methanol (2×5 mL). The filtrate was concentrated to give 5J (0.200 g, 95%) as a white solid. MS (ESI) m/z: 530.2 (M+H)$^+$. $^1$H NMR (400 MHz, CDCl$_3$) δ ppm 12.15 (br. s., 1H), 7.56 (d, J=8.51 Hz, 1H), 7.48 (d, J=2.25 Hz, 1H), 6.86 (s, 1H), 6.46 (dd, J=8.50, 2.50 Hz, 1H), 5.09-5.18 (m, 3H), 5.29-5.12 (m, 1H), 3.90-3.60 (m, 2H), 3.55-3.62 (m, 2H), 2.45-1.90 (m, 1H), 1.86-1.97 (m, 2H), 1.66-1.78 (m, 3H), 1.47 (s, 9H), 1.26 (s, 2H), 0.92-0.98 (m, 3H), 0.01 (s, 9H).

5K. tert-butyl N-[(10R,14S)-5-[(methoxycarbonyl)amino]-10-methyl-9-oxo-17-{[2-(trimethylsilyl)ethoxy]methyl}-8,17,18-triazatricyclo[13.2.1.0$^{2,7}$]octadeca-1(18),2(7),3,5,15-pentaen-14-yl]carbamate: To the cooled (0° C.) solution of 5J (0.195 g, 0.368 mmol) in DCM (5 mL) was added pyridine (0.045 mL, 0.552 mmol) followed by the dropwise addition of methyl chloroformate (0.043 mL, 0.552 mmol). After 10 min., the reaction was allowed to warm to rt. After 1 h, the reaction was diluted with DCM (30 mL) and then it was washed with sat.NaHCO$_3$ (2×20 mL), brine (1×20 mL), dried by Na$_2$SO$_4$, filtered and concentrated to give a gummy brown solid. Purification by normal phase chromatography provided 5K (0.145 g, 67%) as a yellow solid. MS (ESI) m/z: 588.2 (M+H)$^+$. $^1$H NMR (400 MHz, CD$_3$OD) δ ppm 7.71 (d, J=8.53 Hz, 1H), 7.64 (s, 1H), 7.44 (dd, J=8.28, 2.26 Hz, 1H), 7.12 (s, 1H), 5.19-5.27 (m, 2H), 3.78 (s, 3H), 3.64-3.73 (m, 2H), 2.58 (t, J=6.27 Hz, 1H), 2.01-2.11 (m, 1H), 1.76 (dt, J=6.40, 3.58 Hz, 2H), 1.52-1.62 (m, 2H), 1.47 (s, 9H), 1.35-1.41 (m, 2H), 1.07 (d, J=7.03 Hz, 3H), 0.99 (dt, J=8.91, 6.59 Hz, 2H), 0.05 (s, 9H).

5L. Methyl N-[(10R,14S)-14-[4-(3-chloro-2,6-difluorophenyl)-6-oxo-1,2,3,6-tetrahydropyridin-1-yl]-10-methyl-9-oxo-17-{[2-(trimethylsilyl)ethoxy]methyl}-8,17,18-triazatricyclo[13.2.1.0$^{2,7}$]octadeca-1(18),2,4,6,15-pentaen-5-yl]carbamate: Compound 5L (0.04 g, 74.8%, off-white solid) was prepared by following the procedures described in Example 1, by replacing 1I with 5K. MS (ESI) m/z: 714.2 (M+H)$^+$.

Example 5. To a brown solution of 5L (0.040 g, 0.056 mmol) in DCM (4 mL) was added TFA (0.5 mL, 6.49 mmol). After 4 h, additional TFA (0.5 mL) was added. After 3 h, the reaction was concentrated to give a residue. The residue was washed with petroleum ether (2×5 mL), diethyl ether (3×5 mL), and then dried under high vacuum to give a gummy, brown solid. Purification by reverse phase chromatography gave Example 5 (0.015 g, 38.1%) as a white solid. $^1$H NMR (400 MHz, CD$_3$OD) δ ppm 7.62-7.72 (m, 3H), 7.58 (td, J=8.66, 5.77 Hz, 1H), 7.50 (dd, J=8.53, 2.01 Hz, 1H), 7.14 (td, J=9.29, 1.51 Hz, 1H), 6.14 (br. s., 1H), 5.86 (dd, J=10.79, 5.77 Hz, 1H), 3.81-3.91 (m, 1H), 3.80 (s, 3H), 3.74-3.78 (m, 1H), 2.84 (t, J=6.53 Hz, 2H), 2.67-2.77 (m, 1H), 2.14-2.25 (m, 1H), 1.94-2.06 (m, 1H), 1.64-1.90 (m, 2H), 1.53 (br. s., 1H), 1.22-1.35 (m, 1H), 1.08 (d, J=7.03 Hz, 3H). MS (ESI) m/z: 584.2 (M+H)⁺. Analytical HPLC (method A): RT=5.8 min, purity=96%.

Example 6

Methyl N-[(10R,14S)-14-[4-(3-chloro-2,6-difluorophenyl)-6-oxo-1,2,3,6-tetrahydropyridin-1-yl]-12-hydroxy-10-methyl-9-oxo-8,16-diazatricyclo[13.3.1.0$^{2,7}$]nonadeca-1(19),2,4,6,15,17-hexaen-5-yl]carbamate, TFA salt

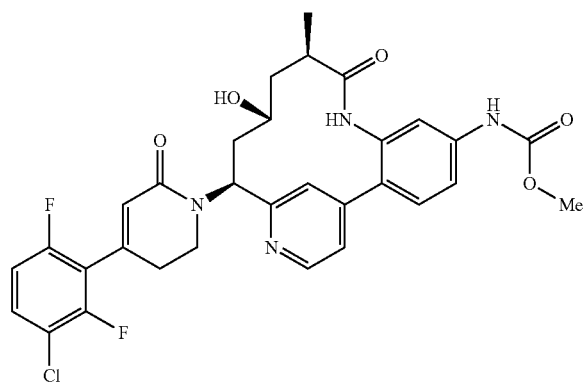 [SMILES: COC(=O)Nc1ccc2c(c1)NC(=O)[C@H](C)C[C@@H](O)C[C@H](N1CCC(c3c(F)ccc(Cl)c3F)=CC1=O)c1cc-2ccn1]

6A. tert-Butyl N-[(10R,14S)-11-hydroxy-5-[(methoxycarbonyl)amino]-10-methyl-9-oxo-8,16-diazatricyclo[13.3.1.0$^{2,7}$]nonadeca-1(18),2,4,6,15(19),16-hexaen-14-yl]carbamate and 6B.

tert-butyl N-[(10R,14S)-12-hydroxy-5-[(methoxycarbonyl)amino]-10-methyl-9-oxo-8,16-diazatricyclo[13.3.1.0$^{2,7}$]nonadeca-1(18),2,4,6,15 (19),16-hexaen-14-yl]carbamate (mixture)

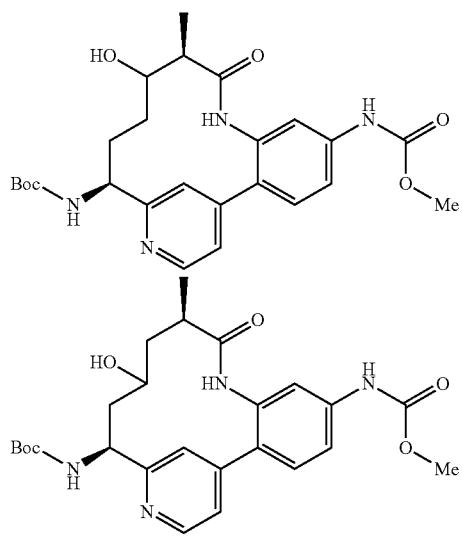

To a solution of tert-butyl N-[(10R,11E,14S)-5-[(methoxycarbonyl)amino]-10-methyl-9-oxo-8,16-diazatricyclo[13.3.1.0$^{2,7}$]nonadeca-1(18),2,4,6,11,15(19),16-heptaen-14-yl]carbamate (634 mg, 1.36 mmol) 1H in THF (13.6 mL) at 0° C. was added borane tetrahydrofuran complex (4.08 mL, 4.08 mmol) dropwise. The reaction was allowed to warm up to rt and stirred for 2.5 h. The reaction mixture was cooled to 0° C. and added sodium acetate (9.06 ml, 27.2 mmol), followed by hydrogen peroxide (4.16 mL, 40.8 mmol) dropwise. The reaction was warmed up to rt and stirred at for 8 h. The mixture was diluted with H₂O and extracted with EtOAc (2×). The combined organic layer was washed with brine, dried over MgSO₄, filtered, and concentrated. The residue was purified by silica gel chromatography (0-10% MeOH/DCM) to yield a mixture of two products 6A and 6B (323 mg, 49%) as a light grey solid. MS (ESI) m/z: 485.1 (M+H)⁺.

6C. tert-Butyl N-[(10R,14S)-5-[(methoxycarbonyl)amino]-10-methyl-9,11-dioxo-8,16-diazatricyclo[13.3.1.0$^{2,7}$]nonadeca-1(18),2,4,6,15(19),16-hexaen-14-yl]carbamate and 6D tert-butyl N-[(10R,14S)-5-[(methoxycarbonyl)amino]-10-methyl-9,12-dioxo-8,16-diazatricyclo[13.3.1.0$^{2,7}$]nonadeca-1(18),2,4,6,15(19),16-hexaen-14-yl]carbamate

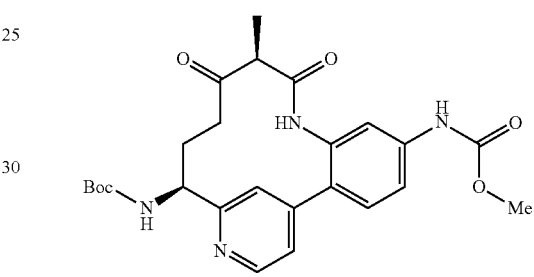

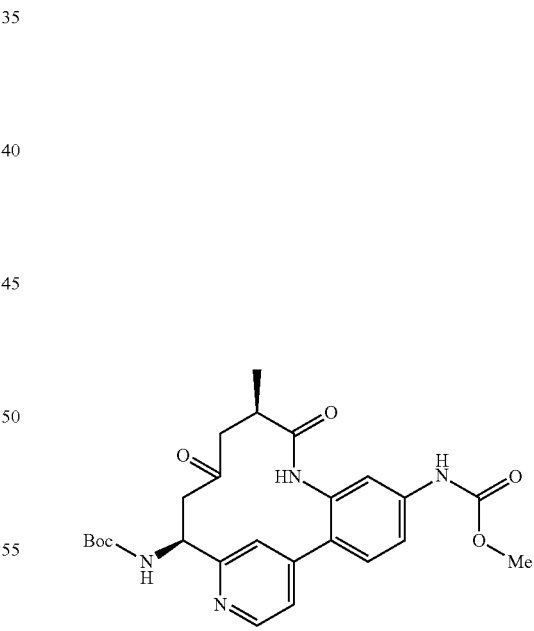

The mixture of 6A and 6B (116 mg, 0.239 mmol) in DCM (2.4 mL) was added Martin's reagent (132 mg, 0.311 mmol) at rt. The reaction was stirred at rt for 1.5 h. The mixture was diluted with DCM, washed with H₂O, brine, dried over MgSO₄, filtered, and concentrated. The residue was purified by silica gel chromatography (0-100% EtOAc/hexanes) to yield a 1:1 mixture of 6C and 6D (78 mg, 68%) as a white solid. MS (ESI) m/z: 483.1 (M+H)⁺.

6E. Methyl N-[(10R,14S)-14-amino-10-methyl-9,11-dioxo-8,16-diazatricyclo[13.3.1.0$^{2,7}$]nonadeca-1(18),2,4,6,15(19),16-hexaen-5-yl]carbamate and 6F methyl N-[(10R,14S)-14-amino-10-methyl-9,12-dioxo-8,16-diazatricyclo[13.3.1.0$^{2,7}$]nonadeca-1(18),2,4,6,15(19),16-hexaen-5-yl]carbamate (mixture)

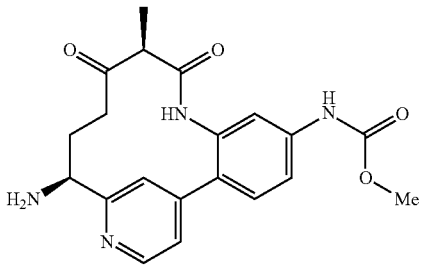

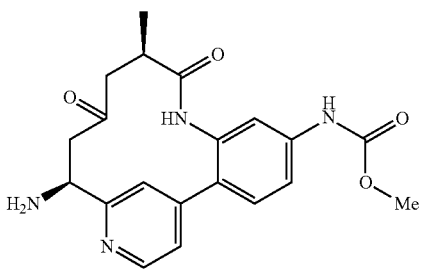

The mixture of 6C and 6D (78 mg, 0.162 mmol) was suspended in DCM (3 mL) and added TFA (0.623 mL, 8.08 mmol). The reaction became a clear light brownish solution and was stirred at rt for 1 h. The reaction was concentrated to yield a mixture of two regioisomers 6E and 6F (105 mg, 100%) as a yellow solid. MS (ESI) m/z: 383.1 (M+H)$^+$.

6G. Methyl N-[(10R,14S)-14-{N-[3-(3-chloro-2,6-difluorophenyl)-3-oxopropyl]-2-(diethoxyphosphoryl)acetamido}-10-methyl-9,12-dioxo-8,16-diazatricyclo[13.3.1.0$^{2,7}$]nonadeca-1(18),2,4,6,15(19),16-hexaen-5-yl]carbamate and 6H. Methyl N-[(10R,14S)-14-{N-[3-(3-chloro-2,6-difluorophenyl)-3-oxopropyl]-2-(diethoxyphosphoryl)acetamido}-10-methyl-9,11-dioxo-8,16-diazatricyclo[13.3.1.0$^{2,7}$]nonadeca-1(18),2,4,6,15(19),16-hexaen-5-yl]carbamate.

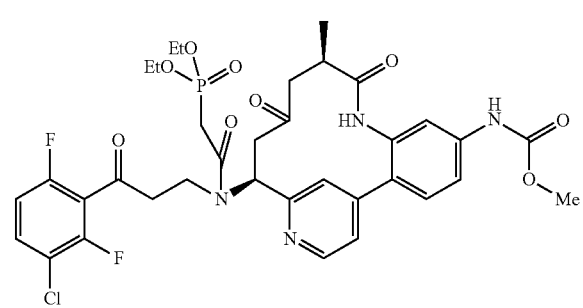

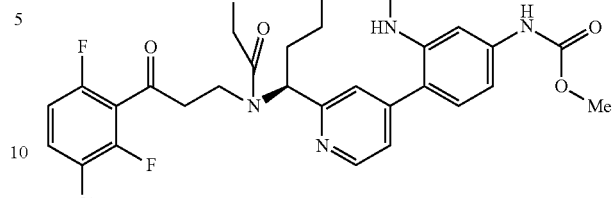

6G and 6H were prepared using a procedure analogous to 1K except that 1J was replaced with a 1:1 mixture of 6E and 6F. 6G was separated as a slower moving regioisomer on preparative HPLC. 6H was separated as a faster moving regioisomer on preparative HPLC MS (ESI) m/z: 763.0 (M+H)$^+$.

6I Methyl N-[(10R,14S)-14-[4-(3-chloro-2,6-difluorophenyl)-6-oxo-1,2,3,6-tetrahydropyridin-1-yl]-10-methyl-9,12-dioxo-8,16-diazatricyclo[13.3.1.0$^{2,7}$]nonadeca-1(19),2,4,6,15,17-hexaen-5-yl]carbamate, TFA salt: 6I was prepared using a procedure analogous to example 1 except that 1K was replaced with 6G. $^1$H NMR (500 MHz, CDCl$_3$) δ 8.78 (d, J=5.8 Hz, 1H), 7.82 (d, J=5.8 Hz, 1H), 7.62-7.69 (m, 3H), 7.53-7.61 (m, 2H), 7.13 (t, J=9.2 Hz, 1H), 6.14 (s, 1H), 6.09 (dd, J=12.1, 3.5 Hz, 1H), 3.90 (dd, J=18.1, 12.3 Hz, 1H), 3.80 (s, 3H), 3.64-3.73 (m, 1H), 3.42-3.51 (m, 1H), 2.99-3.29 (m, 3H), 2.71-2.81 (m, 2H), 2.36-2.45 (m, 1H), 1.32 (d, J=6.6 Hz, 3H). MS (ESI) m/z: 609.1 (M+H)$^+$. Analytical HPLC (method A): RT=7.4 min. Analytical HPLC (method B): RT=8.6 min, purity=98%.

Example 6: To a solution of 6I (6.7 mg, 9.27 μmol) in MeOH (0.5 mL) at 0° C. was added sodium borohydride (1.4 mg, 0.04 mmol). The reaction was warmed to rt and stirred for 2 h. The reaction was quenched with two drops of H$_2$O and HCl in MeOH. The mixture was concentrated and the residue was purified by reverse phase HPLC to afford example 27 (4 mg, 55%) as an off white solid. $^1$H NMR (500 MHz, CDCl$_3$) δ 9.62 (s, 1H), 8.73 (d, J=5.8 Hz, 1H), 7.94 (d, J=1.1 Hz, 1H), 7.75 (dd, J=5.8, 1.7 Hz, 1H), 7.61 (d, J=8.5 Hz, 1H), 7.52-7.58 (m, 2H), 7.48 (dd, J=8.4, 2.1 Hz, 1H), 7.11 (td, J=9.2, 1.7 Hz, 1H), 6.09-6.13 (m, 1H), 5.33 (dd, J=11.8, 5.8 Hz, 1H), 4.20 (dt, J=12.5, 6.1 Hz, 1H), 3.81-3.89 (m, 1H), 3.77 (s, 3H), 3.35 (s, 1H), 2.88-2.97 (m, 2H), 2.73-2.87 (m, 2H), 2.48-2.56 (m, 1H), 2.14-2.21 (m, 1H), 1.99-2.08 (m, 1H), 1.61-1.71 (m, 1H), 1.13 (d, J=7.2 Hz, 3H). MS (ESI) m/z: 611.1 (M+H)$^+$. Analytical HPLC (method A): RT=6.0 min, purity=99%.

Example 7

Methyl N-[(14S)-14-[4-(6-bromo-3-chloro-2-fluorophenyl)-6-oxo-1,2,3,6-tetrahydropyridin-1-yl]-9-oxo-8,16,18-triazatricyclo[13.2.1.0$^{2,7}$]octadeca-1(17),2,4,6,15(18)-pentaen-5-yl]carbamate, TFA salt

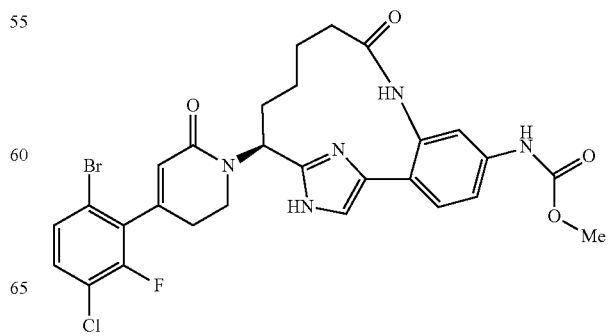

Example 7 was prepared by following the procedures described in Example 3. ¹H NMR (500 MHz, METHANOL-d₄) δ 7.61 (d, J=1.9 Hz, 1H), 7.58-7.44 (m, 5H), 5.98 (t, J=1.4 Hz, 1H), 5.48 (dd, J=12.0, 5.6 Hz, 1H), 3.96-3.84 (m, 2H), 3.79 (s, 3H), 2.91-2.82 (m, 1H), 2.81-2.72 (m, 1H), 2.47 (ddd, J=13.5, 6.6, 3.0 Hz, 1H), 2.36-2.13 (m, 3H), 1.89-1.78 (m, 1H), 1.70-1.59 (m, 1H), 1.35-1.14 (m, 2H). MS (ESI) m/z: 632.0 (M+H)⁺. Analytical HPLC (method A): RT=6.6 min, purity=100%.

Example 8

Methyl N-[(10R,14S)-14-[4-(3-chloro-2-fluorophenyl)-6-oxo-1,2,3,6-tetrahydropyridin-1-yl]-10-methyl-9-oxo-8,16-diazatricyclo[13.3.1.0²,⁷]nonadeca-1(18),2,4,6,15(19),16-hexaen-5-yl]carbamate, TFA salt

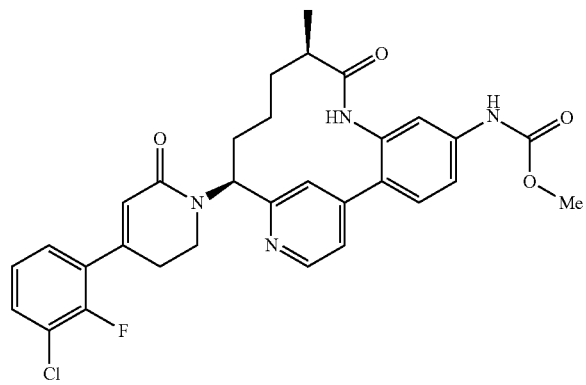

Example 8 was prepared by following the procedures described in Example 1. ¹H NMR (500 MHz, METHANOL-d₄) δ 8.75 (d, J=6.1 Hz, 1H), 8.10 (d, J=1.7 Hz, 1H), 7.87 (dd, J=5.9, 1.8 Hz, 1H), 7.65 (d, J=8.3 Hz, 1H), 7.60-7.49 (m, 3H), 7.41 (ddd, J=8.1, 6.7, 1.7 Hz, 1H), 7.22 (td, J=8.0, 1.1 Hz, 1H), 6.20 (s, 1H), 5.37 (dd, J=12.4, 5.0 Hz, 1H), 3.80-3.75 (m, 4H), 3.74-3.66 (m, 1H), 2.97-2.88 (m, 1H), 2.87-2.79 (m, 1H), 2.64 (m, 1H), 2.36-2.25 (m, 1H), 2.11-2.01 (m, 1H), 1.97-1.85 (m, 1H), 1.62 (m, 1H), 1.33 (m, 1H), 1.05 (d, J=6.9 Hz, 3H), 1.00-0.86 (m, 1H). MS (ESI) m/z: 577.0 (M+H)⁺. Analytical HPLC (method A): RT=6.5 min. purity=97%.

Example 9

Methyl N-[(10R,14S)-14-[4-(3-chloro-2-fluorophenyl)-6-oxo-1,2,3,6-tetrahydropyridin-1-yl]-10-methyl-9-oxo-8,16,18-triazatricyclo[13.2.1.0²,⁷]octadeca-1(17),2,4,6,15(18)-pentaen-5-yl]carbamate, TFA salt

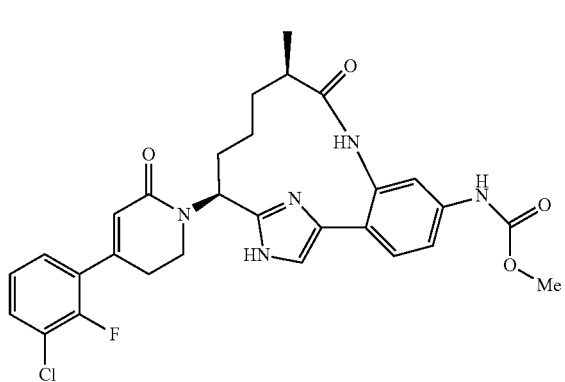 [SMILES: COC(=O)Nc1ccc2c(c1)NC(=O)[C@H](C)CCC[C@H](N1CCC(c3cccc(Cl)c3F)=CC1=O)c1nc-2c[nH]1]

Example 9 was prepared by following the procedures described in Example 3. ¹H NMR (500 MHz, METHANOL-d₄) δ 7.58 (d, J=1.9 Hz, 1H), 7.56-7.47 (m, 3H), 7.46-7.40 (m, 2H), 7.24 (td, J=8.0, 1.1 Hz, 1H), 6.21 (s, 1H), 5.44 (dd, J=11.6, 6.3 Hz, 1H), 3.90-3.83 (m, 1H), 3.81-3.74 (m, 4H), 3.06-2.97 (m, 1H), 2.95-2.87 (m, 1H), 2.78-2.70 (m, 1H), 2.38-2.29 (m, 1H), 2.15-2.06 (m, 1H), 1.84-1.74 (m, 1H), 1.67-1.46 (m, 2H), 1.05 (d, J=6.9 Hz, 3H), 0.75 (br. s., 1H). MS (ESI) m/z: 565.9 (M+H)⁺. Analytical HPLC (method A): RT=6.0 min, purity=97%.

Example 10

Methyl N-[(10S,14S)-14-[4-(3-chloro-2-fluorophenyl)-6-oxo-1,2,3,6-tetrahydropyridin-1-yl]-10-methyl-9-oxo-8,18-diazatricyclo[13.3.1.0²,⁷]nonadeca-1(19),2,4,6,15,17-hexaen-5-yl]carbamate, TFA salt

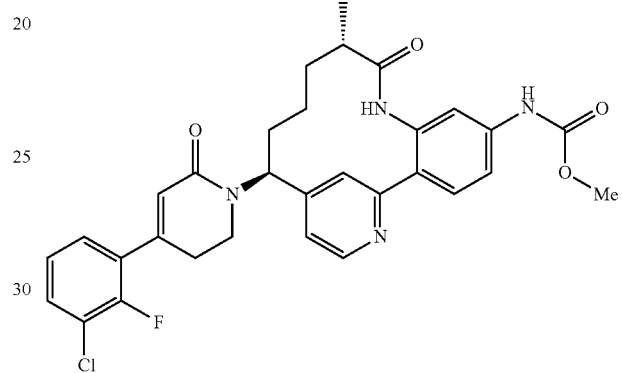

Example 10 was prepared by following the procedures described in Example 1. ¹H NMR (500 MHz, ACETONITRILE-d3) δ 8.58 (d, J=5.5 Hz, 1H), 8.15 (s, 1H), 7.94 (s, 1H), 7.87 (s, 1H), 7.73 (d, J=8.5 Hz, 1H), 7.34-7.44 (m, 5H), 7.26-7.32 (m, 1H), 7.12 (dt, J=0.8, 8.0 Hz, 1H), 6.06 (s, 1H), 5.38 (dd, J=3.9, 11.6 Hz, 1H), 3.91-4.12 (m, 3H), 3.64 (s, 3H), 3.54-3.61 (m, 1H), 3.45 (td, J=6.3, 12.5 Hz, 1H), 2.64-2.79 (m, 2H), 2.37-2.45 (m, 1H), 1.97-2.07 (m, 1H), 1.58-1.66 (m, 1H), 1.40-1.50 (m, 1H), 1.13-1.23 (m, 2H), 1.02 (d, J=6.9 Hz, 2H). MS (ESI) m/z: 576.9 (M+H)⁺. Analytical HPLC (method A): RT=6.4 min, purity=100%.

Example 11

Methyl N-[(10R,14S)-14-[4-(3-chloro-2-fluorophenyl)-6-oxo-1,2,3,6-tetrahydropyridin-1-yl]-10-methyl-9-oxo-8,18-diazatricyclo[13.3.1.0²,⁷]nonadeca-1(19),2,4,6,15,17-hexaen-5-yl]carbamate, TFA salt

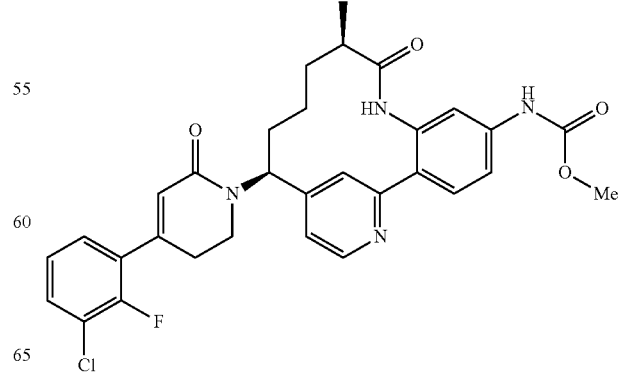

Example 11 was prepared by following the procedures described in Example 1. $^1$H NMR (500 MHz, ACETONITRILE-d3) δ 8.59 (d, J=5.5 Hz, 1H), 8.07 (s, 1H), 7.89 (s, 1H), 7.73 (s, 1H), 7.65 (d, J=8.3 Hz, 1H), 7.43 (d, J=2.2 Hz, 1H), 7.39 (dtd, J=1.8, 3.4, 8.3 Hz, 2H), 7.36 (dd, J=1.4, 5.5 Hz, 1H), 7.27 (ddd, J=1.7, 6.7, 7.9 Hz, 1H), 7.10 (dt, J=1.1, 8.0 Hz, 1H), 6.04 (d, J=0.8 Hz, 1H), 5.42 (dd, J=4.0, 12.5 Hz, 1H), 4.35 (s, 1H), 3.65 (s, 3H), 3.46 (td, J=7.2, 12.6 Hz, 1H), 3.29 (td, J=6.3, 12.5 Hz, 1H), 2.61 (t, J=6.7 Hz, 2H), 2.32 (ddd, J=2.9, 6.7, 9.4 Hz, 1H), 1.96-2.05 (m, 1H), 1.65-1.75 (m, 1H), 1.37-1.45 (m, 1H), 1.17-1.27 (m, 2H), 1.12-1.07 (m, 1H), 0.96 (d, J=6.9 Hz, 3H). MS (ESI) m/z: 577.2 (M+H)$^+$. Analytical HPLC (method A): RT=6.4 min, purity=100%.

Example 12

Methyl N-[(10R,14S)-14-[4-(3-chloro-2,6-difluorophenyl)-6-oxo-1,2,3,6-tetrahydropyridin-1-yl]-17-methoxy-10-methyl-9-oxo-8,16-diazatricyclo[13.3.1.0$^{2,7}$]nonadeca-1(18),2,4,6,15(19),16-hexaen-5-yl]carbamate, TFA salt

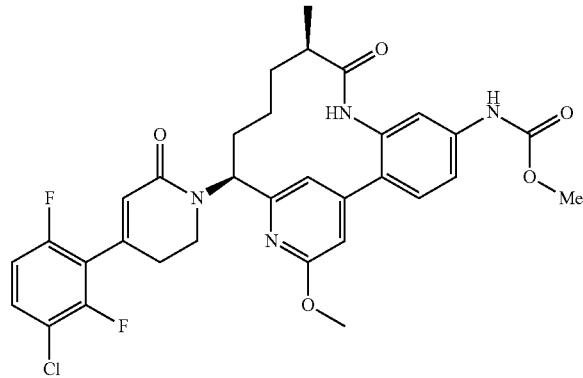 [SMILES: COC(=O)Nc1ccc2c(c1)NC(=O)[C@H](C)CCC[C@H](N1CCC(c3c(F)ccc(Cl)c3F)=CC1=O)c1cc-2cc(OC)n1]

Example 12 was prepared by following the procedures described in Example 1. $^1$H NMR (500 MHz, METHANOL-d$_4$) δ 7.56-7.42 (m, 4H), 7.14 (s, 1H), 7.12-7.06 (m, 1H), 6.77 (s, 1H), 6.11 (s, 1H), 5.66 (dd, J=12.5, 4.9 Hz, 1H), 4.38-4.27 (m, 1H), 3.98 (s, 1H), 3.95 (s, 3H), 3.92-3.81 (m, 1H), 3.76 (s, 3H), 2.84-2.61 (m, 3H), 2.24-2.12 (m, 1H), 2.05-1.93 (m, 1H), 1.81-1.69 (m, 1H), 1.58-1.35 (m, 2H), 0.99 (d, J=7.1 Hz, 3H), 0.71 (br. s., 1H). MS (ESI) m/z: 624.9 (M+H)$^+$. Analytical HPLC (method A): RT=5.8 min, purity=95%.

Example 13

Methyl N-[(10R,14S)-14-[4-(3-chloro-2,6-difluorophenyl)-6-oxo-1,2,3,6-tetrahydropyridin-1-yl]-10-methyl-9,17-dioxo-8,16-diazatricyclo[13.3.1.0$^{2,7}$]nonadeca-1(18),2,4,6,15(19)-pentaen-5-yl]carbamate, TFA salt

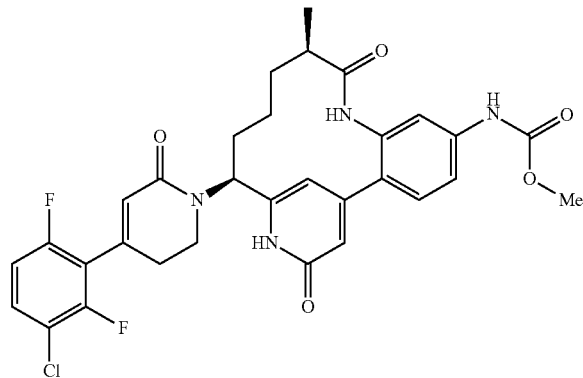 [SMILES: COC(=O)Nc1ccc2c(c1)NC(=O)[C@H](C)CCC[C@H](N1CCC(c3c(F)ccc(Cl)c3F)=CC1=O)c1cc-2cc(=O)[nH]1]

Example 13 was prepared by following the procedures described in Example 1. $^1$H NMR (500 MHz, METHANOL-d$_4$) δ 9.53 (s, 1H), 7.58-7.47 (m, 4H), 7.10 (td, J=9.2, 1.8 Hz, 1H), 6.70 (s, 1H), 6.57 (s, 1H), 6.15 (s, 1H), 5.17 (dd, J=12.3, 3.4 Hz, 1H), 3.78 (s, 3H), 3.62-3.53 (m, 1H), 3.48-3.40 (m, 1H), 3.37 (s, 3H), 2.69 (t, J=6.6 Hz, 2H), 2.52 (d, J=6.6 Hz, 1H), 2.16 (d, J=9.3 Hz, 1H), 1.98-1.79 (m, 2H), 1.70-1.56 (m, 2H), 1.17 (d, J=6.8 Hz, 3H). MS (ESI) m/z: 610.9 (M+H)$^+$. Analytical HPLC (method A): RT=8.2 min, purity=98%.

Example 14

Methyl N-[(10R,14S)-14-[4-(3-chloro-2,6-difluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate, TFA salt

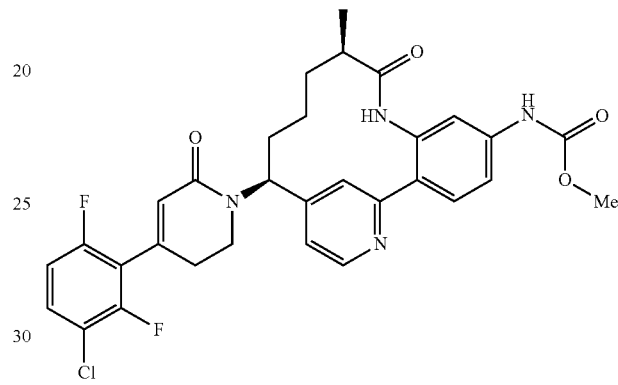

Example 14 was prepared by following the procedures described in Example 1. $^1$H NMR (500 MHz, ACETONITRILE-d3) δ 8.64 (d, J=5.8 Hz, 1H), 8.17 (s, 1H), 7.96 (s, 1H), 7.82 (d, J=1.1 Hz, 1H), 7.62 (d, J=8.5 Hz, 1H), 7.49 (dd, J=1.7, 5.8 Hz, 1H), 7.45 (d, J=1.9 Hz, 1H), 7.36-7.42 (m, 2H), 6.96 (dt, J=1.8, 9.3 Hz, 1H), 5.95 (s, 1H), 5.41 (dd, J=4.4, 12.4 Hz, 1H), 3.64 (s, 3H), 3.47-3.55 (m, 2H), 3.38 (td, J=6.3, 12.5 Hz, 2H), 2.50-2.61 (m, 1H), 2.30-2.39 (m, 1H), 1.95-2.04 (m, 1H), 1.89 (d, J=4.4 Hz, 1H), 1.66-1.74 (m, 1H), 1.38-1.42 (m, 1H), 1.08-1.22 (m, 2H), 0.93 (d, J=6.9 Hz, 3H). MS (ESI) m/z: 549.9 (M+H)$^+$. Analytical HPLC (method A): RT=6.4 min, purity=100%

Example 15

Methyl N-[(10R,14R)-14-[4-(3-chloro-2,6-difluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2(7),3,5,15-pentaen-5-yl]carbamate, TFA salt

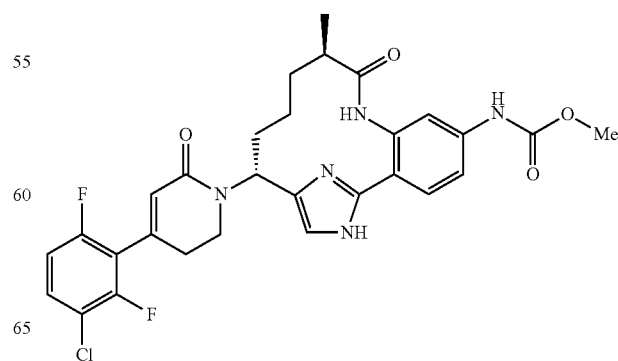

Example 15 was prepared by following the procedures described in Example 5, by replacing compound 5F in step 5H with compound 5G. ¹H NMR (400 MHz, CD₃OD) δ ppm 7.65-7.70 (m, 2H), 7.49-7.58 (m, 2H), 7.21-7.28 (m, 1H), 7.11 (td, J=9.16, 1.76 Hz, 1H), 6.13 (s, 1H), 5.64 (dd, J=12.05, 4.02 Hz, 1H), 3.78 (s, 3H), 2.87-2.94 (m, 1H), 2.65-2.75 (m, 2H), 2.43-2.55 (m, 1H), 1.80-1.90 (m, 2H), 1.43-1.62 (m, 4H), 1.21 (d, J=6.78 Hz, 3H), 0.98 (d, J=7.53 Hz, 1H). MS (ESI) m/z: 584 (M+H)⁺. Analytical HPLC (method A): RT=7.0 min, purity=85%

Example 16 methyl N-[(10R,14S)-14-[4-(2-bromo-5-chlorophenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]carbamate, TFA salt

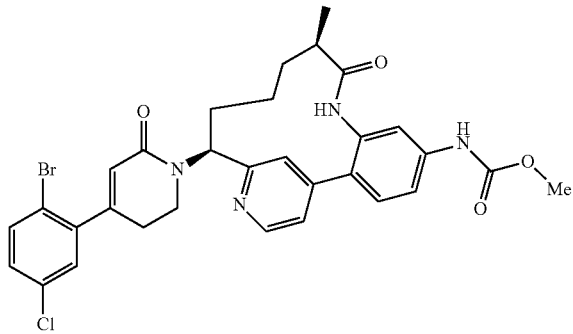 [SMILES: COC(=O)Nc1ccc2c(c1)NC(=O)[C@H](C)CCC[C@H](N1CCC(c3cc(Cl)ccc3Br)=CC1=O)c1cc-2ccn1]

Example 16 was prepared by following the procedures described in Example 1. ¹H NMR (500 MHz, CD₃OD) δ 8.73 (d, J=5.5 Hz, 1H), 7.93 (s, 1H), 7.72 (d, J=4.7 Hz, 1H), 7.69-7.62 (m, 2H), 7.59-7.53 (m, 2H), 7.37 (d, J=2.5 Hz, 1H), 7.34-7.31 (m, 1H), 5.95-5.90 (m, 1H), 5.52 (dd, J=12.5, 4.3 Hz, 1H), 3.89-3.83 (m, 1H), 3.81-3.77 (m, 4H), 2.85-2.72 (m, 2H), 2.67-2.60 (m, 1H), 2.33-2.25 (m, 1H), 2.08-1.92 (m, 2H), 1.62 (dd, J=14.4, 6.2 Hz, 1H), 1.31 (br. s., 1H), 1.10-1.04 (m, 3H). MS (ESI) m/z: 636.9 (M+H)⁺. Analytical HPLC (method A): RT=7.22 min, purity=90%.

Example 17 methyl N-[(10R,14S)-14-[4-(6-bromo-3-chloro-2-fluorophenyl)-6-oxo-1,2,3,6-tetrahydropyridin-1-yl]-10-methyl-9-oxo-8,18-diazatricyclo[13.3.1.0²,⁷]nonadeca-1(19),2(7),3,5,15,17-hexaen-5-yl]carbamate, TFA salt

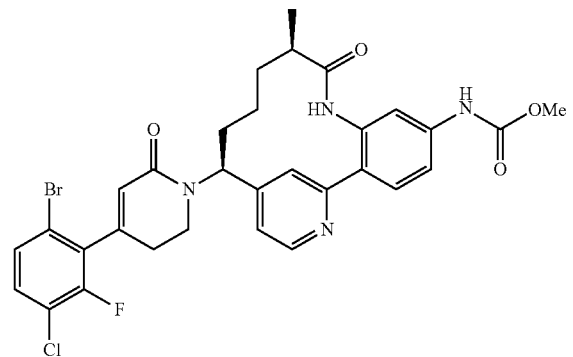 [SMILES: COC(=O)Nc1ccc2c(c1)NC(=O)[C@H](C)CCC[C@H](N1CCC(c3c(Br)ccc(Cl)c3F)=CC1=O)c1ccnc-2c1]

Example 17 was prepared by following the procedures described in Example 1. ¹H NMR (500 MHz, ACETONITRILE-d3) δ 8.57 (d, J=5.23 Hz, 1H), 7.99 (s, 1H), 7.84 (br. s., 1H), 7.68 (d, J=9.08 Hz, 1H), 7.36-7.40 (m, 3H), 7.27-7.31 (m, 1H), 7.23 (d, J=4.95 Hz, 1H), 5.80 (s, 1H), 5.46 (dd, J=3.58, 12.38 Hz, 1H), 3.64 (s, 3H), 3.43-3.51 (m, 1H), 3.23 (td, J=6.50, 12.59 Hz, 1H), 2.36-2.45 (m, 4H), 1.69-1.73 (m, 3H), 1.31-1.48 (m, 3H), 1.07-1.12 (m, 1H), 0.99 (d, J=6.88 Hz, 3H). MS (ESI) m/z: 657.2 (M+H)⁺. Analytical HPLC (method A): RT=6.8 min, purity=100%.

Example 18

Methyl N-[(10R,14S)-14-[4-(6-bromo-3-chloro-2-fluorophenyl)-6-oxo-1,2,3,6-tetrahydropyridin-1-yl]-10-methyl-9-oxo-8,17,18-triazatricyclo[13.2.1.0²,⁷]octadeca-1(18),2(7),3,5,15-pentaen-5-yl]carbamate, TFA salt

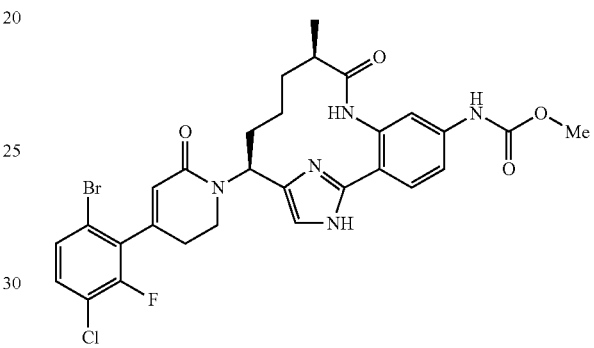

Example 18 was prepared by following the procedures described in Example 5, by replacing Intermediate 1 with Intermediate 2. ¹H NMR (400 MHz, CD₃OD) δ ppm ¹H NMR (400 MHz, METHANOL-d₄) δ ppm 7.69-7.73 (m, 1H), 7.61-7.67 (m, 2H), 7.54-7.58 (m, 1H), 7.40-7.53 (m, 2H), 5.95-6.01 (m, 1H), 5.88 (dd, J=11.04, 6.02 Hz, 1H), 3.81-3.96 (m, 2H), 3.80 (s, 3H), 2.77 (t, J=6.27 Hz, 2H), 2.14-2.33 (m, 1H), 2.01 (dd, J=12.30, 6.27 Hz, 1H), 1.64-1.88 (m, 2H), 1.53 (br. s., 1H), 1.34-1.27 (m, 2H), 1.07-1.11 (m, 3H). MS (ESI) m/z: 645.5 (M+H)⁺. Analytical HPLC (method A): RT=7.0 min, purity=99%.

Example 19 methyl N-[(10S,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0²,⁷]nonadeca-1(19),2,4,6,15,17-hexaen-5-yl]carbamate, TFA salt

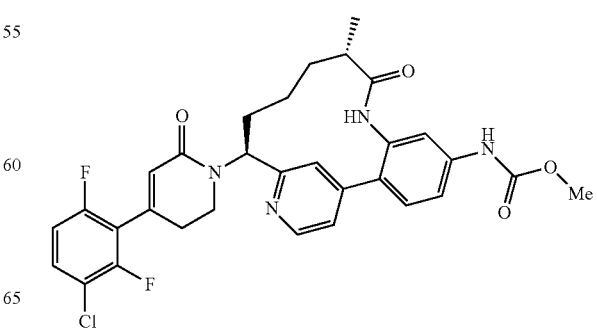

Example 19 was prepared by following the procedures described in Example 1. 1H NMR (500 MHz, DMSO-d6) δ ppm: 9.88 (s, 1H), 9.47 (s, 1H), 8.59 (d, J=5.2 Hz, 1H), 7.69 (m, 1H), 7.53 (s, 2H), 7.46 (s, 1H), 7.37 (s, 1H), 7.32-7.25 (m, 2H), 6.05 (s, 1H), 5.57 (dd, J=12.5, 4.3 Hz, 1H), 4.18 (m, 1H), 3.77 (m, 1H), 3.69 (s, 3H), 2.71-2.65 (m, 2H), 2.25-2.17 (m, 1H), 2.05-1.95 (m, 2H), 1.79 (m, 1H), 1.73-1.62 (m, 1H), 1.38-1.28 (m, 1H), 1.14 (d, J=7.2 Hz, 3H), 0.71 (m, 1H). MS (ESI) m/z: 595.2(M+H)+. Analytical HPLC (method A): RT=6.3 min, purity=95%.

Example 20

Methyl N-[(10R,14S)-14-[4-(3-chloro-2,6-difluorophenyl)-2-oxo-1,2-dihydropyridin-1-yl]-10-methyl-9-oxo-8,16-diazatricyclo[13.3.1.0$^{2,7}$]nonadeca-1(19),2,4,6,15,17-hexaen-5-yl]carbamate, TFA salt

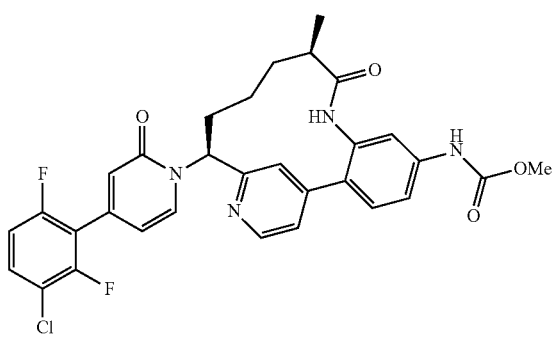 [SMILES: COC(=O)Nc1ccc2c(c1)NC(=O)[C@H](C)CCC[C@H](n1ccc(-c3c(F)ccc(Cl)c3F)cc1=O)c1cc-2ccn1]

Example 1 (54 mg, 0.091 mmol) in DMSO (1 mL) was added 1-bromo-4-chlorobenzene (17.37 mg, 0.091 mmol), NH$_4$OH (0.016 mL, 0.118 mmol), L-Proline (10.45 mg, 0.091 mmol), Copper(I) Iodide (17.28 mg, 0.091 mmol) and Potassium Carbonate (37.6 mg, 0.272 mmol), flushed with Ar, sealed and heated at 95° C. After 16 hrs, reaction mixture was filtered off solid, purified by prep HPLC twice desired fraction dried under high vacuum, then lyophilized to yield example 20 as 4.89 mg fluffy off white solid. $^1$H NMR (400 MHz, METHANOL-d$_4$) δ 9.59 (s, 1H), 8.68 (d, J=5.5 Hz, 1H), 8.22 (d, J=7.0 Hz, 1H,), 8.01 (s, 1H), 7.70-7.47 (m, 5H), 7.16 (td, J=9.1, 1.8 Hz, 1H), 6.68 (s, 1H), 6.57 (d, J=7.0 Hz, 1H), 6.04 (dd, J=12.3, 4.4 Hz, 1H), 3.77 (s, 3H), 2.73 (d, J=6.6 Hz, 1H), 2.41 (t, J=12.4 Hz, 1H), 2.21-1.96 (m, 2H), 1.69-1.45 (m, 2H), 1.01 (d, J=7.0 Hz, 3H), 0.78 (br. s., 1H). MS (ESI) m/z: 593.1(M+H)$^+$. Analytical HPLC (method A): RT=7.9 min, purity=100%.

Example 21

(10R,14S)-14-[4-(3-Chloro-2,6-difluorophenyl)-6-oxo-1,2,3,6-tetrahydropyridin-1-yl]-5-[(methoxycarbonyl)amino]-10-methyl-9-oxo-8,16-diazatricyclo[13.3.1.0$^{2,7}$]nonadeca-1(19),2,4,6,15,17-hexaen-16-ium-16-olate, TFA salt

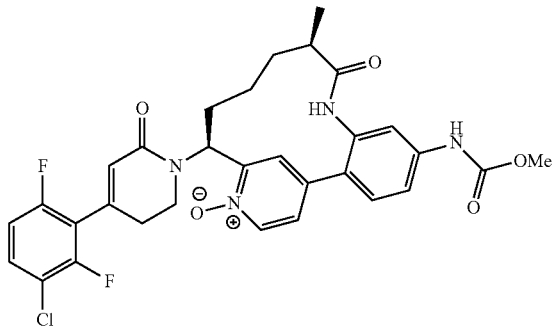 [SMILES: COC(=O)Nc1ccc2c(c1)NC(=O)[C@H](C)CCC[C@H](N1CCC(c3c(F)ccc(Cl)c3F)=CC1=O)c1cc-2cc[n+]1[O-]]

3-Chlorobenzoperoxoic acid (8 mg, 0.036 mmol), example 1 (5.6 mg, 9.41 nmol) in a 1 dram vial was added ClCH$_2$CH$_2$Cl (0.2 mL) and stirred at rt for 2 h. The reaction mixture was washed with sat. NaHCO$_3$, and brine, dried over MgSO$_4$, filtered off solid, concentrated and purified by prep HPLC. The desired fraction was dried under vacuum, and further lyophilized to yield example 21 as 3 mg biege solid. $^1$H NMR (400 MHz, METHANOL-d$_4$) δ 9.57 (s, 1H), 8.44 (d, J=6.6 Hz, 1H), 7.87 (s, 1H), 7.66-7.49 (m, 5H), 7.11 (td, J=9.2, 1.5 Hz, 1H), 6.08 (s, 1H), 5.59 (d, J=11.2 Hz, 1H), 3.80 (s, 3H), 3.70-3.58 (m, 1H), 3.54-3.41 (m, 1H), 2.81-2.62 (m, 2H), 2.57-2.26 (m, 2H), 2.18-2.00 (m, 1H), 1.97-1.83 (m, 1H), 1.79-1.56 (m, 2H), 1.22 (d, J=6.6 Hz, 3H), 1.14-0.97 (m, 1H). MS (ESI) m/z: 611.1 (M+H)$^+$. Analytical HPLC (method A): RT=7.5 min, purity=97%.

Example 22

Methyl N-[(10R,14S)-14-[4-(3-chlorophenyl)-6-oxo-1,2,3,6-tetrahydropyridin-1-yl]-10-methyl-9-oxo-8,16-diazatricyclo[13.310$^{2,7}$]nonadeca-1(19),2,4,6,15,17-hexaen-5-yl]carbamate, TFA salt

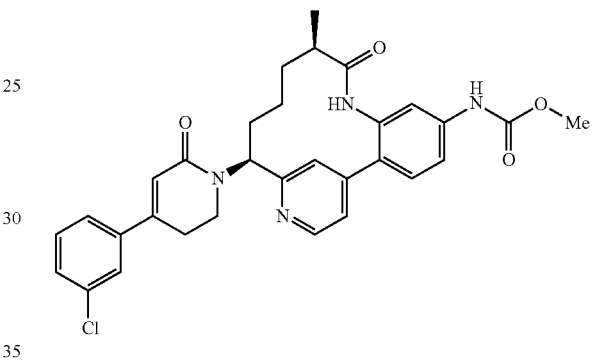

Example 22 was prepared by following the procedures described in Example 1. $^1$H NMR (400 MHz, METHANOL-d$_4$) δ 9.67 (s, 1H), 8.96-8.62 (m, 1H), 8.28-8.07 (m, 1H), 8.02-7.80 (m, 1H), 7.70-7.49 (m, 5H), 7.46-7.38 (m, 2H), 6.38-6.17 (m, 1H), 5.60-5.24 (m, 1H), 4.29-4.07 (m, 1H), 3.77 (s, 5H), 2.90 (br. s., 2H), 2.73-2.58 (m, 1H), 2.42-2.24 (m, 1H), 2.16-2.01 (m, 1H), 1.92 (br. s., 1H), 1.71-1.55 (m, 1H), 1.42-1.20 (m, 2H), 1.05 (d, J=6.8 Hz, 3H), 0.99-0.85 (m, 1H). MS (ESI) m/z: 559.2 (M+H)$^+$. Analytical HPLC (method A): RT=6.3 min, purity=97%.

Example 23

Methyl N-[(10R,14S)-14-[4-(3-chloro-2,6-difluorophenyl)-6-oxo-1,2,3,6-tetrahydropyridin-1-yl]-11-hydroxy-10-methyl-9-oxo-8,16-diazatricyclo[13.3.1.0$^{2,7}$]nonadeca-1(19),2,4,6,15,17-hexaen-5-yl]carbamate, TFA salt

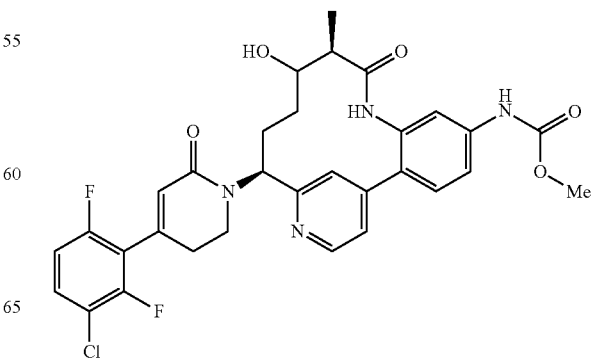

Example 23 was prepared by following the procedures described in Example 6 by replacing 6H with 6F in step 6I. $^1$H NMR (500 MHz, CDCl$_3$) δ 9.60 (s, 1H), 8.70 (d, J=5.5 Hz, 1H), 7.88 (s, 1H), 7.66 (d, J=5.8 Hz, 1H), 7.52-7.60 (m, 3H), 7.43-7.49 (m, 1H), 7.06-7.14 (m, 1H), 6.11 (s, 1H), 5.46 (dd, J=12.0, 5.9 Hz, 1H), 4.22-4.33 (m, 2H), 3.83-3.93 (m, 1H), 3.77 (s, 3H), 2.83-3.00 (m, 2H), 2.73-2.83 (m, 1H), 2.15-2.29 (m, 2H), 1.39-1.50 (m, 1H), 0.92 (d, J=6.9 Hz, 3H), 0.48-0.59 (m, 1H). MS (ESI) m/z: 611.2 (M+H)$^+$. Analytical HPLC (method A): RT=6.1 min, purity=99%.

Example 24

Methyl N-[(10R,14S)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaen-5-yl]carbamate

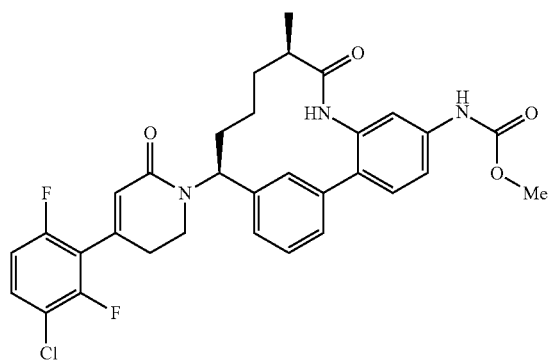 [SMILES: COC(=O)Nc1ccc2c(c1)NC(=O)[C@H](C)CCC[C@H](N1CCC(c3c(F)ccc(Cl)c3F)=CC1=O)c1cccc-2c1]

2A (R)—N-[(1E)-(3-bromophenyl)methylidene]-2-methylpropane-2-sulfinamide: To a mixture of (R)-2-methylpropane-2-sulfinamide (2.4326 g, 20.07 mmol) and Cs$_2$CO$_3$ (9.81 g, 30.1 mmol) in DCM (50 mL) was added dropwise a solution of 3-bromobenzaldehyde (4.08 g, 22.08 mmol) in DCM (50 mL) over 10 min and the mixture stirred at ambient temperature for overnight. The reaction mixture was filtered through celite and the filter pad washed with DCM then with EtOAc. Filtrate was dried over MgSO$_4$ and concentrated to give an oil which was purified by silica gel chromatography to give 2A (4.7626 g, 16.53 mmol, 82% yield) as an faint yellow colored oil. $^1$H NMR (500 MHz, CDCl$_3$) δ 8.55 (s, 1H), 8.05 (t, J=1.8 Hz, 1H), 7.76 (dt, J=7.7, 1.2 Hz, 1H), 7.68-7.65 (m, 1H), 7.41-7.36 (m, 1H), 1.31-1.29 (m, 9H).

2B (R)—N—((S)-1-(3-Bromophenyl)but-3-en-1-yl)-2-methylpropane-2-sulfinamide: To round bottomed flask equipped with a reflux condensor was charged 2A (2.4673 g, 8.56 mmol), allyl bromide (0.889 mL, 10.27 mmol) and THF (40 mL) to which was added indium (1.180 g, 10.27 mmol) and the mixture heated to 60° C. under nitrogen where it was stirred for overnight. The reaction mixture was quenched by addition of water (40 mL) and the mixture stirred for 15 min, diluted with EtOAc (30 mL), and phases separated. Aqueous phase was extracted with EtOAc (2×) and combined organics washed with brine, dried (Na$_2$SO$_4$), filtered and evaporated to give a faint yellow colored oil which was placed under vacuum for overnight to give 3A (3.18 g, 89%). $^1$H NMR (500 MHz, CDCl$_3$) δ 7.50 (t, J=1.8 Hz, 1H), 7.45-7.42 (m, 1H), 7.27-7.21 (m, 1H), 5.79-5.69 (m, 1H), 5.24-5.22 (m, 1H), 5.22-5.19 (m, 2H), 4.48 (ddd, J=8.1, 5.5, 2.1 Hz, 1H), 3.69 (s, 1H), 2.64-2.58 (m, 1H), 2.47 (dt, J=14.0, 8.4 Hz, 1H), 1.23 (s, 9H).

Example 24 was prepared by following the procedures described in Example 1 by replacing 1B with 2B in step 1C. $^1$H NMR (400 MHz, METHANOL-d$_4$) δ 7.50 (s, 1H), 7.45-7.35 (m, 4H), 7.33 (d, J=1.8 Hz, 1H), 7.31-7.26 (m, 1H), 7.20 (d, J=7.7 Hz, 1H), 6.96 (td, J=9.2, 1.8 Hz, 1H), 6.00 (s, 1H), 5.52 (dd, J=12.9, 3.2 Hz, 1H), 3.65 (s, 3H), 3.37 (ddd, J=12.8, 8.7, 5.4 Hz, 1H), 3.07-2.99 (m, 1H), 2.54-2.44 (m, 1H), 2.40-2.23 (m, 2H), 2.16-2.04 (m, 1H), 1.83-1.73 (m, 1H), 1.72-1.57 (m, 2H), 1.55-1.45 (m, 1H), 1.08 (d, J=6.8 Hz, 3H), 1.03-0.91 (m, 1H). MS (ESI) m/z: 594.2 (M+H)$^+$. Analytical HPLC (method A): RT=10.1 min.

Example 25

Isomer 2 methyl N-[(10S,14R)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate

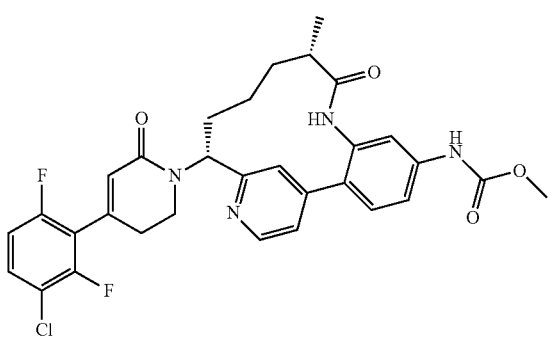 [SMILES: COC(=O)Nc1ccc2c(c1)NC(=O)[C@@H](C)CCC[C@@H](N1CCC(c3c(F)ccc(Cl)c3F)=CC1=O)c1cc-2ccn1]

and Example 26

Isomer 3 methyl N-[(10R,14R)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate

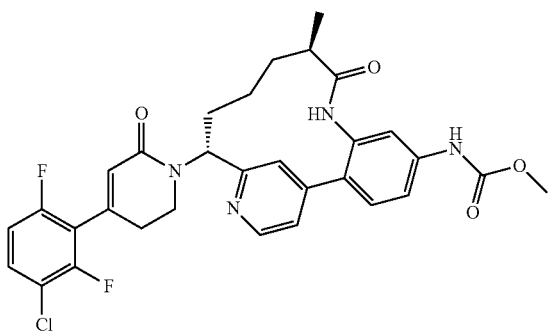 [SMILES: COC(=O)Nc1ccc2c(c1)NC(=O)[C@H](C)CCC[C@@H](N1CCC(c3c(F)ccc(Cl)c3F)=CC1=O)c1cc-2ccn1]

25A methyl N-{14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl}carbamate: 25A was prepared was prepared using a procedure analogous to Example 1 by replacing intermediate 4 with 2-methylbut-3-enoic acid.

Example 25 and Example 26: 25A (187 mg) was subjected to chiral SFC separation using Regis Whelk-O (R,R) 250×30 mm column, with a mixture of 45% MeOH-0.1% DEA/55% CO2 with a flow rate of 85 mL/min and 150 bar at 40° C. 4 isomers were obtained. Example 25 (isomer 2) (95 mg): MS (ESI) m/z: 595.2 (M+H)+. Analytical HPLC (method A): RT=6.37 min, purity>99% $^1$H NMR (500 MHz, DMSO-$d_6$) δ 9.88 (s, 1H), 9.70 (s, 1H), 8.60 (d, J=5.0 Hz, 1H), 7.68 (td, J=8.7, 5.6 Hz, 1H), 7.55-7.45 (m, 3H), 7.36 (s, 1H), 7.33-7.22 (m, 2H), 6.04 (s, 1H), 5.60 (dd, J=12.7, 4.4 Hz, 1H), 3.97 (br. s., 1H), 3.69 (s, 4H), 2.67-2.53 (m, 3H), 2.11-1.98 (m, 1H), 1.96-1.87 (m, 1H), 1.72-1.60 (m, 1H), 1.48-1.37 (m, 1H), 1.29-1.16 (m, 1H), 0.87 (d, J=6.9 Hz, 3H), 0.53 (br. s., 1H). Example 26 (isomer 3) (59 mg). MS (ESI) m/z: 595.2 (M+H)+. Analytical HPLC (method A): RT=6.19 min, purity>99%. $^1$H NMR (500 MHz, DMSO-$d_6$) δ 9.88 (s, 1H), 9.47 (s, 1H), 8.59 (d, J=5.0 Hz, 1H), 7.69 (td, J=8.7, 5.6 Hz, 1H), 7.53 (s, 2H), 7.46 (s, 1H), 7.37 (s, 1H), 7.32-7.23 (m, 2H), 6.05 (s, 1H), 5.57 (dd, J=12.4, 4.4 Hz, 1H), 4.18 (dt, J=12.9, 6.5 Hz, 1H), 3.81-3.73 (m, 1H), 3.69 (s, 3H), 2.72-2.65 (m, 2H), 2.26-2.16 (m, 1H), 2.07-1.94 (m, 1H), 1.86-1.74 (m, 1H), 1.70-1.62 (m, 2H), 1.40-1.20 (m, 1H), 1.14 (d, J=7.2 Hz, 3H), 0.71 (m, 1H).

Example 27

Methyl N-[(14S)-14-[4-(3-chloro-2,6-difluorophenyl)-6-oxo-1,2,3,6-tetrahydropyridin-1-yl]-9-oxo-8,16-diazatricyclo[13.3.1.0$^{2,7}$]nonadeca-1(19),2(7),3,5,15,17-hexaen-5-yl]carbamate, TFA salt

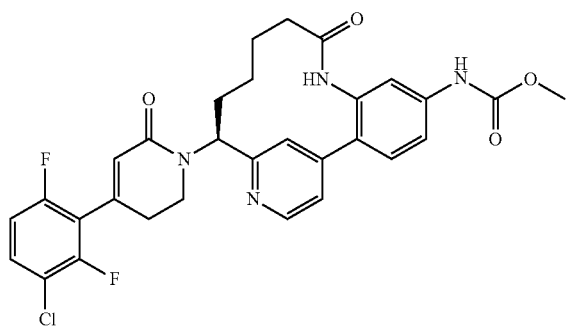 [SMILES: COC(=O)Nc1ccc2c(c1)NC(=O)CCCC[C@H](N1CCC(c3c(F)ccc(Cl)c3F)=CC1=O)c1cc-2ccn1]

Example 27 was prepared according to the procedures described in Example 1 by replacing Intermediate 4 with but-3-enoic acid in step 1G. $^1$H NMR (500 MHz, METHANOL-$d_4$) δ 8.71 (d, J=5.8 Hz, 1H), 7.99 (s, 1H), 7.74 (dd, J=5.8, 1.7 Hz, 1H), 7.63 (d, J=8.5 Hz, 1H), 7.58-7.51 (m, 3H), 7.10 (td, J=9.2, 1.7 Hz, 1H), 6.10 (s, 1H), 5.46 (dd, J=12.4, 4.7 Hz, 1H), 3.96 (dt, J=12.6, 6.2 Hz, 1H), 3.83-3.75 (m, 4H), 2.90-2.81 (m, 1H), 2.79-2.70 (m, 1H), 2.47 (ddd, J=13.0, 7.5, 2.9 Hz, 1H), 2.31-2.23 (m, 1H), 2.16-1.99 (m, 2H), 1.97-1.87 (m, 1H), 1.75-1.65 (m, 1H), 1.38-1.24 (m, 1H), 1.09-0.97 (m, 1H). MS (ESI) m/z: 581.3 (M+H)+. Analytical HPLC (method A): RT=6.23 min, purity=100%.

Example 28

Methyl N-[(14S)-14-[4-(3-chloro-2,6-difluorophenyl)-2-oxo-1,2-dihydropyridin-1-yl]-9-oxo-8,16-diazatricyclo[13.3.1.0$^{2,7}$]nonadeca-1(19),2(7),3,5,15,17-hexaen-5-yl]carbamate, TFA salt

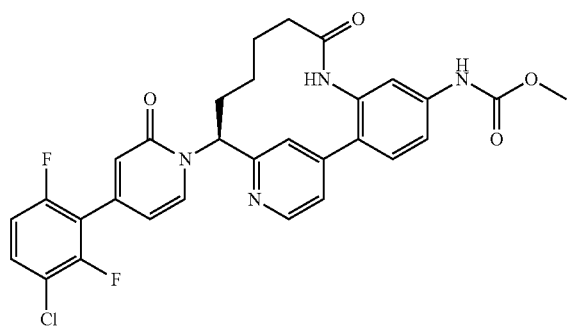 [SMILES: COC(=O)Nc1ccc2c(c1)NC(=O)CCCC[C@H](n1ccc(-c3c(F)ccc(Cl)c3F)cc1=O)c1cc-2ccn1]

To a sealable vial containing Example 27 (0.016 g, 0.023 mmol) and copper(I) iodide (0.438 mg, 2.302 nmol) in DMSO (1 mL) was added 3-iodopyridine (9.44 mg, 0.046 mmol) and Cs$_2$CO$_3$ (0.030 g, 0.092 mmol). The vial was vacuumed and back-filled with argon three times, then the vial was sealed and heated at 80° C. After 20 h, the reaction was cooled to rt. Purification by reverse phase HPLC afforded Example 28 (2.1 mg, 12.9% yield) as a yellow solid. $^1$H NMR (500 MHz, METHANOL-$d_4$) δ 8.64 (d, J=5.2 Hz, 1H), 8.39 (d, J=7.4 Hz, 1H), 7.78 (s, 1H), 7.60 (td, J=8.6, 5.6 Hz, 1H), 7.55-7.44 (m, 4H), 7.15 (td, J=9.1, 1.7 Hz, 1H), 6.64 (s, 1H), 6.56 (d, J=7.2 Hz, 1H), 6.13 (dd, J=12.7, 4.7 Hz, 1H), 3.76 (s, 3H), 2.52 (dd, J=10.9, 6.7 Hz, 1H), 2.34-2.26 (m, 1H), 2.12-1.94 (m, 3H), 1.71-1.62 (m, 1H), 1.57-1.47 (m, 1H), 0.92-0.80 (m, 1H). MS (ESI) m/z: 579.3 (M+H)+. Analytical HPLC (method A): RT=7.18 min, purity=99.3%.

Example 29

Methyl N-[(10R,14S)-14-[4-(3-chloro-2,6-difluorophenyl)-6-oxo-1,2,3,6-tetrahydropyridin-1-yl]-17-fluoro-10-methyl-9-oxo-8-azatricyclo[13.3.1.0$^{2,7}$]nonadeca-1(19),2,4,6,15,17-hexaen-5-yl]carbamate

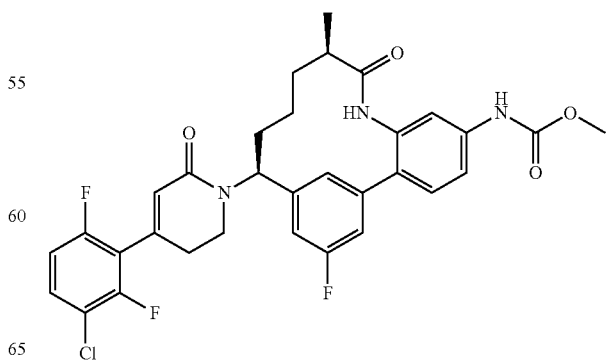

Example 29 was prepared according to the procedures described in Example 24. $^1$H NMR (500 MHz, DMSO-d6) δ 9.88-9.82 (m, 1H), 9.64-9.60 (m, 1H), 7.73-7.65 (m, 1H), 7.56-7.49 (m, 2H), 7.39-7.34 (m, 2H), 7.31-7.19 (m, 2H), 7.08-7.03 (m, 1H),), 5.50-5.43 (m, 1H), 3.70 (s, 3H), 3.18-3.08 (m, 1H), 2.63-2.55 (m, 1H), 2.47-2.32 (m, 1H), 2.13-2.02 (m, 2H), 1.80-1.68 (m, 2H), 1.49-1.36 (m, 3H), 1.08-0.99 (m, 1H) ppm. MS (ESI) m/z: 612.3 (M+H)$^+$. Analytical HPLC (method D): RT=2.071 min., purity>95%.

What is claimed is:

1. A compound according to Formula (VIII):

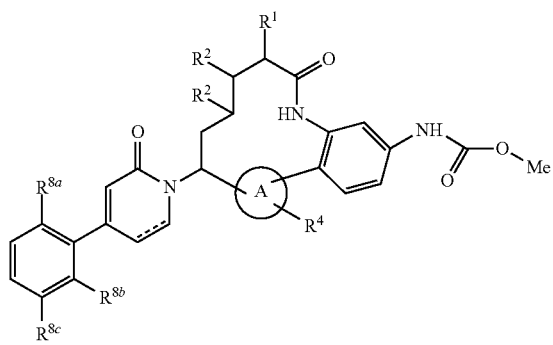

(VIII)

or a stereoisomer, a tautomer, a pharmaceutically acceptable salt thereof, wherein:

ring A is independently selected from

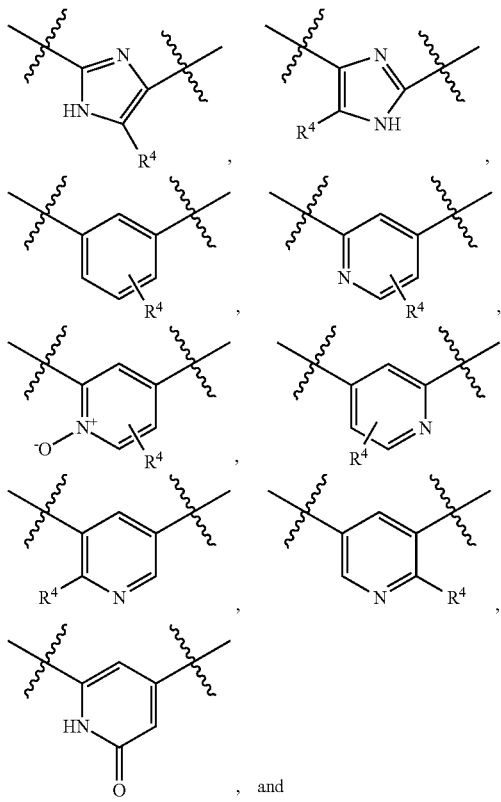

---- is an optional bond;

$R^1$ is independently selected from H, hydroxy, and $C_{1-4}$alkyl;

$R^2$, at each occurrence, is independently selected from H and hydroxyl;

$R^4$ is independently selected from H, OH, F, $OC_{1-4}$ alkyl, and CN;

$R^{8a}$ is independently selected from H, F, Cl, and Br;

$R^{8b}$ is independently selected from H and F; and $R^{8c}$ is independently selected from H, F, and Cl.

2. The compound according to claim 1, wherein:

ring A is independently selected from

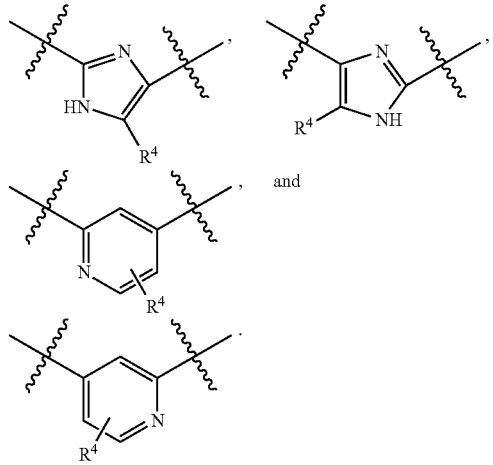

3. The compound according to claim 2, having Formula (IX):

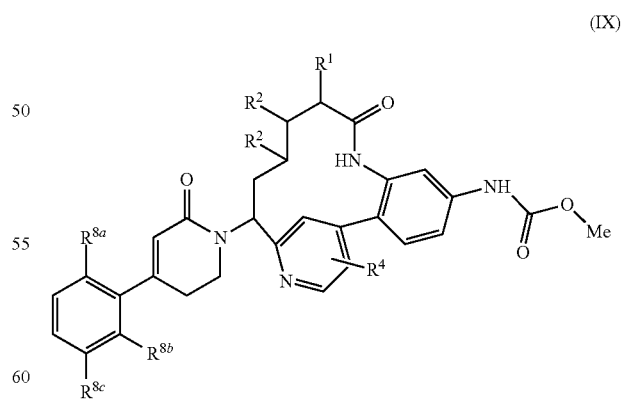

(IX)

or a stereoisomer, a tautomer, a pharmaceutically acceptable salt thereof, wherein:

$R^1$ is independently selected from H and methyl;

$R^2$, at each occurrence, is independently selected from H and hydroxyl;

R⁴ is independently selected from H, OH, F, OC$_{1-4}$ alkyl, and CN;
R$^{8a}$ is independently selected from H, F, Cl, and Br;
R$^{8b}$ is independently selected from H and F; and
R$^{8c}$ is independently selected from H, F, and Cl.

4. The compound according to claim 3 wherein:
R⁴ is H;
R$^{8a}$ is independently selected from H, F, and Br;
R$^{8b}$ is F; and
R$^{8c}$ is independently selected from H, F, and Cl.

5. A pharmaceutical composition comprising one or more compounds according to claim 1 and a pharmaceutically acceptable carrier or diluent.

6. A method for the treatment and/or prophylaxis of a thromboembolic disorder, comprising: administering to a patient in need thereof a therapeutically effective amount of a compound of claim 1, or a stereoisomer, a tautomer, or a pharmaceutically acceptable salt thereof.

7. A method according to claim 6, wherein the thromboembolic disorder is selected from arterial cardiovascular thromboembolic disorders, venous cardiovascular thromboembolic disorders, and thromboembolic disorders in the chambers of the heart or in the peripheral circulation.

8. A method according to claim 6, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

9. A compound according to claim 1 selected from
Methyl N-[(10R,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate,
Methyl N-[(10R,14S)-14-[4-(6-bromo-3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9-oxo-8,16,17-triazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2,4,6,15-pentaen-5-yl]carbamate,
Methyl N-[(10R,14S)-14-[4-(3-chloro-2,6-difluorophenyl)-6-oxo-1,2,3,6-tetrahydropyridin-1-yl]-12-hydroxy-10-methyl-9-oxo-8,16-diazatricyclo[13.3.1.0$^{2,7}$]nonadeca-1(19),2,4,6,15,17-hexaen-5-yl]carbamate,
Methyl N-[(14S)-14-[4-(6-bromo-3-chloro-2-fluorophenyl)-6-oxo-1,2,3,6-tetrahydropyridin-1-yl]-9-oxo-8,16,18-triazatricyclo[13.2.1.0$^{2,7}$]octadeca-1(17),2,4,6,15(18)-pentaen-5-yl]carbamate,
Methyl N-[(10R,14S)-14-[4-(3-chloro-2-fluorophenyl)-6-oxo-1,2,3,6-tetrahydropyridin-1-yl]-10-methyl-9-oxo-8,16-diazatricyclo[13.3.1.0$^{2,7}$]nonadeca-1(18),2,4,6,15(19),16-hexaen-5-yl]carbamate,
Methyl N-[(10R,14S)-14-[4-(3-chloro-2-fluorophenyl)-6-oxo-1,2,3,6-tetrahydropyridin-1-yl]-10-methyl-9-oxo-8,16,18-triazatricyclo[13.2.1.0$^{2,7}$]octadeca-1(17),2,4,6,15(18)-pentaen-5-yl]carbamate,
Methyl N-[(10S,14S)-14-[4-(3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate,
Methyl N-[(10R,14S)-14-[4-(3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-6-oxo-1,2,3,6-tetrahydropyridin-1-yl]-17-methoxy-10-methyl-9-oxo-8,16-diazatricyclo[13.3.1.0$^{2,7}$]nonadeca-1(18),2,4,6,15(19),16-hexaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9,17-dioxo-8,16-diazatricyclo[13.3.1.0$^{2,7}$]nonadeca-1(18),2,4,6,15(19)-pentaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9-oxo-8,18-diazatricyclo[13.3.1.0$^{2,7}$]nonadeca-1(19),2,4,6,15,17-hexaen-5-yl]carbamate,
Methyl N-[(10R,14R)-14-[4-(3-chloro-2,6-difluorophenyl)-6-oxo-1,2,3,6-tetrahydropyridin-1-yl]-10-methyl-9-oxo-8,17,18-triazatricyclo[13.2.1.02'7]octadeca-1(18),2(7),3,5,15-pentaen-5-yl]carbamate,
Methyl N-[(10R,14S)-14-[4-(2-bromo-5-chlorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate,
methyl N-[(10R,14S)-14-[4-(6-bromo-3-chloro-2-fluorophenyl)-6-oxo-1,2,3,6-tetrahydropyridin-1-yl]-10-methyl-9-oxo-8,18-diazatricyclo[13.3.1.0$^{2,7}$]nonadeca-1(19),2(7),3,5,15,17-hexaen-5-yl]carbamate,
Methyl N-[(10R,14S)-14-[4-(6-bromo-3-chloro-2-fluorophenyl)-6-oxo-1,2,3,6-tetrahydropyridin-1-yl]-10-methyl-9-oxo-8,17,18-triazatricyclo[13.2.1.0$^{2,7}$]octadeca-1(18),2(7),3,5,15-pentaen-5-yl]carbamate,
methyl N-[(10S,14S)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-2-oxo-1,2-dihydropyridin-1-yl]-10-methyl-9-oxo-8,16-diazatricyclo[13.3.1.0$^{2,7}$]nonadeca-1(19),2,4,6,15,17-hexaen-5-yl]carbamate,
(10R,14S)-14-[4-(3-Chloro-2,6-difluorophenyl)-6-oxo-1,2,3,6-tetrahydropyridin-1-yl]-5-[(methoxycarbonyl)amino]-10-methyl-9-oxo-8,16-diazatricyclo[13.3.1.0$^{2,7}$]nonadeca-1(19),2,4,6,15,17-hexaen-16-ium-16-olate,
Methyl N-[(10R,14S)-14-[4-(3-chlorophenyl)-6-oxo-1,2,3,6-tetrahydropyridin-1-yl]-10-methyl-9-oxo-8,16-diazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-6-oxo-1,2,3,6-tetrahydropyridin-1-yl]-11-hydroxy-10-methyl-9-oxo-8,16-diazatricyclo[13.3.1.0$^{2,7}$]nonadeca-1(19),2,4,6,15,17-hexaen-5-yl]carbamate,
Methyl N-[(10R,14S)-14-[4-(3-chloro-2,6-difluorophenyl)-6-oxo-1,2,3,6-tetrahydropyridin-1-yl]-10-methyl-9-oxo-8-azatricyclo[13.3.1.0$^{2,7}$]nonadeca-1(19),2,4,6,15,17-hexaen-5-yl]carbamate,
Methyl N-[(10S,14R)-14-[4-(3-chloro-2,6-difluorophenyl)-6-oxo-1,2,3,6-tetrahydropyridin-1-yl]-10-methyl- 9-oxo-8,16-diazatricyclo[13.3.1.0$^{2,7}$]nonadeca-1(19), 2,4,6,15,17-hexaen-5-yl]carbamate, Methyl N-[(10R,14R)-14-[4-(3-chloro-2,6-difluorophenyl)-6-oxo-1,2,3,6-tetrahydropyridin-1-yl]-10-methyl-9-oxo-8,16-diazatricyclo[13.3.1.0$^{2,7}$]nonadeca-1(19), 2,4,6,15,17-hexaen-5-yl]carbamate, Methyl N-[(14S)-14-[4-(3-chloro-2,6-difluorophenyl)-6-oxo-1,2,3,6-tetrahydropyridin-1-yl]-9-oxo-8,16-diazatricyclo[13.3.1.0$^{2,7}$]nonadeca-1(19),2(7),3,5,15,17-hexaen-5-yl]carbamate, Methyl N-[(14S)-14-[4-(3-chloro-2,6-difluorophenyl)-2-oxo-1,2-dihydropyridin-1-yl]-9-oxo-8,16-diazatricyclo[13.3.1.0$^{2,7}$]nonadeca-1(19),2(7),3,5,15,17-hexaen-5-yl]carbamate, and Methyl N-[(10R,14S)-14-[4-(3-chloro-2,6-difluorophenyl)-6-oxo-1,2,3,6-tetrahydropyridin-1-yl]-17-fluoro-10-methyl-9-oxo-8-azatricyclo[13.3.1.0$^{2,7}$]nonadeca-1(19),2,4,6,15,17-hexaen-5-yl]carbamate.

* * * * *